(12) United States Patent
Shelton, IV et al.

(10) Patent No.: US 8,424,740 B2
(45) Date of Patent: Apr. 23, 2013

(54) SURGICAL INSTRUMENT HAVING A DIRECTIONAL SWITCHING MECHANISM

(75) Inventors: Frederick E. Shelton, IV, Hillsboro, OH (US); Chad P. Boudreaux, Cincinnati, OH (US); Richard W. Timm, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 11 days.

(21) Appl. No.: 12/939,688

(22) Filed: Nov. 4, 2010

(65) Prior Publication Data

US 2011/0042441 A1  Feb. 24, 2011

Related U.S. Application Data

(62) Division of application No. 11/810,016, filed on Jun. 4, 2007, now Pat. No. 7,832,408.

(51) Int. Cl.
*A61B 17/068* (2006.01)
(52) U.S. Cl.
USPC .................................... 227/178.1; 227/179.1
(58) Field of Classification Search ............... 227/176.1, 227/178.1, 179.1
See application file for complete search history.

(56) References Cited

U.S. PATENT DOCUMENTS

| | | |
|---|---|---|
| 66,052 A | 6/1867 | Smith |
| 662,587 A | 11/1900 | Blake |
| 951,393 A | 3/1910 | Hahn |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,441,096 A | 5/1948 | Happe |
| 2,526,902 A | 10/1950 | Rublee |
| 2,674,149 A | 4/1954 | Benson |
| 2,804,848 A | 9/1957 | O'Farrell et al. |
| 2,808,482 A | 10/1957 | Zanichkowsky et al. |
| 2,853,074 A | 9/1958 | Olson |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Hemant M Desai
*Assistant Examiner* — Gloria R Weeks

(57) ABSTRACT

A surgical instrument including a switching mechanism which allows a surgeon to selectively advance or retract a staple driver, cutting member, and/or other movable member within a staple cartridge. In various embodiments, the surgical instrument can include a handle, a trigger operatively coupled to the handle, a firing drive, and an end effector. In at least one embodiment, the trigger can be configured to slide between a first position in which an operation of the trigger can advance the movable member at a first rate and a second position in which an operation of the trigger can retract the movable member at a second rate.

28 Claims, 32 Drawing Sheets

U.S. PATENT DOCUMENTS

| | | | |
|---|---|---|---|
| 3,032,769 A | 5/1962 | Palmer | |
| 3,075,062 A | 1/1963 | Iaccarino | |
| 3,078,465 A | 2/1963 | Bobrov | |
| 3,166,072 A | 1/1965 | Sullivan, Jr. | |
| 3,266,494 A | 8/1966 | Brownrigg et al. | |
| 3,269,630 A | 8/1966 | Fleischer | |
| 3,357,296 A | 12/1967 | Lefever | |
| 3,490,675 A | 1/1970 | Green et al. | |
| 3,551,987 A | 1/1971 | Wilkinson | |
| 3,598,943 A | 8/1971 | Barrett | |
| 3,643,851 A | 2/1972 | Green et al. | |
| 3,662,939 A | 5/1972 | Bryan | |
| 3,717,294 A | 2/1973 | Green | |
| 3,734,207 A | 5/1973 | Fishbein | |
| 3,740,994 A * | 6/1973 | De Carlo, Jr. | 72/407 |
| 3,744,495 A | 7/1973 | Johnson | |
| 3,746,002 A | 7/1973 | Haller | |
| 3,751,902 A | 8/1973 | Kingsbury et al. | |
| 3,819,100 A * | 6/1974 | Noiles et al. | 227/19 |
| 3,821,919 A | 7/1974 | Knohl | |
| 3,885,491 A | 5/1975 | Curtis | |
| 3,892,228 A | 7/1975 | Mitsui | |
| 3,894,174 A | 7/1975 | Cartun | |
| 3,940,844 A | 3/1976 | Colby et al. | |
| RE28,932 E * | 8/1976 | Noiles et al. | 227/19 |
| 4,060,089 A | 11/1977 | Noiles | |
| 4,129,059 A | 12/1978 | Van Eck | |
| 4,213,562 A | 7/1980 | Garrett et al. | |
| 4,250,436 A | 2/1981 | Weissman | |
| 4,261,244 A | 4/1981 | Becht et al. | |
| 4,272,662 A | 6/1981 | Simpson | |
| 4,275,813 A | 6/1981 | Noiles | |
| 4,289,133 A | 9/1981 | Rothfuss | |
| 4,305,539 A | 12/1981 | Korolkov et al. | |
| 4,317,451 A | 3/1982 | Cerwin et al. | |
| 4,321,002 A | 3/1982 | Froehlich | |
| 4,331,277 A | 5/1982 | Green | |
| 4,340,331 A | 7/1982 | Savino | |
| 4,347,450 A | 8/1982 | Colligan | |
| 4,349,028 A | 9/1982 | Green | |
| 4,353,371 A | 10/1982 | Cosman | |
| 4,379,457 A | 4/1983 | Gravener et al. | |
| 4,380,312 A | 4/1983 | Landrus | |
| 4,383,634 A | 5/1983 | Green | |
| 4,396,139 A | 8/1983 | Hall et al. | |
| 4,402,445 A | 9/1983 | Green | |
| 4,408,692 A | 10/1983 | Sigel et al. | |
| 4,415,112 A | 11/1983 | Green | |
| 4,428,376 A | 1/1984 | Mericle | |
| 4,429,695 A | 2/1984 | Green | |
| 4,434,796 A | 3/1984 | Karapetian et al. | |
| 4,442,964 A | 4/1984 | Becht | |
| 4,451,743 A | 5/1984 | Suzuki et al. | |
| 4,454,887 A | 6/1984 | Krüger | |
| 4,467,805 A | 8/1984 | Fukuda | |
| 4,475,679 A | 10/1984 | Fleury, Jr. | |
| 4,485,816 A | 12/1984 | Krumme | |
| 4,489,875 A | 12/1984 | Crawford et al. | |
| 4,500,024 A | 2/1985 | DiGiovanni et al. | |
| 4,505,273 A | 3/1985 | Braun et al. | |
| 4,505,414 A | 3/1985 | Filipi | |
| 4,506,671 A | 3/1985 | Green | |
| 4,520,817 A | 6/1985 | Green | |
| 4,522,327 A | 6/1985 | Korthoff et al. | |
| 4,526,174 A | 7/1985 | Froehlich | |
| 4,527,724 A | 7/1985 | Chow et al. | |
| 4,530,453 A | 7/1985 | Green | |
| 4,548,202 A | 10/1985 | Duncan | |
| 4,565,189 A | 1/1986 | Mabuchi | |
| 4,566,620 A | 1/1986 | Green et al. | |
| 4,573,469 A | 3/1986 | Golden et al. | |
| 4,573,622 A | 3/1986 | Green et al. | |
| 4,576,167 A | 3/1986 | Noiles et al. | |
| 4,580,712 A | 4/1986 | Green | |
| 4,589,416 A | 5/1986 | Green | |
| 4,591,085 A | 5/1986 | Di Giovanni | |
| 4,604,786 A | 8/1986 | Howie, Jr. | |
| 4,605,001 A | 8/1986 | Rothfuss et al. | |
| 4,606,343 A | 8/1986 | Conta et al. | |
| 4,607,638 A | 8/1986 | Crainich | |
| 4,608,981 A | 9/1986 | Rothfuss et al. | |
| 4,610,250 A | 9/1986 | Green | |
| 4,610,383 A | 9/1986 | Rothfuss et al. | |
| 4,619,262 A | 10/1986 | Taylor | |
| 4,629,107 A | 12/1986 | Fedotov et al. | |
| 4,632,290 A | 12/1986 | Green et al. | |
| 4,633,874 A | 1/1987 | Chow et al. | |
| 4,641,076 A | 2/1987 | Linden | |
| 4,646,722 A | 3/1987 | Silverstein et al. | |
| 4,655,222 A | 4/1987 | Florez et al. | |
| 4,663,874 A | 5/1987 | Sano et al. | |
| 4,664,305 A | 5/1987 | Blake, III et al. | |
| 4,665,916 A | 5/1987 | Green | |
| 4,667,674 A | 5/1987 | Korthoff et al. | |
| 4,671,445 A | 6/1987 | Barker et al. | |
| 4,676,245 A | 6/1987 | Fukuda | |
| 4,693,248 A | 9/1987 | Failla | |
| 4,709,120 A | 11/1987 | Pearson | |
| 4,715,520 A | 12/1987 | Roehr, Jr. et al. | |
| 4,719,917 A | 1/1988 | Barrows et al. | |
| 4,728,020 A | 3/1988 | Green et al. | |
| 4,728,876 A | 3/1988 | Mongeon et al. | |
| 4,729,260 A | 3/1988 | Dudden | |
| 4,741,336 A | 5/1988 | Failla et al. | |
| 4,752,024 A | 6/1988 | Green et al. | |
| 4,754,909 A | 7/1988 | Barker et al. | |
| 4,767,044 A | 8/1988 | Green | |
| 4,777,780 A | 10/1988 | Holzwarth | |
| 4,787,387 A | 11/1988 | Burbank, III et al. | |
| 4,790,225 A | 12/1988 | Moody et al. | |
| 4,805,617 A | 2/1989 | Bedi et al. | |
| 4,805,823 A | 2/1989 | Rothfuss | |
| 4,809,695 A | 3/1989 | Gwathmey et al. | |
| 4,817,847 A | 4/1989 | Redtenbacher et al. | |
| 4,819,853 A | 4/1989 | Green | |
| 4,821,939 A | 4/1989 | Green | |
| 4,827,911 A | 5/1989 | Broadwin et al. | |
| 4,844,068 A | 7/1989 | Arata et al. | |
| 4,869,414 A | 9/1989 | Green et al. | |
| 4,869,415 A | 9/1989 | Fox | |
| 4,880,015 A | 11/1989 | Nierman | |
| 4,890,613 A | 1/1990 | Golden et al. | |
| 4,892,244 A | 1/1990 | Fox et al. | |
| 4,915,100 A | 4/1990 | Green | |
| 4,930,503 A | 6/1990 | Pruitt | |
| 4,932,960 A | 6/1990 | Green et al. | |
| 4,938,408 A | 7/1990 | Bedi et al. | |
| 4,941,623 A | 7/1990 | Pruitt | |
| 4,944,443 A | 7/1990 | Oddsen et al. | |
| 4,955,959 A | 9/1990 | Tompkins et al. | |
| 4,978,049 A | 12/1990 | Green | |
| 4,986,808 A | 1/1991 | Broadwin et al. | |
| 4,988,334 A | 1/1991 | Hornlein et al. | |
| 5,002,553 A | 3/1991 | Shiber | |
| 5,009,661 A | 4/1991 | Michelson | |
| 5,014,899 A | 5/1991 | Presty et al. | |
| 5,015,227 A | 5/1991 | Broadwin et al. | |
| 5,027,834 A | 7/1991 | Pruitt | |
| 5,031,814 A | 7/1991 | Tompkins et al. | |
| 5,040,715 A | 8/1991 | Green et al. | |
| 5,042,707 A | 8/1991 | Taheri | |
| 5,061,269 A | 10/1991 | Muller | |
| 5,062,563 A | 11/1991 | Green et al. | |
| 5,065,929 A | 11/1991 | Schulze et al. | |
| 5,071,052 A | 12/1991 | Rodak et al. | |
| 5,071,430 A | 12/1991 | de Salis et al. | |
| 5,074,454 A | 12/1991 | Peters | |
| 5,080,556 A | 1/1992 | Carreno | |
| 5,083,695 A | 1/1992 | Foslien et al. | |
| 5,084,057 A | 1/1992 | Green et al. | |
| 5,088,979 A | 2/1992 | Filipi et al. | |
| 5,088,997 A | 2/1992 | Delahuerga et al. | |
| 5,094,247 A | 3/1992 | Hernandez et al. | |
| 5,100,420 A | 3/1992 | Green et al. | |
| 5,104,025 A | 4/1992 | Main et al. | |
| 5,106,008 A | 4/1992 | Tompkins et al. | |
| 5,111,987 A | 5/1992 | Moeinzadeh et al. | |

| | | | | | |
|---|---|---|---|---|---|
| 5,116,349 A | 5/1992 | Aranyi | 5,359,231 A | 10/1994 | Flowers et al. |
| 5,129,570 A | 7/1992 | Schulze et al. | D352,780 S | 11/1994 | Glaeser et al. |
| 5,137,198 A | 8/1992 | Nobis et al. | 5,360,428 A | 11/1994 | Hutchinson, Jr. |
| 5,139,513 A | 8/1992 | Segato | 5,364,003 A | 11/1994 | Williamson, IV |
| 5,141,144 A | 8/1992 | Foslien et al. | 5,366,134 A | 11/1994 | Green et al. |
| 5,156,315 A | 10/1992 | Green et al. | 5,366,479 A | 11/1994 | McGarry et al. |
| 5,156,614 A | 10/1992 | Green et al. | 5,370,645 A | 12/1994 | Klicek et al. |
| 5,158,567 A | 10/1992 | Green | 5,372,596 A | 12/1994 | Klicek et al. |
| D330,699 S | 11/1992 | Gill | 5,372,602 A | 12/1994 | Burke |
| 5,163,598 A | 11/1992 | Peters et al. | 5,374,277 A | 12/1994 | Hassler |
| 5,171,247 A | 12/1992 | Hughett et al. | 5,379,933 A | 1/1995 | Green et al. |
| 5,171,249 A | 12/1992 | Stefanchik et al. | 5,381,782 A | 1/1995 | DeLaRama et al. |
| 5,188,111 A | 2/1993 | Yates et al. | 5,382,247 A | 1/1995 | Cimino et al. |
| 5,190,517 A | 3/1993 | Zieve et al. | 5,383,880 A | 1/1995 | Hooven |
| 5,195,968 A | 3/1993 | Lundquist et al. | 5,383,881 A | 1/1995 | Green et al. |
| 5,197,648 A | 3/1993 | Gingold | 5,383,888 A | 1/1995 | Zvenyatsky et al. |
| 5,200,280 A | 4/1993 | Karasa | 5,383,895 A | 1/1995 | Holmes et al. |
| 5,205,459 A | 4/1993 | Brinkerhoff et al. | 5,389,098 A | 2/1995 | Tsuruta et al. |
| 5,207,697 A | 5/1993 | Carusillo et al. | 5,391,180 A | 2/1995 | Tovey et al. |
| 5,209,747 A | 5/1993 | Knoepfler | 5,392,979 A | 2/1995 | Green et al. |
| 5,211,649 A | 5/1993 | Kohler et al. | 5,395,030 A | 3/1995 | Kuramoto et al. |
| 5,217,457 A | 6/1993 | Delahuerga et al. | 5,395,033 A | 3/1995 | Byrne et al. |
| 5,217,478 A | 6/1993 | Rexroth | 5,395,312 A | 3/1995 | Desai |
| 5,219,111 A | 6/1993 | Bilotti et al. | 5,397,046 A | 3/1995 | Savage et al. |
| 5,221,036 A | 6/1993 | Takase | 5,397,324 A | 3/1995 | Carroll et al. |
| 5,221,281 A | 6/1993 | Klicek | 5,403,312 A | 4/1995 | Yates et al. |
| 5,222,963 A | 6/1993 | Brinkerhoff et al. | 5,405,072 A | 4/1995 | Zlock et al. |
| 5,222,975 A | 6/1993 | Crainich | 5,405,344 A | 4/1995 | Williamson et al. |
| 5,222,976 A | 6/1993 | Yoon | 5,407,293 A | 4/1995 | Crainich |
| 5,223,675 A | 6/1993 | Taft | 5,409,498 A | 4/1995 | Braddock et al. |
| 5,234,447 A | 8/1993 | Kaster et al. | 5,411,508 A | 5/1995 | Bessler et al. |
| 5,236,440 A | 8/1993 | Hlavacek | 5,413,267 A | 5/1995 | Solyntjes et al. |
| 5,239,981 A | 8/1993 | Anapliotis | 5,413,268 A | 5/1995 | Green et al. |
| 5,240,163 A | 8/1993 | Stein et al. | 5,413,272 A | 5/1995 | Green et al. |
| 5,242,457 A | 9/1993 | Akopov et al. | 5,415,334 A | 5/1995 | Williamson, IV et al. |
| 5,244,462 A | 9/1993 | Delahuerga et al. | 5,415,335 A | 5/1995 | Knodell, Jr. |
| 5,246,156 A | 9/1993 | Rothfuss et al. | 5,417,361 A | 5/1995 | Williamson, IV |
| 5,246,443 A | 9/1993 | Mai | 5,421,829 A | 6/1995 | Olichney et al. |
| 5,253,793 A | 10/1993 | Green et al. | 5,422,567 A | 6/1995 | Matsunaga |
| 5,258,009 A | 11/1993 | Conners | 5,423,809 A | 6/1995 | Klicek |
| 5,258,012 A | 11/1993 | Luscombe et al. | 5,425,745 A | 6/1995 | Green et al. |
| 5,259,366 A | 11/1993 | Reydel et al. | 5,431,322 A | 7/1995 | Green et al. |
| 5,260,637 A | 11/1993 | Pizzi | 5,431,668 A | 7/1995 | Burbank, III et al. |
| 5,263,629 A | 11/1993 | Trumbull et al. | 5,433,721 A | 7/1995 | Hooven et al. |
| 5,263,973 A | 11/1993 | Cook | 5,438,302 A | 8/1995 | Goble |
| 5,268,622 A | 12/1993 | Philipp | 5,441,193 A | 8/1995 | Gravener |
| 5,271,543 A | 12/1993 | Grant et al. | 5,441,494 A | 8/1995 | Ortiz |
| 5,271,544 A | 12/1993 | Fox et al. | 5,445,304 A | 8/1995 | Plyley et al. |
| RE34,519 E | 1/1994 | Fox et al. | 5,445,644 A | 8/1995 | Pietrafitta et al. |
| 5,275,323 A | 1/1994 | Schulze et al. | 5,447,417 A | 9/1995 | Kuhl et al. |
| 5,275,608 A | 1/1994 | Forman et al. | 5,447,513 A | 9/1995 | Davison et al. |
| 5,281,216 A | 1/1994 | Klicek | 5,449,355 A | 9/1995 | Rhum et al. |
| 5,282,806 A | 2/1994 | Haber et al. | 5,449,365 A | 9/1995 | Green et al. |
| 5,282,829 A | 2/1994 | Hermes | 5,452,836 A * | 9/1995 | Huitema et al. ............ 227/176.1 |
| 5,297,714 A | 3/1994 | Kramer | 5,452,837 A | 9/1995 | Williamson, IV et al. |
| 5,304,204 A | 4/1994 | Bregen | 5,454,827 A | 10/1995 | Aust et al. |
| 5,307,976 A | 5/1994 | Olson et al. | 5,456,401 A | 10/1995 | Green et al. |
| 5,309,927 A | 5/1994 | Welch | 5,458,579 A | 10/1995 | Chodorow et al. |
| 5,312,023 A | 5/1994 | Green et al. | 5,462,215 A | 10/1995 | Viola et al. |
| 5,312,329 A | 5/1994 | Beaty et al. | 5,464,300 A | 11/1995 | Crainich |
| 5,314,424 A | 5/1994 | Nicholas | 5,465,894 A | 11/1995 | Clark et al. |
| 5,318,221 A | 6/1994 | Green et al. | 5,465,895 A * | 11/1995 | Knodel et al. ............. 227/176.1 |
| 5,330,502 A | 7/1994 | Hassler et al. | 5,465,896 A | 11/1995 | Allen et al. |
| 5,332,142 A | 7/1994 | Robinson et al. | 5,466,020 A | 11/1995 | Page et al. |
| 5,333,422 A | 8/1994 | Warren et al. | 5,467,911 A | 11/1995 | Tsuruta et al. |
| 5,334,183 A | 8/1994 | Wuchinich | 5,470,006 A | 11/1995 | Rodak |
| 5,336,232 A | 8/1994 | Green et al. | 5,470,007 A | 11/1995 | Plyley et al. |
| 5,339,799 A | 8/1994 | Kami et al. | 5,472,132 A | 12/1995 | Savage et al. |
| 5,341,724 A | 8/1994 | Vatel | 5,472,442 A | 12/1995 | Klicek |
| 5,341,810 A | 8/1994 | Dardel | 5,473,204 A | 12/1995 | Temple |
| 5,342,395 A | 8/1994 | Jarrett et al. | 5,474,057 A | 12/1995 | Makower et al. |
| 5,342,396 A | 8/1994 | Cook | 5,474,566 A | 12/1995 | Alesi et al. |
| 5,344,060 A | 9/1994 | Gravener et al. | 5,476,206 A | 12/1995 | Green et al. |
| 5,350,400 A | 9/1994 | Esposito et al. | 5,476,479 A | 12/1995 | Green et al. |
| 5,352,235 A | 10/1994 | Koros et al. | 5,478,003 A | 12/1995 | Green et al. |
| 5,352,238 A | 10/1994 | Green et al. | 5,478,354 A | 12/1995 | Tovey et al. |
| 5,354,303 A | 10/1994 | Spaeth et al. | 5,480,089 A | 1/1996 | Blewett |
| 5,356,006 A | 10/1994 | Alpern et al. | 5,480,409 A | 1/1996 | Riza |
| 5,358,510 A | 10/1994 | Luscombe et al. | 5,482,197 A | 1/1996 | Green et al. |

| Patent No. | Date | Inventor(s) |
|---|---|---|
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,527,320 A * | 6/1996 | Carruthers et al. ............ 606/143 |
| 5,529,235 A | 6/1996 | Boiarski et al. |
| D372,086 S | 7/1996 | Grasso et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,543,119 A | 8/1996 | Sutter et al. |
| 5,547,117 A | 8/1996 | Hamblin et al. |
| 5,549,621 A | 8/1996 | Bessler et al. |
| 5,549,628 A | 8/1996 | Cooper et al. |
| 5,549,637 A | 8/1996 | Crainich |
| 5,553,675 A | 9/1996 | Pitzen et al. |
| 5,553,765 A * | 9/1996 | Knodel et al. ............ 227/176.1 |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,571,090 A | 11/1996 | Sherts |
| 5,571,100 A | 11/1996 | Goble et al. |
| 5,571,116 A | 11/1996 | Bolanos et al. |
| 5,573,543 A | 11/1996 | Akopov et al. |
| 5,574,431 A | 11/1996 | McKeown et al. |
| 5,575,789 A | 11/1996 | Bell et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,344 A | 2/1997 | Paterson |
| 5,599,350 A | 2/1997 | Schulze et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,450 A | 3/1997 | Zvenyatsky et al. |
| 5,609,285 A | 3/1997 | Grant et al. |
| 5,611,709 A | 3/1997 | McAnulty |
| 5,613,966 A | 3/1997 | Makower et al. |
| 5,618,294 A | 4/1997 | Aust et al. |
| 5,618,303 A | 4/1997 | Marlow et al. |
| 5,620,289 A | 4/1997 | Curry |
| 5,620,452 A | 4/1997 | Yoon |
| 5,624,452 A | 4/1997 | Yates |
| 5,626,587 A | 5/1997 | Bishop et al. |
| 5,628,446 A | 5/1997 | Geiste et al. |
| 5,628,743 A | 5/1997 | Cimino |
| 5,630,539 A | 5/1997 | Plyley et al. |
| 5,630,540 A | 5/1997 | Blewett |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,281 A | 8/1997 | Heard |
| 5,658,300 A | 8/1997 | Bito et al. |
| 5,662,258 A | 9/1997 | Knodel et al. |
| 5,662,260 A | 9/1997 | Yoon |
| 5,662,662 A | 9/1997 | Bishop et al. |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,693,051 A | 12/1997 | Schulze et al. |
| 5,695,494 A | 12/1997 | Becker |
| 5,695,504 A | 12/1997 | Gifford, III et al. |
| 5,695,524 A | 12/1997 | Kelley et al. |
| 5,697,543 A | 12/1997 | Burdorff |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |

| | | | | | | |
|---|---|---|---|---|---|---|
| 5,704,087 A | 1/1998 | Strub | | 5,820,009 A | 10/1998 | Melling et al. |
| 5,704,534 A | 1/1998 | Huitema et al. | | 5,823,066 A | 10/1998 | Huitema et al. |
| 5,706,997 A * | 1/1998 | Green et al. ............ 227/175.2 | | 5,826,776 A | 10/1998 | Schulze et al. |
| 5,706,998 A | 1/1998 | Plyley et al. | | 5,827,271 A | 10/1998 | Buysse et al. |
| 5,707,392 A | 1/1998 | Kortenbach | | 5,829,662 A | 11/1998 | Allen et al. |
| 5,709,334 A | 1/1998 | Sorrentino et al. | | 5,833,690 A | 11/1998 | Yates et al. |
| 5,709,680 A | 1/1998 | Yates et al. | | 5,833,695 A | 11/1998 | Yoon |
| 5,711,472 A | 1/1998 | Bryan | | 5,833,696 A | 11/1998 | Whitfield et al. |
| 5,713,128 A | 2/1998 | Schrenk et al. | | 5,836,503 A | 11/1998 | Ehrenfels et al. |
| 5,713,505 A | 2/1998 | Huitema | | 5,836,960 A | 11/1998 | Kolesa et al. |
| 5,713,895 A | 2/1998 | Lontine et al. | | 5,839,639 A | 11/1998 | Sauer et al. |
| 5,715,987 A | 2/1998 | Kelley et al. | | 5,843,132 A | 12/1998 | Ilvento |
| 5,715,988 A | 2/1998 | Palmer | | 5,846,254 A | 12/1998 | Schulze et al. |
| 5,716,366 A | 2/1998 | Yates | | 5,849,011 A | 12/1998 | Jones et al. |
| 5,718,359 A | 2/1998 | Palmer et al. | | 5,855,311 A | 1/1999 | Hamblin et al. |
| 5,718,360 A | 2/1998 | Green et al. | | 5,855,583 A | 1/1999 | Wang et al. |
| 5,718,548 A | 2/1998 | Cotellessa | | 5,860,975 A | 1/1999 | Goble et al. |
| 5,720,744 A | 2/1998 | Eggleston et al. | | 5,865,361 A | 2/1999 | Milliman et al. |
| D393,067 S | 3/1998 | Geary et al. | | 5,868,760 A | 2/1999 | McGuckin, Jr. |
| 5,725,536 A | 3/1998 | Oberlin et al. | | 5,871,135 A | 2/1999 | Williamson, IV et al. |
| 5,725,554 A | 3/1998 | Simon et al. | | 5,873,885 A | 2/1999 | Weidenbenner |
| 5,728,121 A | 3/1998 | Bimbo et al. | | 5,876,401 A | 3/1999 | Schulze et al. |
| 5,730,758 A | 3/1998 | Allgeyer | | 5,878,193 A | 3/1999 | Wang et al. |
| 5,732,871 A | 3/1998 | Clark et al. | | 5,878,937 A | 3/1999 | Green et al. |
| 5,732,872 A | 3/1998 | Bolduc et al. | | 5,878,938 A | 3/1999 | Bittner et al. |
| 5,735,445 A | 4/1998 | Vidal et al. | | 5,891,160 A | 4/1999 | Williamson, IV et al. |
| 5,735,848 A | 4/1998 | Yates et al. | | 5,893,506 A | 4/1999 | Powell |
| 5,735,874 A | 4/1998 | Measamer et al. | | 5,894,979 A | 4/1999 | Powell |
| 5,738,474 A | 4/1998 | Blewett | | 5,897,562 A | 4/1999 | Bolanos et al. |
| 5,738,648 A | 4/1998 | Lands et al. | | 5,899,914 A | 5/1999 | Zirps et al. |
| 5,743,456 A | 4/1998 | Jones et al. | | 5,901,895 A | 5/1999 | Heaton et al. |
| 5,747,953 A | 5/1998 | Philipp | | 5,902,312 A | 5/1999 | Frater et al. |
| 5,749,889 A | 5/1998 | Bacich et al. | | 5,904,693 A | 5/1999 | Dicesare et al. |
| 5,749,893 A | 5/1998 | Vidal et al. | | 5,906,625 A | 5/1999 | Bito et al. |
| 5,752,644 A | 5/1998 | Bolanos et al. | | 5,908,402 A | 6/1999 | Blythe |
| 5,752,965 A | 5/1998 | Francis et al. | | 5,908,427 A | 6/1999 | McKean et al. |
| 5,755,717 A | 5/1998 | Yates et al. | | 5,911,353 A | 6/1999 | Bolanos et al. |
| 5,758,814 A | 6/1998 | Gallagher et al. | | 5,915,616 A | 6/1999 | Viola et al. |
| 5,762,255 A | 6/1998 | Chrisman et al. | | 5,918,791 A | 7/1999 | Sorrentino et al. |
| 5,762,256 A | 6/1998 | Mastri et al. | | 5,919,198 A | 7/1999 | Graves, Jr. et al. |
| 5,766,188 A | 6/1998 | Igaki | | 5,928,256 A | 7/1999 | Riza |
| 5,766,205 A | 6/1998 | Zvenyatsky et al. | | 5,931,847 A | 8/1999 | Bittner et al. |
| 5,769,892 A | 6/1998 | Kingwell | | 5,931,853 A | 8/1999 | McEwen et al. |
| 5,772,379 A | 6/1998 | Evensen | | 5,937,951 A * | 8/1999 | Izuchukwu et al. ........ 227/176.1 |
| 5,772,578 A | 6/1998 | Heimberger et al. | | 5,938,667 A | 8/1999 | Peyser et al. |
| 5,772,659 A | 6/1998 | Becker et al. | | 5,941,442 A | 8/1999 | Geiste et al. |
| 5,776,130 A | 7/1998 | Buysse et al. | | 5,944,172 A | 8/1999 | Hannula |
| 5,779,130 A | 7/1998 | Alesi et al. | | 5,944,715 A | 8/1999 | Goble et al. |
| 5,779,131 A | 7/1998 | Knodel et al. | | 5,948,030 A | 9/1999 | Miller et al. |
| 5,779,132 A | 7/1998 | Knodel et al. | | 5,951,552 A | 9/1999 | Long et al. |
| 5,782,396 A | 7/1998 | Mastri et al. | | 5,951,574 A | 9/1999 | Stefanchik et al. |
| 5,782,397 A | 7/1998 | Koukline | | 5,954,259 A | 9/1999 | Viola et al. |
| 5,782,749 A | 7/1998 | Riza | | 5,964,774 A | 10/1999 | McKean et al. |
| 5,782,859 A | 7/1998 | Nicholas et al. | | 5,971,916 A | 10/1999 | Koren |
| 5,784,934 A | 7/1998 | Izumisawa | | 5,988,479 A | 11/1999 | Palmer |
| 5,785,232 A | 7/1998 | Vidal et al. | | 6,003,517 A | 12/1999 | Sheffield et al. |
| 5,787,897 A | 8/1998 | Kieturakis | | 6,004,319 A | 12/1999 | Goble et al. |
| 5,792,135 A | 8/1998 | Madhani et al. | | 6,010,054 A | 1/2000 | Johnson et al. |
| 5,792,165 A | 8/1998 | Klieman et al. | | 6,012,494 A | 1/2000 | Balazs |
| 5,794,834 A | 8/1998 | Hamblin et al. | | 6,013,076 A | 1/2000 | Goble et al. |
| 5,796,188 A | 8/1998 | Bays | | 6,015,406 A | 1/2000 | Goble et al. |
| 5,797,536 A | 8/1998 | Smith et al. | | 6,017,322 A | 1/2000 | Snoke et al. |
| 5,797,537 A * | 8/1998 | Oberlin et al. ............ 227/176.1 | | 6,017,356 A | 1/2000 | Frederick et al. |
| 5,797,538 A | 8/1998 | Heaton et al. | | 6,022,352 A | 2/2000 | Vandewalle |
| 5,797,906 A | 8/1998 | Rhum et al. | | 6,024,741 A | 2/2000 | Williamson, IV et al. |
| 5,797,959 A | 8/1998 | Castro et al. | | 6,024,748 A | 2/2000 | Manzo et al. |
| 5,799,857 A | 9/1998 | Robertson et al. | | 6,027,501 A | 2/2000 | Goble et al. |
| 5,807,378 A | 9/1998 | Jensen et al. | | 6,032,849 A | 3/2000 | Mastri et al. |
| 5,807,393 A | 9/1998 | Williamson, IV et al. | | 6,033,378 A | 3/2000 | Lundquist et al. |
| 5,809,441 A | 9/1998 | McKee | | 6,033,399 A | 3/2000 | Gines |
| 5,810,811 A | 9/1998 | Yates et al. | | 6,033,427 A | 3/2000 | Lee |
| 5,810,855 A | 9/1998 | Rayburn et al. | | 6,039,733 A | 3/2000 | Buysse et al. |
| 5,813,813 A | 9/1998 | Daum et al. | | 6,039,734 A | 3/2000 | Goble |
| 5,814,057 A | 9/1998 | Oi et al. | | 6,045,560 A | 4/2000 | McKean et al. |
| 5,817,084 A | 10/1998 | Jensen | | 6,050,472 A | 4/2000 | Shibata |
| 5,817,091 A | 10/1998 | Nardella et al. | | 6,053,390 A | 4/2000 | Green et al. |
| 5,817,093 A | 10/1998 | Williamson, IV et al. | | 6,056,746 A | 5/2000 | Goble et al. |
| 5,817,109 A | 10/1998 | McGarry et al. | | 6,063,097 A | 5/2000 | Oi et al. |
| 5,817,119 A | 10/1998 | Klieman et al. | | 6,063,098 A | 5/2000 | Houser et al. |

| | | | | | | |
|---|---|---|---|---|---|---|
| 6,068,627 | A | 5/2000 | Orszulak et al. | 6,364,888 B1 | 4/2002 | Niemeyer et al. |
| 6,071,233 | A | 6/2000 | Ishikawa et al. | 6,373,152 B1 | 4/2002 | Wang et al. |
| 6,074,386 | A | 6/2000 | Goble et al. | 6,387,113 B1 | 5/2002 | Hawkins et al. |
| 6,077,286 | A | 6/2000 | Cuschieri et al. | 6,387,114 B2 | 5/2002 | Adams |
| 6,079,606 | A | 6/2000 | Milliman et al. | 6,391,038 B2 | 5/2002 | Vargas et al. |
| 6,082,577 | A | 7/2000 | Coates et al. | 6,398,781 B1 | 6/2002 | Goble et al. |
| 6,083,234 | A | 7/2000 | Nicholas et al. | 6,398,797 B2 | 6/2002 | Bombard et al. |
| 6,083,242 | A | 7/2000 | Cook | 6,406,440 B1 | 6/2002 | Stefanchik |
| 6,086,600 | A | 7/2000 | Kortenbach | 6,409,724 B1 | 6/2002 | Penny et al. |
| 6,090,106 | A | 7/2000 | Goble et al. | H2037 H | 7/2002 | Yates et al. |
| 6,093,186 | A | 7/2000 | Goble | 6,416,486 B1 | 7/2002 | Wampler |
| 6,099,537 | A | 8/2000 | Sugai et al. | 6,416,509 B1 | 7/2002 | Goble et al. |
| 6,099,551 | A | 8/2000 | Gabbay | RE37,814 E | 8/2002 | Allgeyer |
| 6,102,271 | A | 8/2000 | Longo et al. | 6,436,097 B1 | 8/2002 | Nardella |
| 6,109,500 | A | 8/2000 | Alli et al. | 6,436,107 B1 | 8/2002 | Wang et al. |
| 6,117,158 | A | 9/2000 | Measamer et al. | 6,436,122 B1 | 8/2002 | Frank et al. |
| 6,119,913 | A | 9/2000 | Adams et al. | 6,439,446 B1 | 8/2002 | Perry et al. |
| 6,120,433 | A | 9/2000 | Mizuno et al. | 6,440,146 B2 | 8/2002 | Nicholas et al. |
| 6,123,241 | A | 9/2000 | Walter et al. | 6,443,973 B1 | 9/2002 | Whitman |
| H1904 | H | 10/2000 | Yates et al. | 6,450,391 B1 | 9/2002 | Kayan et al. |
| 6,126,058 | A | 10/2000 | Adams et al. | 6,468,275 B1 | 10/2002 | Wampler et al. |
| 6,126,670 | A | 10/2000 | Walker et al. | 6,471,106 B1 | 10/2002 | Reining |
| 6,131,789 | A | 10/2000 | Schulze et al. | 6,482,200 B2 | 11/2002 | Shippert |
| 6,132,368 | A | 10/2000 | Cooper | 6,485,490 B2 | 11/2002 | Wampler et al. |
| 6,139,546 | A | 10/2000 | Koenig et al. | 6,488,196 B1 | 12/2002 | Fenton, Jr. |
| 6,155,473 | A | 12/2000 | Tompkins et al. | 6,488,197 B1 | 12/2002 | Whitman |
| 6,156,056 | A | 12/2000 | Kearns et al. | 6,491,201 B1 | 12/2002 | Whitman |
| 6,159,146 | A | 12/2000 | El Gazayerli | 6,491,690 B1 | 12/2002 | Goble et al. |
| 6,159,200 | A | 12/2000 | Verdura et al. | 6,491,701 B2 | 12/2002 | Tierney et al. |
| 6,162,208 | A | 12/2000 | Hipps | 6,492,785 B1 | 12/2002 | Kasten et al. |
| 6,165,175 | A | 12/2000 | Wampler et al. | 6,494,896 B1 | 12/2002 | D'Alessio et al. |
| 6,165,184 | A | 12/2000 | Verdura et al. | 6,503,257 B2 | 1/2003 | Grant et al. |
| 6,168,605 | B1 | 1/2001 | Measamer et al. | 6,503,259 B2 | 1/2003 | Huxel et al. |
| 6,171,316 | B1 | 1/2001 | Kovac et al. | 6,505,768 B2 | 1/2003 | Whitman |
| 6,171,330 | B1 | 1/2001 | Benchetrit | 6,510,854 B2 | 1/2003 | Goble |
| 6,174,308 | B1 | 1/2001 | Goble et al. | 6,511,468 B1 | 1/2003 | Cragg et al. |
| 6,174,309 | B1 | 1/2001 | Wrublewski et al. | 6,517,535 B2 | 2/2003 | Edwards |
| 6,179,776 | B1 | 1/2001 | Adams et al. | 6,517,565 B1 | 2/2003 | Whitman et al. |
| 6,181,105 | B1 | 1/2001 | Cutolo et al. | 6,517,566 B1 | 2/2003 | Hovland et al. |
| 6,193,129 | B1 | 2/2001 | Bittner et al. | 6,522,101 B2 | 2/2003 | Malackowski |
| 6,197,042 | B1 | 3/2001 | Ginn et al. | 6,543,456 B1 | 4/2003 | Freeman |
| 6,202,914 | B1 | 3/2001 | Geiste et al. | 6,547,786 B1 | 4/2003 | Goble |
| 6,214,028 | B1 | 4/2001 | Yoon et al. | 6,550,546 B2 | 4/2003 | Thurler et al. |
| 6,220,368 | B1 | 4/2001 | Ark et al. | 6,551,333 B2 | 4/2003 | Kuhns et al. |
| 6,223,835 | B1 | 5/2001 | Habedank et al. | 6,554,861 B2 | 4/2003 | Knox et al. |
| 6,228,081 | B1 | 5/2001 | Goble | 6,558,379 B1 | 5/2003 | Batchelor et al. |
| 6,228,084 | B1 | 5/2001 | Kirwan, Jr. | 6,565,560 B1 | 5/2003 | Goble et al. |
| 6,231,565 | B1 | 5/2001 | Tovey et al. | 6,569,085 B2 | 5/2003 | Kortenbach et al. |
| 6,234,178 | B1 | 5/2001 | Goble et al. | 6,569,171 B2 | 5/2003 | DeGuillebon et al. |
| 6,241,139 | B1 | 6/2001 | Milliman et al. | 6,578,751 B2 | 6/2003 | Hartwick |
| 6,241,723 | B1 | 6/2001 | Heim et al. | 6,582,427 B1 | 6/2003 | Goble et al. |
| 6,249,076 | B1 | 6/2001 | Madden et al. | 6,588,643 B2 | 7/2003 | Bolduc et al. |
| 6,250,532 | B1 | 6/2001 | Green et al. | 6,589,164 B1 | 7/2003 | Flaherty |
| 6,258,107 | B1 | 7/2001 | Balázs et al. | 6,592,597 B2 | 7/2003 | Grant et al. |
| 6,261,286 | B1 | 7/2001 | Goble et al. | 6,596,432 B2 | 7/2003 | Kawakami et al. |
| 6,264,086 | B1 | 7/2001 | McGuckin, Jr. | D478,665 S | 8/2003 | Isaacs et al. |
| 6,264,087 | B1 | 7/2001 | Whitman | D478,986 S | 8/2003 | Johnston et al. |
| 6,270,508 | B1 | 8/2001 | Klieman et al. | 6,601,749 B2 | 8/2003 | Sullivan et al. |
| 6,273,897 | B1 | 8/2001 | Dalessandro et al. | 6,602,252 B2 | 8/2003 | Mollenauer |
| 6,277,114 | B1 | 8/2001 | Bullivant et al. | 6,605,078 B2 | 8/2003 | Adams |
| 6,293,942 | B1 | 9/2001 | Goble et al. | 6,605,669 B2 | 8/2003 | Awokola et al. |
| 6,296,640 | B1 | 10/2001 | Wampler et al. | 6,616,686 B2 | 9/2003 | Coleman et al. |
| 6,302,311 | B1 | 10/2001 | Adams et al. | 6,619,529 B2 | 9/2003 | Green et al. |
| 6,306,134 | B1 | 10/2001 | Goble et al. | 6,620,166 B1 | 9/2003 | Wenstrom, Jr. et al. |
| 6,309,403 | B1 | 10/2001 | Minor et al. | 6,629,630 B2 | 10/2003 | Adams |
| 6,315,184 | B1 | 11/2001 | Whitman | 6,629,974 B2 | 10/2003 | Penny et al. |
| 6,320,123 | B1 | 11/2001 | Reimers | 6,629,988 B2 | 10/2003 | Weadock |
| 6,324,339 | B1 | 11/2001 | Hudson et al. | 6,636,412 B2 | 10/2003 | Smith |
| 6,325,799 | B1 | 12/2001 | Goble | 6,638,108 B2 | 10/2003 | Tachi |
| 6,325,810 | B1 | 12/2001 | Hamilton et al. | 6,638,285 B2 | 10/2003 | Gabbay |
| 6,330,965 | B1 | 12/2001 | Milliman et al. | 6,644,532 B2 | 11/2003 | Green et al. |
| 6,331,181 | B1 | 12/2001 | Tierney et al. | 6,648,816 B2 | 11/2003 | Irion et al. |
| 6,331,761 | B1 | 12/2001 | Kumar et al. | D484,243 S | 12/2003 | Ryan et al. |
| 6,334,860 | B1 | 1/2002 | Dorn | D484,595 S | 12/2003 | Ryan et al. |
| 6,336,926 | B1 | 1/2002 | Goble | D484,596 S | 12/2003 | Ryan et al. |
| 6,346,077 | B1 | 2/2002 | Taylor et al. | 6,656,193 B2 | 12/2003 | Grant et al. |
| 6,352,503 | B1 | 3/2002 | Matsui et al. | 6,666,875 B1 | 12/2003 | Sakurai et al. |
| 6,358,224 | B1 | 3/2002 | Tims et al. | 6,669,073 B2 | 12/2003 | Milliman et al. |
| 6,364,877 | B1 | 4/2002 | Goble et al. | 6,671,185 B2 | 12/2003 | Duval |

| | | | |
|---|---|---|---|
| D484,977 S | 1/2004 | Ryan et al. | |
| 6,676,660 B2 | 1/2004 | Wampler et al. | |
| 6,679,410 B2 | 1/2004 | Würsch et al. | |
| 6,681,978 B2 | 1/2004 | Geiste et al. | |
| 6,681,979 B2 | 1/2004 | Whitman | |
| 6,682,527 B2 | 1/2004 | Strul | |
| 6,682,528 B2 | 1/2004 | Frazier et al. | |
| 6,685,727 B2 | 2/2004 | Fisher et al. | |
| 6,692,507 B2 | 2/2004 | Pugsley et al. | |
| 6,695,199 B2 | 2/2004 | Whitman | |
| 6,698,643 B2 | 3/2004 | Whitman | |
| 6,699,235 B2 | 3/2004 | Wallace et al. | |
| 6,704,210 B1 | 3/2004 | Myers | |
| 6,705,503 B1 | 3/2004 | Pedicini et al. | |
| 6,716,223 B2 | 4/2004 | Leopold et al. | |
| 6,716,232 B1 | 4/2004 | Vidal et al. | |
| 6,716,233 B1 | 4/2004 | Whitman | |
| 6,722,552 B2 | 4/2004 | Fenton, Jr. | |
| 6,723,087 B2 | 4/2004 | O'Neill et al. | |
| 6,723,091 B2 | 4/2004 | Goble et al. | |
| 6,726,697 B2 | 4/2004 | Nicholas et al. | |
| 6,740,030 B2 | 5/2004 | Martone et al. | |
| 6,747,121 B2 | 6/2004 | Gogolewski | |
| 6,749,560 B1 | 6/2004 | Konstorum et al. | |
| 6,752,768 B2 | 6/2004 | Burdorff et al. | |
| 6,752,816 B2 | 6/2004 | Culp et al. | |
| 6,755,195 B1 | 6/2004 | Lemke et al. | |
| 6,755,338 B2 | 6/2004 | Hahnen et al. | |
| 6,758,846 B2 | 7/2004 | Goble et al. | |
| 6,761,685 B2 | 7/2004 | Adams et al. | |
| 6,767,352 B2 | 7/2004 | Field et al. | |
| 6,767,356 B2 | 7/2004 | Kanner et al. | |
| 6,769,594 B2 | 8/2004 | Orban, III | |
| 6,773,438 B1 | 8/2004 | Knodel et al. | |
| 6,780,151 B2 | 8/2004 | Grabover et al. | |
| 6,780,180 B1 | 8/2004 | Goble et al. | |
| 6,783,524 B2 | 8/2004 | Anderson et al. | |
| 6,786,382 B1 | 9/2004 | Hoffman | |
| 6,786,864 B2 | 9/2004 | Matsuura et al. | |
| 6,786,896 B1 | 9/2004 | Madhani et al. | |
| 6,790,173 B2 | 9/2004 | Saadat et al. | |
| 6,793,652 B1 | 9/2004 | Whitman et al. | |
| 6,805,273 B2 | 10/2004 | Bilotti et al. | |
| 6,806,808 B1 | 10/2004 | Watters et al. | |
| 6,808,525 B2 | 10/2004 | Latterell et al. | |
| 6,814,741 B2 | 11/2004 | Bowman et al. | |
| 6,817,508 B1 | 11/2004 | Racenet et al. | |
| 6,817,509 B2 | 11/2004 | Geiste et al. | |
| 6,817,974 B2 | 11/2004 | Cooper et al. | |
| 6,821,273 B2 | 11/2004 | Mollenauer | |
| 6,821,284 B2 | 11/2004 | Sturtz et al. | |
| 6,827,725 B2 | 12/2004 | Batchelor et al. | |
| 6,828,902 B2 | 12/2004 | Casden | |
| 6,830,174 B2 | 12/2004 | Hillstead et al. | |
| 6,832,998 B2 | 12/2004 | Goble | |
| 6,834,001 B2 | 12/2004 | Myono | |
| 6,835,199 B2 | 12/2004 | McGuckin, Jr. et al. | |
| 6,843,403 B2 | 1/2005 | Whitman | |
| 6,843,789 B2 | 1/2005 | Goble | |
| 6,846,307 B2 | 1/2005 | Whitman et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| RE38,708 E | 3/2005 | Bolanos et al. | |
| 6,866,178 B2 | 3/2005 | Adams et al. | |
| 6,866,671 B2 | 3/2005 | Tierney et al. | |
| 6,872,214 B2 | 3/2005 | Sonnenschein et al. | |
| 6,874,669 B2 | 4/2005 | Adams et al. | |
| 6,877,647 B2 | 4/2005 | Green et al. | |
| 6,878,106 B1 | 4/2005 | Herrmann | |
| 6,889,116 B2 | 5/2005 | Jinno | |
| 6,893,435 B2 | 5/2005 | Goble | |
| 6,905,057 B2 | 6/2005 | Swayze et al. | |
| 6,905,497 B2 | 6/2005 | Truckai et al. | |
| 6,913,608 B2 | 7/2005 | Liddicoat et al. | |
| 6,913,613 B2 | 7/2005 | Schwarz et al. | |
| 6,923,803 B2 | 8/2005 | Goble | |
| 6,929,641 B2 | 8/2005 | Goble et al. | |
| 6,931,830 B2 | 8/2005 | Liao | |
| 6,936,042 B2 | 8/2005 | Wallace et al. | |
| 6,939,358 B2 | 9/2005 | Palacios et al. | |
| 6,942,662 B2 | 9/2005 | Goble et al. | |
| 6,945,444 B2 | 9/2005 | Gresham et al. | |
| 6,953,138 B1 | 10/2005 | Dworak et al. | |
| 6,953,139 B2 | 10/2005 | Milliman et al. | |
| 6,959,851 B2 | 11/2005 | Heinrich | |
| 6,959,852 B2 * | 11/2005 | Shelton et al. | 227/182.1 |
| 6,960,163 B2 | 11/2005 | Ewers et al. | |
| 6,960,220 B2 | 11/2005 | Marino et al. | |
| 6,964,363 B2 | 11/2005 | Wales et al. | |
| 6,966,907 B2 | 11/2005 | Goble | |
| 6,966,909 B2 | 11/2005 | Marshall et al. | |
| 6,972,199 B2 | 12/2005 | Lebouitz et al. | |
| 6,974,462 B2 | 12/2005 | Sater | |
| 6,978,921 B2 | 12/2005 | Shelton, IV et al. | |
| 6,978,922 B2 | 12/2005 | Bilotti et al. | |
| 6,981,628 B2 | 1/2006 | Wales | |
| 6,981,941 B2 | 1/2006 | Whitman et al. | |
| 6,981,978 B2 | 1/2006 | Gannoe | |
| 6,984,203 B2 | 1/2006 | Tartaglia et al. | |
| 6,984,231 B2 | 1/2006 | Goble et al. | |
| 6,986,451 B1 | 1/2006 | Mastri et al. | |
| 6,988,649 B2 | 1/2006 | Shelton, IV et al. | |
| 6,988,650 B2 | 1/2006 | Schwemberger et al. | |
| 6,990,796 B2 | 1/2006 | Schnipke et al. | |
| 6,997,931 B2 | 2/2006 | Sauer et al. | |
| 7,000,818 B2 | 2/2006 | Shelton, IV et al. | |
| 7,000,819 B2 | 2/2006 | Swayze et al. | |
| 7,001,380 B2 | 2/2006 | Goble | |
| 7,001,408 B2 | 2/2006 | Knodel et al. | |
| 7,008,435 B2 | 3/2006 | Cummins | |
| 7,018,390 B2 | 3/2006 | Turovskiy et al. | |
| 7,025,743 B2 | 4/2006 | Mann et al. | |
| 7,029,435 B2 | 4/2006 | Nakao | |
| 7,032,798 B2 | 4/2006 | Whitman et al. | |
| 7,032,799 B2 | 4/2006 | Viola et al. | |
| 7,033,356 B2 | 4/2006 | Latterell et al. | |
| 7,036,680 B2 | 5/2006 | Flannery | |
| 7,037,344 B2 | 5/2006 | Kagan et al. | |
| 7,044,352 B2 | 5/2006 | Shelton, IV et al. | |
| 7,044,353 B2 | 5/2006 | Mastri et al. | |
| 7,048,687 B1 | 5/2006 | Reuss et al. | |
| 7,052,494 B2 | 5/2006 | Goble et al. | |
| 7,055,730 B2 | 6/2006 | Ehrenfels et al. | |
| 7,055,731 B2 | 6/2006 | Shelton, IV et al. | |
| 7,056,284 B2 | 6/2006 | Martone et al. | |
| 7,056,330 B2 | 6/2006 | Gayton | |
| 7,059,508 B2 | 6/2006 | Shelton, IV et al. | |
| 7,063,712 B2 | 6/2006 | Vargas et al. | |
| 7,066,944 B2 | 6/2006 | Laufer et al. | |
| 7,070,083 B2 | 7/2006 | Jankowski | |
| 7,070,559 B2 | 7/2006 | Adams et al. | |
| 7,071,287 B2 | 7/2006 | Rhine et al. | |
| 7,075,770 B1 | 7/2006 | Smith | |
| 7,077,856 B2 | 7/2006 | Whitman | |
| 7,080,769 B2 | 7/2006 | Vresh et al. | |
| 7,081,114 B2 | 7/2006 | Rashidi | |
| 7,083,073 B2 | 8/2006 | Yoshie et al. | |
| 7,083,075 B2 | 8/2006 | Swayze et al. | |
| 7,083,571 B2 | 8/2006 | Wang et al. | |
| 7,083,615 B2 | 8/2006 | Peterson et al. | |
| 7,087,071 B2 | 8/2006 | Nicholas et al. | |
| 7,090,637 B2 | 8/2006 | Danitz et al. | |
| 7,090,673 B2 | 8/2006 | Dycus et al. | |
| 7,090,684 B2 | 8/2006 | McGuckin, Jr. et al. | |
| 7,094,202 B2 | 8/2006 | Nobis et al. | |
| 7,097,089 B2 | 8/2006 | Marczyk | |
| 7,098,794 B2 | 8/2006 | Lindsay et al. | |
| 7,104,741 B2 | 9/2006 | Krohn | |
| 7,108,695 B2 | 9/2006 | Witt et al. | |
| 7,108,701 B2 | 9/2006 | Evens et al. | |
| 7,108,709 B2 | 9/2006 | Cummins | |
| 7,111,769 B2 | 9/2006 | Wales et al. | |
| 7,112,214 B2 | 9/2006 | Peterson et al. | |
| RE39,358 E | 10/2006 | Goble | |
| 7,114,642 B2 | 10/2006 | Whitman | |
| 7,118,582 B1 | 10/2006 | Wang et al. | |
| 7,121,446 B2 | 10/2006 | Arad et al. | |

| Patent No. | Date | Inventor |
|---|---|---|
| 7,122,028 B2 | 10/2006 | Looper et al. |
| 7,128,253 B2 | 10/2006 | Mastri et al. |
| 7,128,254 B2 * | 10/2006 | Shelton et al. ............. 227/181.1 |
| 7,128,748 B2 | 10/2006 | Mooradian et al. |
| 7,131,445 B2 | 11/2006 | Amoah |
| 7,133,601 B2 | 11/2006 | Phillips et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,179,223 B2 | 2/2007 | Motoki et al. |
| 7,179,267 B2 | 2/2007 | Nolan et al. |
| 7,182,239 B1 | 2/2007 | Myers |
| 7,188,758 B2 | 3/2007 | Viola et al. |
| 7,195,627 B2 | 3/2007 | Amoah et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,208,005 B2 | 4/2007 | Frecker et al. |
| 7,210,609 B2 | 5/2007 | Leiboff et |
| 7,211,081 B2 | 5/2007 | Goble |
| 7,211,084 B2 | 5/2007 | Goble et al. |
| 7,213,736 B2 | 5/2007 | Wales et al. |
| 7,214,224 B2 | 5/2007 | Goble |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,258,262 B2 | 8/2007 | Mastri et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,994 B2 | 10/2007 | Goble |
| 7,282,048 B2 | 10/2007 | Goble et al. |
| 7,295,907 B2 | 11/2007 | Lu et al. |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,556 B2 | 12/2007 | Metzger |
| 7,308,998 B2 | 12/2007 | Mastri et al. |
| 7,324,572 B2 | 1/2008 | Chang |
| 7,328,828 B2 | 2/2008 | Ortiz et al. |
| 7,328,829 B2 * | 2/2008 | Arad et al. ................. 227/176.1 |
| 7,330,004 B2 | 2/2008 | DeJonge et al. |
| 7,334,717 B2 | 2/2008 | Rethy et al. |
| 7,336,184 B2 | 2/2008 | Smith et al. |
| 7,338,513 B2 | 3/2008 | Lee et al. |
| 7,343,920 B2 | 3/2008 | Toby et al. |
| 7,348,763 B1 | 3/2008 | Reinhart et al. |
| 7,351,258 B2 | 4/2008 | Ricotta et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,388,217 B2 | 6/2008 | Buschbeck et al. |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,418,078 B2 | 8/2008 | Blanz et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,455,208 B2 | 11/2008 | Wales et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,473,253 B2 | 1/2009 | Dycus et al. |
| 7,479,608 B2 | 1/2009 | Smith |
| 7,481,347 B2 | 1/2009 | Roy |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,501,198 B2 | 3/2009 | Barlev et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,524,320 B2 | 4/2009 | Tierney et al. |
| 7,530,985 B2 | 5/2009 | Takemoto et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,563,862 B2 | 7/2009 | Sieg et al. |
| 7,566,300 B2 | 7/2009 | Devierre et al. |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,588,175 B2 | 9/2009 | Timm et al. |

| Patent No. | Type | Date | Inventor |
|---|---|---|---|
| 7,588,176 | B2 | 9/2009 | Timm et al. |
| 7,597,229 | B2 | 10/2009 | Boudreaux et al. |
| 7,600,663 | B2 | 10/2009 | Green |
| 7,604,150 | B2 | 10/2009 | Boudreaux |
| 7,604,151 | B2 | 10/2009 | Hess et al. |
| 7,607,557 | B2 | 10/2009 | Shelton, IV et al. |
| 7,611,038 | B2 | 11/2009 | Racenet et al. |
| 7,615,003 | B2 | 11/2009 | Stefanchik et al. |
| 7,624,902 | B2 * | 12/2009 | Marczyk et al. ............ 227/175.1 |
| 7,631,793 | B2 | 12/2009 | Rethy et al. |
| 7,637,409 | B2 | 12/2009 | Marczyk |
| 7,641,092 | B2 | 1/2010 | Kruszynski et al. |
| 7,641,093 | B2 | 1/2010 | Doll et al. |
| 7,644,848 | B2 | 1/2010 | Swayze et al. |
| 7,651,498 | B2 | 1/2010 | Shifrin et al. |
| 7,656,131 | B2 | 2/2010 | Embrey et al. |
| 7,658,311 | B2 | 2/2010 | Boudreaux |
| 7,658,312 | B2 | 2/2010 | Vidal et al. |
| 7,665,646 | B2 | 2/2010 | Prommersberger |
| 7,665,647 | B2 | 2/2010 | Shelton, IV et al. |
| 7,669,746 | B2 | 3/2010 | Shelton, IV |
| 7,669,747 | B2 | 3/2010 | Weisenburgh, II et al. |
| 7,670,334 | B2 | 3/2010 | Hueil et al. |
| 7,673,780 | B2 | 3/2010 | Shelton, IV et al. |
| 7,673,781 | B2 | 3/2010 | Swayze et al. |
| 7,673,782 | B2 | 3/2010 | Hess et al. |
| 7,673,783 | B2 | 3/2010 | Morgan et al. |
| 7,674,255 | B2 | 3/2010 | Braun |
| 7,682,307 | B2 | 3/2010 | Danitz et al. |
| 7,686,826 | B2 | 3/2010 | Lee et al. |
| 7,691,098 | B2 | 4/2010 | Wallace et al. |
| 7,699,204 | B2 | 4/2010 | Viola |
| 7,708,180 | B2 | 5/2010 | Murray et al. |
| 7,708,758 | B2 | 5/2010 | Lee et al. |
| 7,714,239 | B2 | 5/2010 | Smith |
| 7,717,312 | B2 | 5/2010 | Beetel |
| 7,721,930 | B2 | 5/2010 | McKenna et al. |
| 7,721,931 | B2 | 5/2010 | Shelton, IV et al. |
| 7,721,934 | B2 | 5/2010 | Shelton, IV et al. |
| 7,721,936 | B2 | 5/2010 | Shalton, IV et al. |
| 7,722,610 | B2 | 5/2010 | Viola et al. |
| 7,726,537 | B2 | 6/2010 | Olson et al. |
| 7,726,538 | B2 | 6/2010 | Holsten et al. |
| 7,731,072 | B2 | 6/2010 | Timm et al. |
| 7,735,703 | B2 | 6/2010 | Morgan et al. |
| 7,738,971 | B2 | 6/2010 | Swayze et al. |
| 7,740,159 | B2 | 6/2010 | Shelton, IV et al. |
| 7,743,960 | B2 | 6/2010 | Whitman et al. |
| 7,744,627 | B2 | 6/2010 | Orban, III et al. |
| 7,753,245 | B2 | 7/2010 | Boudreaux et al. |
| 7,753,904 | B2 | 7/2010 | Shelton, IV et al. |
| 7,766,209 | B2 | 8/2010 | Baxter, III et al. |
| 7,766,210 | B2 | 8/2010 | Shelton, IV et al. |
| 7,766,821 | B2 | 8/2010 | Brunnen et al. |
| 7,766,894 | B2 | 8/2010 | Weitzner et al. |
| 7,770,775 | B2 | 8/2010 | Shelton, IV et al. |
| 7,771,396 | B2 | 8/2010 | Stefanchik et al. |
| 7,772,720 | B2 | 8/2010 | McGee et al. |
| 7,776,060 | B2 | 8/2010 | Mooradian et al. |
| 7,780,054 | B2 | 8/2010 | Wales |
| 7,780,055 | B2 | 8/2010 | Scirica et al. |
| 7,780,663 | B2 | 8/2010 | Yates et al. |
| 7,780,685 | B2 | 8/2010 | Hunt et al. |
| 7,784,662 | B2 | 8/2010 | Wales et al. |
| 7,793,812 | B2 | 9/2010 | Moore et al. |
| 7,794,475 | B2 | 9/2010 | Hess et al. |
| 7,798,386 | B2 | 9/2010 | Schall et al. |
| 7,799,039 | B2 | 9/2010 | Shelton, IV et al. |
| 7,803,151 | B2 | 9/2010 | Whitman |
| 7,806,891 | B2 | 10/2010 | Nowlin et al. |
| 7,810,692 | B2 | 10/2010 | Hall et al. |
| 7,810,693 | B2 | 10/2010 | Broehl et al. |
| 7,815,565 | B2 | 10/2010 | Stefanchik et al. |
| 7,819,296 | B2 | 10/2010 | Hueil et al. |
| 7,819,297 | B2 | 10/2010 | Doll et al. |
| 7,819,298 | B2 | 10/2010 | Hall et al. |
| 7,819,299 | B2 | 10/2010 | Shelton, IV et al. |
| 7,824,401 | B2 | 11/2010 | Manzo et al. |
| 7,828,794 | B2 | 11/2010 | Sartor |
| 7,828,808 | B2 | 11/2010 | Hinman et al. |
| 7,832,408 | B2 * | 11/2010 | Shelton et al. ................ 128/898 |
| 7,832,611 | B2 | 11/2010 | Boyden et al. |
| 7,832,612 | B2 | 11/2010 | Baxter, III et al. |
| 7,836,400 | B2 | 11/2010 | May et al. |
| 7,837,080 | B2 | 11/2010 | Schwemberger |
| 7,837,081 | B2 | 11/2010 | Holsten et al. |
| 7,845,533 | B2 | 12/2010 | Marczyk et al. |
| 7,845,534 | B2 | 12/2010 | Viola et al. |
| 7,845,537 | B2 | 12/2010 | Shelton, IV et al. |
| 7,846,149 | B2 | 12/2010 | Jankowski |
| 7,857,185 | B2 | 12/2010 | Swayze et al. |
| 7,857,186 | B2 | 12/2010 | Baxter, III et al. |
| 7,861,906 | B2 | 1/2011 | Doll et al. |
| 7,866,527 | B2 | 1/2011 | Hall et al. |
| 7,870,989 | B2 | 1/2011 | Viola et al. |
| 7,887,530 | B2 | 2/2011 | Zemlok et al. |
| 7,905,380 | B2 * | 3/2011 | Shelton et al. ............. 227/178.1 |
| 7,909,191 | B2 | 3/2011 | Baker et al. |
| 7,909,221 | B2 | 3/2011 | Viola et al. |
| 7,914,543 | B2 | 3/2011 | Roth et al. |
| 7,922,063 | B2 | 4/2011 | Zemlok et al. |
| 7,938,307 | B2 | 5/2011 | Bettuchi |
| 7,942,303 | B2 | 5/2011 | Shah |
| 7,942,890 | B2 | 5/2011 | D'Agostino et al. |
| 7,950,560 | B2 | 5/2011 | Zemlok et al. |
| 7,959,050 | B2 | 6/2011 | Smith et al. |
| 7,963,963 | B2 | 6/2011 | Francischelli et al. |
| 7,967,180 | B2 | 6/2011 | Scirica |
| 7,972,298 | B2 | 7/2011 | Wallace et al. |
| 8,002,795 | B2 | 8/2011 | Beetel |
| 8,011,551 | B2 | 9/2011 | Marczyk et al. |
| 8,011,555 | B2 | 9/2011 | Tarinelli et al. |
| 8,028,883 | B2 | 10/2011 | Stopek |
| 8,034,077 | B2 | 10/2011 | Smith et al. |
| 8,038,045 | B2 | 10/2011 | Bettuchi et al. |
| 8,038,046 | B2 | 10/2011 | Smith et al. |
| 8,062,330 | B2 | 11/2011 | Prommersberger et al. |
| D650,074 | S | 12/2011 | Hunt et al. |
| 8,091,756 | B2 | 1/2012 | Viola |
| 8,097,017 | B2 | 1/2012 | Viola |
| 8,108,072 | B2 | 1/2012 | Zhao et al. |
| 8,123,103 | B2 | 2/2012 | Milliman |
| 8,152,041 | B2 | 4/2012 | Kostrzewski |
| 8,157,152 | B2 | 4/2012 | Holsten et al. |
| 8,167,895 | B2 | 5/2012 | D'Agostino et al. |
| 8,211,125 | B2 | 7/2012 | Spivey |
| 8,220,468 | B2 | 7/2012 | Cooper et al. |
| 8,225,799 | B2 | 7/2012 | Bettuchi |
| 8,241,271 | B2 | 8/2012 | Millman et al. |
| 8,245,898 | B2 | 8/2012 | Smith et al. |
| 8,245,901 | B2 | 8/2012 | Stopek |
| 8,256,654 | B2 | 9/2012 | Bettuchi et al. |
| 8,257,391 | B2 | 9/2012 | Orban, III et al. |
| 2002/0022836 | A1 | 2/2002 | Goble et al. |
| 2002/0029036 | A1 | 3/2002 | Goble et al. |
| 2002/0117534 | A1 | 8/2002 | Green et al. |
| 2002/0134811 | A1 | 9/2002 | Napier et al. |
| 2002/0165541 | A1 | 11/2002 | Whitman |
| 2003/0093103 | A1 | 5/2003 | Malackowski et al. |
| 2003/0105478 | A1 | 6/2003 | Whitman et al. |
| 2003/0130677 | A1 | 7/2003 | Whitman et al. |
| 2003/0139741 | A1 | 7/2003 | Goble et al. |
| 2003/0153908 | A1 | 8/2003 | Goble et al. |
| 2003/0195387 | A1 | 10/2003 | Kortenbach et al. |
| 2003/0205029 | A1 | 11/2003 | Chapolini et al. |
| 2003/0216732 | A1 | 11/2003 | Truckai et al. |
| 2003/0220660 | A1 | 11/2003 | Kortenbach et al. |
| 2004/0002726 | A1 | 1/2004 | Nunez et al. |
| 2004/0006335 | A1 | 1/2004 | Garrison |
| 2004/0006340 | A1 | 1/2004 | Latterell et al. |
| 2004/0006372 | A1 | 1/2004 | Racenet et al. |
| 2004/0030333 | A1 | 2/2004 | Goble |
| 2004/0034357 | A1 | 2/2004 | Beane et al. |
| 2004/0034369 | A1 | 2/2004 | Sauer et al. |
| 2004/0044364 | A1 | 3/2004 | DeVries et al. |
| 2004/0068161 | A1 | 4/2004 | Couvillon, Jr. |
| 2004/0068307 | A1 | 4/2004 | Goble |
| 2004/0078037 | A1 | 4/2004 | Batchelor et al. |

| Pub. No. | Date | Inventor |
|---|---|---|
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0101822 A1 | 5/2004 | Wiesner et al. |
| 2004/0108357 A1 | 6/2004 | Milliman et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0222268 A1 | 11/2004 | Bilotti et al. |
| 2004/0230214 A1 | 11/2004 | Donofrio et al. |
| 2004/0232201 A1 | 11/2004 | Wenchell et al. |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0254566 A1 | 12/2004 | Plicchi et al. |
| 2004/0254608 A1 | 12/2004 | Huitema et al. |
| 2004/0267310 A1 | 12/2004 | Racenet et al. |
| 2005/0032511 A1 | 2/2005 | Malone et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0080454 A1 | 4/2005 | Drews et al. |
| 2005/0085693 A1 | 4/2005 | Belson et al. |
| 2005/0090817 A1 | 4/2005 | Phan |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0145675 A1 | 7/2005 | Hartwick et al. |
| 2005/0154258 A1 | 7/2005 | Tartaglia et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0274768 A1 | 12/2005 | Cummins et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0100643 A1 | 5/2006 | Laufer et al. |
| 2006/0108393 A1 | 5/2006 | Heinrich et al. |
| 2006/0111710 A1 | 5/2006 | Goble et al. |
| 2006/0111711 A1 | 5/2006 | Goble |
| 2006/0111723 A1 | 5/2006 | Chapolini et al. |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0173470 A1 | 8/2006 | Oray et al. |
| 2006/0180634 A1 | 8/2006 | Shelton, IV et al. |
| 2006/0183246 A1 | 8/2006 | Wiesner et al. |
| 2006/0200123 A1 | 9/2006 | Ryan |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0245971 A1 | 11/2006 | Burns et al. |
| 2006/0258904 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2006/0291981 A1 | 12/2006 | Viola et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0034668 A1 | 2/2007 | Holsten et al. |
| 2007/0055219 A1 | 3/2007 | Whitman et al. |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0135803 A1 | 6/2007 | Belson |
| 2007/0158358 A1 | 7/2007 | Mason, II et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0181632 A1 | 8/2007 | Milliman |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0203510 A1 | 8/2007 | Bettuchi |
| 2007/0213750 A1 | 9/2007 | Weadock |
| 2007/0221700 A1 | 9/2007 | Ortiz et al. |
| 2007/0221701 A1 | 9/2007 | Ortiz et al. |

| Publication No. | Date | Inventor |
|---|---|---|
| 2007/0225562 A1 | 9/2007 | Spivey et al. |
| 2007/0246505 A1 | 10/2007 | Pace-Floridia et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0288044 A1 | 12/2007 | Jinno et al. |
| 2007/0295780 A1 | 12/2007 | Shelton et al. |
| 2007/0299427 A1 | 12/2007 | Yeung et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082114 A1 | 4/2008 | McKenna et al. |
| 2008/0082115 A1 | 4/2008 | Morgan et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0114385 A1 | 5/2008 | Byrum et al. |
| 2008/0129253 A1 | 6/2008 | Shiue et al. |
| 2008/0140115 A1 | 6/2008 | Stopek |
| 2008/0167522 A1 | 7/2008 | Giordano et al. |
| 2008/0167644 A1 | 7/2008 | Shelton et al. |
| 2008/0167671 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0197167 A1 | 8/2008 | Viola et al. |
| 2008/0200835 A1 | 8/2008 | Monson et al. |
| 2008/0210738 A1 | 9/2008 | Shelton et al. |
| 2008/0228029 A1 | 9/2008 | Mikkaichi et al. |
| 2008/0237296 A1 | 10/2008 | Boudreaux et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0262654 A1 | 10/2008 | Omori et al. |
| 2008/0283570 A1 | 11/2008 | Boyden et al. |
| 2008/0287944 A1 | 11/2008 | Pearson et al. |
| 2008/0290134 A1 | 11/2008 | Bettuchi et al. |
| 2008/0296346 A1 | 12/2008 | Shelton, IV et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314954 A1* | 12/2008 | Boudreaux ............... 227/175.1 |
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012534 A1 | 1/2009 | Madhani et al. |
| 2009/0012556 A1 | 1/2009 | Boudreaux et al. |
| 2009/0020958 A1 | 1/2009 | Soul |
| 2009/0054908 A1 | 2/2009 | Zand et al. |
| 2009/0057369 A1 | 3/2009 | Smith et al. |
| 2009/0076534 A1 | 3/2009 | Shelton, IV et al. |
| 2009/0090763 A1 | 4/2009 | Zemlok et al. |
| 2009/0093728 A1 | 4/2009 | Hyde et al. |
| 2009/0108048 A1 | 4/2009 | Zemlok et al. |
| 2009/0114701 A1 | 5/2009 | Zemlok et al. |
| 2009/0143805 A1 | 6/2009 | Palmer et al. |
| 2009/0149871 A9 | 6/2009 | Kagan et al. |
| 2009/0157067 A1 | 6/2009 | Kane et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0213685 A1 | 8/2009 | Mak et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2009/0292283 A1 | 11/2009 | Odom |
| 2009/0308907 A1 | 12/2009 | Nalagatla et al. |
| 2010/0001036 A1 | 1/2010 | Marczyk et al. |
| 2010/0012704 A1 | 1/2010 | Racenet et al. |
| 2010/0023024 A1 | 1/2010 | Zeiner et al. |
| 2010/0032470 A1 | 2/2010 | Hess et al. |
| 2010/0049084 A1 | 2/2010 | Nock et al. |
| 2010/0065605 A1 | 3/2010 | Shelton, IV et al. |
| 2010/0069942 A1 | 3/2010 | Shelton, IV |
| 2010/0072252 A1 | 3/2010 | Baxter, III et al. |
| 2010/0072254 A1 | 3/2010 | Aranyi et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0096431 A1 | 4/2010 | Smith et al. |
| 2010/0096435 A1 | 4/2010 | Fuchs et al. |
| 2010/0108740 A1 | 5/2010 | Pastorelli et al. |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0145146 A1 | 6/2010 | Melder |
| 2010/0163598 A1 | 7/2010 | Belzer |
| 2010/0179382 A1 | 7/2010 | Shelton, IV et al. |
| 2010/0181364 A1 | 7/2010 | Shelton, IV et al. |
| 2010/0186219 A1 | 7/2010 | Smith |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0230465 A1 | 9/2010 | Smith et al. |
| 2010/0237132 A1 | 9/2010 | Measamer et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0258611 A1 | 10/2010 | Smith et al. |
| 2010/0264193 A1 | 10/2010 | Huang et al. |

| | | | | | | |
|---|---|---|---|---|---|---|
| 2010/0264194 A1 | 10/2010 | Huang et al. | | 2012/0029544 A1 | 2/2012 | Shelton, IV et al. |
| 2010/0276471 A1 | 11/2010 | Whitman | | 2012/0029547 A1 | 2/2012 | Shelton, IV et al. |
| 2010/0294827 A1 | 11/2010 | Boyden et al. | | 2012/0046692 A1 | 2/2012 | Smith et al. |
| 2010/0294829 A1 | 11/2010 | Giordano et al. | | 2012/0061448 A1 | 3/2012 | Zingman |
| 2010/0301095 A1 | 12/2010 | Shelton, IV et al. | | 2012/0071711 A1 | 3/2012 | Shelton, IV et al. |
| 2010/0301096 A1 | 12/2010 | Moore et al. | | 2012/0071866 A1 | 3/2012 | Kerr et al. |
| 2010/0305552 A1 | 12/2010 | Shelton, IV et al. | | 2012/0074196 A1 | 3/2012 | Shelton, IV et al. |
| 2010/0308100 A1 | 12/2010 | Boudreaux | | 2012/0074198 A1 | 3/2012 | Huitema et al. |
| 2010/0312261 A1 | 12/2010 | Suzuki et al. | | 2012/0074200 A1 | 3/2012 | Schmid et al. |
| 2011/0006099 A1 | 1/2011 | Hall et al. | | 2012/0074201 A1 | 3/2012 | Baxter, III et al. |
| 2011/0006101 A1 | 1/2011 | Hall et al. | | 2012/0080332 A1 | 4/2012 | Shelton, IV et al. |
| 2011/0006103 A1 | 1/2011 | Laurent et al. | | 2012/0080333 A1 | 4/2012 | Woodard, Jr. et al. |
| 2011/0011914 A1 | 1/2011 | Baxter, III et al. | | 2012/0080334 A1 | 4/2012 | Shelton, IV et al. |
| 2011/0011915 A1 | 1/2011 | Shelton, IV | | 2012/0080335 A1 | 4/2012 | Shelton, IV et al. |
| 2011/0017801 A1 | 1/2011 | Zemlok et al. | | 2012/0080336 A1 | 4/2012 | Shelton, IV et al. |
| 2011/0022032 A1 | 1/2011 | Zemlok et al. | | 2012/0080337 A1 | 4/2012 | Shelton, IV et al. |
| 2011/0024477 A1 | 2/2011 | Hall | | 2012/0080338 A1 | 4/2012 | Shelton, IV et al. |
| 2011/0024478 A1 | 2/2011 | Shelton, IV | | 2012/0080339 A1 | 4/2012 | Shelton, IV et al. |
| 2011/0024479 A1 | 2/2011 | Swensgard et al. | | 2012/0080340 A1 | 4/2012 | Shelton, IV et al. |
| 2011/0036887 A1 | 2/2011 | Zemlok et al. | | 2012/0080344 A1 | 4/2012 | Shelton, IV |
| 2011/0060363 A1 | 3/2011 | Hess et al. | | 2012/0080345 A1 | 4/2012 | Morgan et al. |
| 2011/0062212 A1 | 3/2011 | Shelton, Iv et al. | | 2012/0080475 A1 | 4/2012 | Smith et al. |
| 2011/0068145 A1 | 3/2011 | Bedi et al. | | 2012/0080477 A1 | 4/2012 | Leimbach et al. |
| 2011/0068148 A1 | 3/2011 | Hall et al. | | 2012/0080478 A1 | 4/2012 | Morgan et al. |
| 2011/0084112 A1 | 4/2011 | Kostrzewski | | 2012/0080479 A1 | 4/2012 | Shelton, IV |
| 2011/0084113 A1 | 4/2011 | Bedi et al. | | 2012/0080480 A1 | 4/2012 | Woodard, Jr. et al. |
| 2011/0084115 A1 | 4/2011 | Bedi et al. | | 2012/0080481 A1 | 4/2012 | Widenhouse et al. |
| 2011/0087276 A1 | 4/2011 | Bedi et al. | | 2012/0080482 A1 | 4/2012 | Schall et al. |
| 2011/0087279 A1 | 4/2011 | Shah et al. | | 2012/0080483 A1 | 4/2012 | Riestenberg et al. |
| 2011/0095068 A1 | 4/2011 | Patel | | 2012/0080484 A1 | 4/2012 | Morgan et al. |
| 2011/0101065 A1 | 5/2011 | Milliman | | 2012/0080485 A1 | 4/2012 | Woodard, Jr. et al. |
| 2011/0114697 A1 | 5/2011 | Baxter, III et al. | | 2012/0080486 A1 | 4/2012 | Woodard, Jr. et al. |
| 2011/0114698 A1 | 5/2011 | Baxter, III et al. | | 2012/0080487 A1 | 4/2012 | Woodard, Jr. et al. |
| 2011/0114699 A1 | 5/2011 | Baxter, III et al. | | 2012/0080488 A1 | 4/2012 | Shelton, IV et al. |
| 2011/0114700 A1 | 5/2011 | Baxter, III et al. | | 2012/0080489 A1 | 4/2012 | Shelton, IV et al. |
| 2011/0118761 A1 | 5/2011 | Baxter, III et al. | | 2012/0080490 A1 | 4/2012 | Shelton, IV et al. |
| 2011/0121051 A1 | 5/2011 | Shelton, IV et al. | | 2012/0080491 A1 | 4/2012 | Shelton, IV et al. |
| 2011/0121052 A1 | 5/2011 | Shelton, IV et al. | | 2012/0080493 A1 | 4/2012 | Shelton, IV et al. |
| 2011/0125176 A1 | 5/2011 | Yates et al. | | 2012/0080496 A1 | 4/2012 | Schall et al. |
| 2011/0125177 A1 | 5/2011 | Yates et al. | | 2012/0080498 A1 | 4/2012 | Shelton, IV et al. |
| 2011/0132962 A1 | 6/2011 | Hall et al. | | 2012/0080499 A1 | 4/2012 | Schall et al. |
| 2011/0132963 A1 | 6/2011 | Giordano et al. | | 2012/0080500 A1 | 4/2012 | Morgan et al. |
| 2011/0132964 A1 | 6/2011 | Weisenburgh, II et al. | | 2012/0080501 A1 | 4/2012 | Morgan et al. |
| 2011/0132965 A1 | 6/2011 | Moore et al. | | 2012/0080502 A1 | 4/2012 | Morgan et al. |
| 2011/0139852 A1 | 6/2011 | Zingman | | 2012/0080503 A1 | 4/2012 | Woodard, Jr. et al. |
| 2011/0144430 A1 | 6/2011 | Spivey et al. | | 2012/0083833 A1 | 4/2012 | Shelton, IV et al. |
| 2011/0147433 A1 | 6/2011 | Shelton, IV et al. | | 2012/0083834 A1 | 4/2012 | Shelton, IV et al. |
| 2011/0147434 A1 | 6/2011 | Hueil et al. | | 2012/0083835 A1 | 4/2012 | Shelton, IV et al. |
| 2011/0155780 A1 | 6/2011 | Boudreaux | | 2012/0083836 A1 | 4/2012 | Shelton, IV et al. |
| 2011/0155781 A1 | 6/2011 | Swensgard et al. | | 2012/0132450 A1 | 5/2012 | Timm et al. |
| 2011/0155785 A1 | 6/2011 | Laurent et al. | | 2012/0138660 A1 | 6/2012 | Shelton, IV |
| 2011/0155787 A1 | 6/2011 | Baxter, III et al. | | 2012/0160721 A1 | 6/2012 | Shelton, IV et al. |
| 2011/0163147 A1 | 7/2011 | Laurent et al. | | 2012/0175399 A1 | 7/2012 | Shelton et al. |
| 2011/0174860 A1 | 7/2011 | Shelton, IV et al. | | 2012/0187179 A1 | 7/2012 | Gleiman |
| 2011/0174863 A1 | 7/2011 | Shelton, IV et al. | | 2012/0199630 A1 | 8/2012 | Shelton, IV et al. |
| 2011/0178536 A1 | 7/2011 | Kostrzewski | | 2012/0199631 A1 | 8/2012 | Shelton, IV et al. |
| 2011/0192882 A1 | 8/2011 | Hess et al. | | 2012/0199632 A1 | 8/2012 | Spivey et al. |
| 2011/0210156 A1 | 9/2011 | Smith et al. | | 2012/0199633 A1 | 8/2012 | Shelton, IV et al. |
| 2011/0226837 A1 | 9/2011 | Baxter, III et al. | | 2012/0203247 A1 | 8/2012 | Shelton, IV et al. |
| 2011/0233258 A1 | 9/2011 | Boudreaux | | 2012/0205421 A1 | 8/2012 | Shelton, IV |
| 2011/0253766 A1 | 10/2011 | Baxter, III et al. | | 2012/0211546 A1 | 8/2012 | Shelton, IV |
| 2011/0275901 A1 | 11/2011 | Shelton, IV | | 2012/0234890 A1 | 9/2012 | Aronhalt et al. |
| 2011/0276083 A1 | 11/2011 | Shelton, IV et al. | | 2012/0234891 A1 | 9/2012 | Aronhalt et al. |
| 2011/0288573 A1 | 11/2011 | Yates et al. | | 2012/0234892 A1 | 9/2012 | Aronhalt et al. |
| 2011/0290851 A1 | 12/2011 | Shelton, IV | | 2012/0234893 A1 | 9/2012 | Schuckmann et al. |
| 2011/0290853 A1 | 12/2011 | Shelton, IV et al. | | 2012/0234895 A1 | 9/2012 | O'Connor et al. |
| 2011/0290854 A1 | 12/2011 | Timm et al. | | 2012/0234896 A1 | 9/2012 | Ellerhorst et al. |
| 2011/0290855 A1 | 12/2011 | Moore et al. | | 2012/0234897 A1 | 9/2012 | Shelton, IV et al. |
| 2011/0290856 A1 | 12/2011 | Shelton, IV et al. | | 2012/0234898 A1 | 9/2012 | Shelton, IV et al. |
| 2011/0290857 A1 | 12/2011 | Shelton, IV et al. | | 2012/0234899 A1 | 9/2012 | Scheib et al. |
| 2011/0295242 A1 | 12/2011 | Spivey et al. | | 2012/0234900 A1 | 9/2012 | Swayze |
| 2011/0295269 A1 | 12/2011 | Swensgard et al. | | 2012/0238823 A1 | 9/2012 | Hagerty et al. |
| 2011/0295270 A1 | 12/2011 | Giordano et al. | | 2012/0238824 A1 | 9/2012 | Widenhouse et al. |
| 2011/0295295 A1 | 12/2011 | Shelton, IV et al. | | 2012/0238826 A1 | 9/2012 | Yoo et al. |
| 2012/0022523 A1 | 1/2012 | Smith et al. | | 2012/0238829 A1 | 9/2012 | Shelton, IV et al. |
| 2012/0024934 A1 | 2/2012 | Shelton, IV et al. | | 2012/0239009 A1 | 9/2012 | Mollere et al. |
| 2012/0024935 A1 | 2/2012 | Shelton, IV et al. | | 2012/0239010 A1 | 9/2012 | Shelton, IV et al. |
| 2012/0024936 A1 | 2/2012 | Baxter, III et al. | | 2012/0239012 A1 | 9/2012 | Laurent et al. |
| 2012/0029272 A1 | 2/2012 | Shelton, IV et al. | | 2012/0239075 A1 | 9/2012 | Widenhouse et al. |

| | | | |
|---|---|---|---|
| 2012/0239082 A1 | 9/2012 | Shelton, IV et al. | |
| 2012/0241491 A1 | 9/2012 | Aldridge et al. | |
| 2012/0241492 A1 | 9/2012 | Shelton, IV et al. | |
| 2012/0241493 A1 | 9/2012 | Baxter, III et al. | |
| 2012/0241496 A1 | 9/2012 | Mandakolathur et al. | |
| 2012/0241497 A1 | 9/2012 | Mandakolathur et al. | |
| 2012/0241498 A1 | 9/2012 | Gonzalez et al. | |
| 2012/0241499 A1 | 9/2012 | Baxter, III et al. | |
| 2012/0241500 A1 | 9/2012 | Timmer et al. | |
| 2012/0241501 A1 | 9/2012 | Swayze et al. | |
| 2012/0241502 A1 | 9/2012 | Aldridge et al. | |
| 2012/0241503 A1 | 9/2012 | Baxter, III et al. | |
| 2012/0241505 A1 | 9/2012 | Alexander, III et al. | |
| 2012/0248169 A1 | 10/2012 | Widenhouse et al. | |
| 2012/0253298 A1 | 10/2012 | Henderson et al. | |
| 2012/0265230 A1 | 10/2012 | Yates et al. | |

FOREIGN PATENT DOCUMENTS

| | | |
|---|---|---|
| CA | 2514274 A1 | 1/2006 |
| CN | 1634601 A | 7/2005 |
| CN | 1868411 A | 11/2006 |
| CN | 1915180 A | 2/2007 |
| CN | 101095621 A | 1/2008 |
| DE | 273689 C | 5/1914 |
| DE | 1775926 A | 1/1972 |
| DE | 3036217 A1 | 4/1982 |
| DE | 3210466 A1 | 9/1983 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0387980 B1 | 10/1985 |
| EP | 0033548 B1 | 5/1986 |
| EP | 0276104 A2 | 7/1988 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0598618 B1 | 9/1996 |
| EP | 0709618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |

| | | | | | | |
|---|---|---|---|---|---|---|
| EP | 0754437 | B2 | 12/2004 | EP | 1693008 B1 | 12/2008 |
| EP | 1025807 | B1 | 12/2004 | EP | 1759640 B1 | 12/2008 |
| EP | 1001710 | B1 | 1/2005 | EP | 2000102 A2 | 12/2008 |
| EP | 1520521 | A1 | 4/2005 | EP | 2008595 A2 | 12/2008 |
| EP | 1520523 | A1 | 4/2005 | EP | 1736104 B1 | 3/2009 |
| EP | 1520525 | A1 | 4/2005 | EP | 1749486 B1 | 3/2009 |
| EP | 1522264 | A1 | 4/2005 | EP | 2039316 A2 | 3/2009 |
| EP | 1523942 | A2 | 4/2005 | EP | 1721576 B1 | 4/2009 |
| EP | 1550408 | A1 | 7/2005 | EP | 1733686 B1 | 4/2009 |
| EP | 1557129 | A1 | 7/2005 | EP | 2044890 A1 | 4/2009 |
| EP | 1064883 | B1 | 8/2005 | EP | 1550413 B1 | 6/2009 |
| EP | 1067876 | B1 | 8/2005 | EP | 1745748 B1 | 8/2009 |
| EP | 0870473 | B1 | 9/2005 | EP | 2090237 A1 | 8/2009 |
| EP | 1157666 | B1 | 9/2005 | EP | 2090256 A2 | 8/2009 |
| EP | 0880338 | B1 | 10/2005 | EP | 2095777 A2 | 9/2009 |
| EP | 1158917 | B1 | 11/2005 | EP | 2110082 A1 | 10/2009 |
| EP | 1344498 | B1 | 11/2005 | EP | 1813208 B1 | 11/2009 |
| EP | 1330989 | B1 | 12/2005 | EP | 2116195 A1 | 11/2009 |
| EP | 0771176 | B2 | 1/2006 | EP | 1607050 B1 | 12/2009 |
| EP | 1621138 | A2 | 2/2006 | EP | 1815804 B1 | 12/2009 |
| EP | 1621139 | A2 | 2/2006 | EP | 1566150 B1 | 4/2010 |
| EP | 1621141 | A2 | 2/2006 | EP | 1813206 B1 | 4/2010 |
| EP | 1621145 | A2 | 2/2006 | EP | 1769754 B1 | 6/2010 |
| EP | 1621151 | A2 | 2/2006 | EP | 1535565 B1 | 10/2010 |
| EP | 1034746 | B1 | 3/2006 | EP | 1702570 B1 | 10/2010 |
| EP | 1632191 | A2 | 3/2006 | EP | 1785098 B1 | 10/2010 |
| EP | 1065961 | B1 | 5/2006 | EP | 1627605 B1 | 12/2010 |
| EP | 1082944 | B1 | 5/2006 | EP | 1813205 B1 | 6/2011 |
| EP | 1652481 | A2 | 5/2006 | EP | 1785102 B1 | 1/2012 |
| EP | 1382303 | B1 | 6/2006 | FR | 999646 A | 2/1952 |
| EP | 1253866 | B1 | 7/2006 | FR | 1112936 A | 3/1956 |
| EP | 1032318 | B1 | 8/2006 | FR | 2598905 A1 | 11/1987 |
| EP | 1045672 | B1 | 8/2006 | FR | 2765794 A | 1/1999 |
| EP | 1617768 | B1 | 8/2006 | GB | 939929 A | 10/1963 |
| EP | 1693015 | A2 | 8/2006 | GB | 1210522 A | 10/1970 |
| EP | 1400214 | B1 | 9/2006 | GB | 1217159 A | 12/1970 |
| EP | 1702567 | A2 | 9/2006 | GB | 1339394 A | 12/1973 |
| EP | 1129665 | B1 | 11/2006 | GB | 2109241 A | 6/1983 |
| EP | 1400206 | B1 | 11/2006 | GB | 2272159 A | 5/1994 |
| EP | 1721568 | A1 | 11/2006 | GB | 2284242 A | 5/1995 |
| EP | 1256317 | B1 | 12/2006 | GB | 2336214 A | 10/1999 |
| EP | 1285633 | B1 | 12/2006 | GB | 2425903 A | 11/2006 |
| EP | 1728473 | A1 | 12/2006 | JP | S 58500053 A | 1/1983 |
| EP | 1728475 | A2 | 12/2006 | JP | 61-98249 A | 5/1986 |
| EP | 1479346 | B1 | 1/2007 | JP | 63-203149 | 8/1988 |
| EP | 1484024 | B1 | 1/2007 | JP | 3-12126 A | 1/1991 |
| EP | 1754445 | A2 | 2/2007 | JP | 5-212039 A | 8/1993 |
| EP | 1759812 | A1 | 3/2007 | JP | 6007357 A | 1/1994 |
| EP | 1767163 | A1 | 3/2007 | JP | 7051273 A | 2/1995 |
| EP | 1769756 | A1 | 4/2007 | JP | 8033641 A | 2/1996 |
| EP | 1769758 | A1 | 4/2007 | JP | 8229050 A | 9/1996 |
| EP | 1581128 | B1 | 5/2007 | JP | 2000033071 A | 2/2000 |
| EP | 1785097 | A2 | 5/2007 | JP | 2000171730 A | 6/2000 |
| EP | 1790293 | A2 | 5/2007 | JP | 2000287987 A | 10/2000 |
| EP | 1800610 | A1 | 6/2007 | JP | 2000325303 A | 11/2000 |
| EP | 1300117 | B1 | 8/2007 | JP | 2001-514541 A | 9/2001 |
| EP | 1813199 | A1 | 8/2007 | JP | 2001286477 A | 10/2001 |
| EP | 1813201 | A1 | 8/2007 | JP | 2002143078 A | 5/2002 |
| EP | 1813203 | A2 | 8/2007 | JP | 2002369820 A | 12/2002 |
| EP | 1813207 | A1 | 8/2007 | JP | 2004-344663 | 12/2004 |
| EP | 1813209 | A1 | 8/2007 | JP | 2005-028149 A | 2/2005 |
| EP | 1487359 | B1 | 10/2007 | JP | 2005505322 T | 2/2005 |
| EP | 1599146 | B1 | 10/2007 | JP | 2005103293 A | 4/2005 |
| EP | 1839596 | A1 | 10/2007 | JP | 2005131163 A | 5/2005 |
| EP | 2110083 | A2 | 10/2007 | JP | 2005131164 A | 5/2005 |
| EP | 1857057 | A2 | 11/2007 | JP | 2005131173 A | 5/2005 |
| EP | 1402821 | B1 | 12/2007 | JP | 2005131211 A | 5/2005 |
| EP | 1872727 | A1 | 1/2008 | JP | 2005131212 A | 5/2005 |
| EP | 1897502 | A1 | 3/2008 | JP | 2005137423 A | 6/2005 |
| EP | 1330201 | B1 | 6/2008 | JP | 2005152416 A | 6/2005 |
| EP | 1702568 | B1 | 7/2008 | JP | 2005-523105 A | 8/2005 |
| EP | 1943957 | A2 | 7/2008 | JP | 2005524474 A | 8/2005 |
| EP | 1943964 | A1 | 7/2008 | JP | 2006-281405 A | 10/2006 |
| EP | 1943976 | A2 | 7/2008 | RU | 2008830 C1 | 3/1994 |
| EP | 1593337 | B1 | 8/2008 | RU | 2187249 C2 | 8/2002 |
| EP | 1970014 | A1 | 9/2008 | RU | 2225170 C2 | 3/2004 |
| EP | 1980213 | A2 | 10/2008 | SU | 189517 A | 1/1967 |
| EP | 1759645 | B1 | 11/2008 | SU | 328636 A | 9/1972 |
| EP | 1990014 | A2 | 11/2008 | SU | 886900 A1 | 12/1981 |

| | | | | | | |
|---|---|---|---|---|---|---|
| SU | 1009439 | A | 4/1983 | WO | WO 99/23933 A2 | 5/1999 |
| SU | 1333319 | A2 | 8/1987 | WO | WO 99/23959 A1 | 5/1999 |
| SU | 1377053 | A1 | 2/1988 | WO | WO 99/25261 A1 | 5/1999 |
| SU | 1561964 | A1 | 5/1990 | WO | WO 99/29244 A1 | 6/1999 |
| SU | 1722476 | A1 | 3/1992 | WO | WO 99/34744 A1 | 7/1999 |
| WO | WO 82/02824 | A1 | 9/1982 | WO | WO 99/45849 A1 | 9/1999 |
| WO | WO 91/15157 | A1 | 10/1991 | WO | WO 99/48430 A1 | 9/1999 |
| WO | WO 92/20295 | A1 | 11/1992 | WO | WO 99/51158 A1 | 10/1999 |
| WO | WO 92/21300 | A1 | 12/1992 | WO | WO 00/24322 A1 | 5/2000 |
| WO | WO 93/08755 | A1 | 5/1993 | WO | WO 00/24330 A1 | 5/2000 |
| WO | WO 93/13718 | A1 | 7/1993 | WO | WO 00/41636 A1 | 7/2000 |
| WO | WO 93/14690 | A1 | 8/1993 | WO | WO 00/48506 A1 | 8/2000 |
| WO | WO 93/15648 | A1 | 8/1993 | WO | WO 00/53112 A2 | 9/2000 |
| WO | WO 93/15850 | A1 | 8/1993 | WO | WO 00/54653 A1 | 9/2000 |
| WO | WO 93/19681 | A1 | 10/1993 | WO | WO 00/57796 A1 | 10/2000 |
| WO | WO 94/00060 | A1 | 1/1994 | WO | WO 00/64365 A1 | 11/2000 |
| WO | WO 94/11057 | A1 | 5/1994 | WO | WO 00/72762 A1 | 12/2000 |
| WO | WO 94/12108 | A1 | 6/1994 | WO | WO 00/72765 A1 | 12/2000 |
| WO | WO 94/18893 | A1 | 9/1994 | WO | WO 01/03587 A1 | 1/2001 |
| WO | WO 94/22378 | A1 | 10/1994 | WO | WO 01/05702 A1 | 1/2001 |
| WO | WO 94/23659 | A1 | 10/1994 | WO | WO 01/10482 A1 | 2/2001 |
| WO | WO 95/02369 | A1 | 1/1995 | WO | WO 01/35845 A1 | 5/2001 |
| WO | WO 95/03743 | A1 | 2/1995 | WO | WO 01/54594 A1 | 8/2001 |
| WO | WO 95/06817 | A1 | 3/1995 | WO | WO 01/58371 A1 | 8/2001 |
| WO | WO 95/09576 | A1 | 4/1995 | WO | WO 01/62158 A2 | 8/2001 |
| WO | WO 95/09577 | A1 | 4/1995 | WO | WO 01/62161 A1 | 8/2001 |
| WO | WO 95/14436 | A1 | 6/1995 | WO | WO 01/62162 A1 | 8/2001 |
| WO | WO 95/17855 | A1 | 7/1995 | WO | WO 01/62164 A2 | 8/2001 |
| WO | WO 95/18572 | A1 | 7/1995 | WO | WO 01/62169 A2 | 8/2001 |
| WO | WO 95/18683 | A1 | 7/1995 | WO | WO 01/78605 A2 | 10/2001 |
| WO | WO 95/19739 | A1 | 7/1995 | WO | WO 01/91646 A1 | 12/2001 |
| WO | WO 95/20360 | A1 | 8/1995 | WO | WO 02/07608 A2 | 1/2002 |
| WO | WO 95/23557 | A1 | 9/1995 | WO | WO 02/07618 A1 | 1/2002 |
| WO | WO 95/24865 | A1 | 9/1995 | WO | WO 02/17799 A1 | 3/2002 |
| WO | WO 95/25471 | A3 | 9/1995 | WO | WO 02/19920 A1 | 3/2002 |
| WO | WO 95/26562 | A1 | 10/1995 | WO | WO 02/19932 A1 | 3/2002 |
| WO | WO 95/29639 | A1 | 11/1995 | WO | WO 02/30297 A2 | 4/2002 |
| WO | WO 96/04858 | A1 | 2/1996 | WO | WO 02/32322 A2 | 4/2002 |
| WO | WO 96/19151 | A1 | 6/1996 | WO | WO 02/36028 A1 | 5/2002 |
| WO | WO 96/19152 | A1 | 6/1996 | WO | WO 02/43571 A2 | 6/2002 |
| WO | WO 96/20652 | A1 | 7/1996 | WO | WO 02/058568 A1 | 8/2002 |
| WO | WO 96/21119 | A1 | 7/1996 | WO | WO 02/060328 A1 | 8/2002 |
| WO | WO 96/22055 | A1 | 7/1996 | WO | WO 02/067785 A2 | 9/2002 |
| WO | WO 96/23448 | A1 | 8/1996 | WO | WO 02/098302 A1 | 12/2002 |
| WO | WO 96/24301 | A1 | 8/1996 | WO | WO 03/000138 A2 | 1/2003 |
| WO | WO 96/27337 | A1 | 9/1996 | WO | WO 03/001329 A2 | 1/2003 |
| WO | WO 96/31155 | A1 | 10/1996 | WO | WO 03/013363 A1 | 2/2003 |
| WO | WO 96/35464 | A1 | 11/1996 | WO | WO 03/015604 A1 | 2/2003 |
| WO | WO 96/39085 | A1 | 12/1996 | WO | WO 03/020106 A2 | 3/2003 |
| WO | WO 96/39086 | A1 | 12/1996 | WO | WO 03/020139 A2 | 3/2003 |
| WO | WO 96/39087 | A1 | 12/1996 | WO | WO 03/024339 A1 | 3/2003 |
| WO | WO 96/39088 | A1 | 12/1996 | WO | WO 03/079909 A3 | 3/2003 |
| WO | WO 96/39089 | A1 | 12/1996 | WO | WO 03/030743 A2 | 4/2003 |
| WO | WO 97/00646 | A1 | 1/1997 | WO | WO 03/037193 A1 | 5/2003 |
| WO | WO 97/00647 | A1 | 1/1997 | WO | WO 03/047436 A3 | 6/2003 |
| WO | WO 97/06582 | A1 | 2/1997 | WO | WO 03/055402 A1 | 7/2003 |
| WO | WO 97/10763 | A1 | 3/1997 | WO | WO 03/057048 A1 | 7/2003 |
| WO | WO 97/10764 | A1 | 3/1997 | WO | WO 03/057058 A1 | 7/2003 |
| WO | WO 97/11649 | A1 | 3/1997 | WO | WO 03/063694 A1 | 8/2003 |
| WO | WO 97/16648 | A2 | 4/1997 | WO | WO 03/077769 A1 | 9/2003 |
| WO | WO 97/15237 | A1 | 5/1997 | WO | WO 03/079911 A1 | 10/2003 |
| WO | WO 97/24073 | A1 | 7/1997 | WO | WO 03/082126 A1 | 10/2003 |
| WO | WO 97/24993 | A1 | 7/1997 | WO | WO 03/088845 A2 | 10/2003 |
| WO | WO 97/30644 | A1 | 8/1997 | WO | WO 03/090630 A2 | 11/2003 |
| WO | WO 97/34533 | A1 | 9/1997 | WO | WO 03/094743 A1 | 11/2003 |
| WO | WO 97/37598 | A1 | 10/1997 | WO | WO 03/094745 A1 | 11/2003 |
| WO | WO 97/39688 | A2 | 10/1997 | WO | WO 03/094746 A1 | 11/2003 |
| WO | WO 98/17180 | A1 | 4/1998 | WO | WO 03/094747 A1 | 11/2003 |
| WO | WO 98/27880 | A1 | 7/1998 | WO | WO 03/101313 A1 | 12/2003 |
| WO | WO 98/30153 | A1 | 7/1998 | WO | WO 03/105698 A2 | 12/2003 |
| WO | WO 98/47436 | A1 | 10/1998 | WO | WO 03/105702 A2 | 12/2003 |
| WO | WO 99/03407 | A1 | 1/1999 | WO | WO 2004/006980 A2 | 1/2004 |
| WO | WO 99/03408 | A1 | 1/1999 | WO | WO 2004/011037 A2 | 2/2004 |
| WO | WO 99/03409 | A1 | 1/1999 | WO | WO 2004/019769 A1 | 3/2004 |
| WO | WO 99/12483 | A1 | 3/1999 | WO | WO 2004/021868 A2 | 3/2004 |
| WO | WO 99/12487 | A1 | 3/1999 | WO | WO 2004/028585 A2 | 4/2004 |
| WO | WO 99/12488 | A1 | 3/1999 | WO | WO 2004/032754 A2 | 4/2004 |
| WO | WO 99/15086 | A1 | 4/1999 | WO | WO 2004/032760 A2 | 4/2004 |
| WO | WO 99/15091 | A1 | 4/1999 | WO | WO 2004/032762 A1 | 4/2004 |

| | | |
|---|---|---|
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2009/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/070763 A1 | 6/2008 |
| WO | WO 2008/089404 A2 | 7/2008 |
| WO | WO 2008/109125 A1 | 9/2008 |
| WO | WO 2010/063795 A1 | 6/2010 |
| WO | WO 2012/044844 A2 | 4/2012 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

European Examination Report for Application No. 08251944.8, dated Jul. 25, 2011 (5 pages).

Van Meer et al., "A Disposable Plastic Compact Wrist for Smart Minimally Invasive Surgical Tools," LAAS/CNRS (Aug. 2005).

Breedveld et al., "A New, Easily Minaturized Sterrable Endoscope," IEEE Engineering in Medicine and Biology Magazine (Nov./Dec. 2005).

D. Tuite. Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

U.S. Appl. No. 13/118,194, filed May 27, 2001.
U.S. Appl. No. 12/032,024, filed Feb. 15, 2009.
U.S. Appl. No. 12/031,580, filed Feb. 15, 2008.
U.S. Appl. No. 13/118,272, filed May 27, 2011.
U.S. Appl. No. 13/118,263, filed May 27, 2011.
U.S. Appl. No. 13/118,223, filed May 27, 2011.
U.S. Appl. No. 13/118,190, filed May 27, 2011.
U.S. Appl. No. 13/118,278, filed May 27, 2011.
U.S. Appl. No. 13/118,253, filed May 27, 2011.
U.S. Appl. No. 13/118,194, filed May 27, 2011.
U.S. Appl. No. 13/118,210, filed May 27, 2011.
U.S. Appl. No. 13/118,259, filed May 27, 2011.
U.S. Appl. No. 13/118,246, filed May 27, 2011.

European Search Report for Application No. 08251944.8, published May 19, 2010 (3 pages).

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

U.S. Appl. No. 13/310,107, filed Dec. 2, 2011.
U.S. Appl. No. 13/369,561, filed Feb. 9, 2012.
U.S. Appl. No. 13/369,629, filed Feb. 9, 2012.
U.S. Appl. No. 13/372,195, filed Feb. 13, 2012.
U.S. Appl. No. 13/486,175, filed Jun. 1, 2012.
U.S. Appl. No. 13/480,263, filed May 24, 2012.

* cited by examiner

SURGICAL INSTRUMENT HAVING A DIRECTIONAL SWITCHING MECHANISM

CROSS-REFERENCE TO RELATED APPLICATIONS

The present application is a divisional application claiming priority under 35 U.S.C. §121 from co-pending U.S. patent application Ser. No. 11/810,016, entitled SURGICAL INSTRUMENT HAVING A DIRECTIONAL SWITCHING MECHANISM, filed on Jun. 4, 2007, the entire disclosure of which is incorporated by reference herein.

The following commonly-owned U.S. Patent Applications are hereby incorporated by reference in their entirety:
(1) U.S. patent application Ser. No. 11/809,935, now U.S. Pat. No. 7,819,299, entitled SURGICAL INSTRUMENT HAVING A COMMON TRIGGER FOR ACTUATING AN END EFFECTOR CLOSING SYSTEM AND A STAPLE FIRING SYSTEM; and
(2) U.S. patent application Ser. No. 11/810,015, now U.S. Patent Publication No. 2008/0300613, entitled SURGICAL INSTRUMENT HAVING A MULTIPLE RATE DIRECTIONAL SWITCHING MECHANISM.

BACKGROUND

1. Field of the Invention

The present invention generally relates to surgical stapling instruments and, more particularly, to surgical staplers having an end effector closing system and a firing system for deploying staples.

2. Description of the Related Art

As known in the art, surgical staplers are often used to deploy staples into soft tissue to reduce or eliminate bleeding from the soft tissue, especially as the tissue is being transected, for example. Surgical staplers, such as an endocutter, for example, often comprise an end effector which is configured to secure the soft tissue between first and second jaw members. The first jaw member often includes a staple cartridge which is configured to removably store staples therein and the second jaw member often includes an anvil. In use, the staples are typically deployed from the staple cartridge by a driver which traverses a channel in the staple cartridge and causes the staples to be deformed against the anvil and secure layers of the soft tissue together. Often, as known in the art, the staples are deployed in several staple lines, or rows, in order to more reliably secure the layers of tissue together. The end effector may also include a cutting member, such as a knife, for example, which is advanced between two rows of the staples to resect the soft tissue after the layers of the soft tissue have been stapled together.

After the driver and the cutting member have been advanced within the end effector, it is often necessary to retract the driver and/or cutting member to their starting positions. Previous surgical staplers have included a return spring which retracts the cutting member relative to the staple cartridge after a release button or toggle switch on the surgical stapler has been actuated by the surgeon. Such staplers, however, are unable to partially retract the cutting member and, as a result, the cutting member must be fully retracted before it can be readvanced. Other previous surgical staplers have included a plurality of triggers which are operatively engaged with systems for closing a jaw member and for advancing and/or retracting the driver and cutting member. Such devices, while suitable for their intended purposes, often require a surgeon to release a trigger operably engaged with the closing system and reposition their hand to grasp a different trigger which is operatively engaged with a system for advancing the staple driver and cutting member. While previous surgical staplers have been developed which have a single trigger for both closing the jaw member and advancing the driver and cutting member, such devices perform both functions upon the initial actuation of the trigger. While suitable in some circumstances, devices which perform both functions in the same trigger actuation are often exceedingly difficult to operate owing to the high degree of force required to actuate the trigger. Furthermore, such devices, as they close the jaw member and deploy staples in the same trigger actuation, do not afford the surgeon with an opportunity to evaluate the position of the closed jaw member and reposition the jaw member before the staples are deployed into the soft tissue. What is needed is an improvement over the foregoing.

SUMMARY

In at least one form of the invention, a surgical instrument can include a switching mechanism which can allow a surgeon, or other clinician, to selectively advance or retract a staple driver and/or cutting member within a staple cartridge. In various embodiments, the surgical instrument can include a handle, a trigger operatively coupled to the handle, a firing drive, and an end effector. In at least one embodiment, the firing drive can include a first ratchet assembly configured to advance a cutting member in the end effector and a second ratchet assembly configured to retract the cutting member. In various embodiments, the trigger can include first and second pawls pivotably mounted thereon which are configured to be selectively engaged with the first and second ratchet assemblies, respectively. In at least one such embodiment, the trigger can be configured to slide between a first position in which the first pawl is engaged with the first ratchet assembly and a second position in which the second pawl is engaged with the second ratchet assembly. In such embodiments, a surgeon can quickly and conveniently select between advancing and retracting motions of the cutting member.

In at least one form of the invention, a surgical instrument can include a drive mechanism configured to advance a staple driver and/or cutting member at a first rate and retract the staple driver and/or cutting member at a different rate. In at least one embodiment, the rate at which the driver and cutting member are advanced and/or retracted is the distance that the driver and cutting member are translated per actuation, or stroke, of a trigger, for example. Accordingly, in such embodiments, a first rate is considered to be faster than a second rate if the trigger advances or retracts the cutting member a greater distance per actuation. In various embodiments, the cutting member can be retracted at a faster rate as compared to the rate in which it is advanced. In such embodiments, the surgical instrument can, owing to the slower advancing rate, provide a greater torque or advancing force to the cutting member while, owing to the faster retracting rate, reduce the time required for the surgeon to retract the cutting member. In various embodiments, as described above, the surgical instrument can include a switching mechanism configured to selectively engage one of a first drive system and a second drive system with a rotatable drive shaft. In at least one such embodiment, the first drive system can include a first gear having a first pitch radius and the second drive system can include a second gear having a different pitch radius where the first and second gears can rotate the drive shaft at different rates.

In at least one form of the invention, a surgical instrument can include a trigger which can be configured to close a jaw member onto soft tissue, for example, upon a first actuation of the trigger and advance a staple driver and/or cutting member upon a subsequent, or second, actuation of the trigger. In various embodiments, such a surgical instrument can allow a surgeon to position the surgical instrument in a surgical site and close the jaw member with an initial actuation of the trigger without deploying any staples into, or incising, the tissue. In such embodiments, as a result, the surgeon can manipulate the position of the surgical instrument and then actuate the trigger a second time to deploy staples into, and/or incise, the tissue. In at least one such embodiment, the first actuation of the trigger which closes the jaw member can also unlock a firing drive configured to advance the staple driver and cutting member during the second actuation of the trigger. In various embodiments, the surgical instrument can include a switching mechanism which can allow the surgeon to reopen the jaw member and, if they so choose, to reposition the jaw member in a more suitable position.

BRIEF DESCRIPTION OF THE DRAWINGS

The above-mentioned and other features and advantages of the various embodiments of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

In various embodiments, a surgical instrument in accordance with the present invention can include systems for inserting surgical staples into soft tissue, for example. In at least one embodiment, the surgical instrument can include a staple cartridge configured to removably store staples therein and an anvil for deforming the staples as they are deployed from the staple cartridge. In order to deploy the staples, the surgical instrument can include a staple driver configured to traverse the staple cartridge and a firing drive for advancing the staple driver within the staple cartridge. In various embodiments, the firing drive can include a drive bar which is translated in a substantially linear direction by a trigger operably engaged therewith. In other embodiments, the firing drive can include a drive shaft which is rotated by the trigger. In such embodiments, the surgical instrument can include a shaft assembly which can convert the rotary motion of the drive shaft into linear motion and translate the staple driver within the staple cartridge. While the exemplary embodiment illustrated in FIGS. 1-20 and described below includes a firing drive having a rotary drive shaft, the present invention is not so limited. Furthermore, while a general description of a firing drive having a rotary drive shaft is provided below, other such devices are described and illustrated in greater detail in the commonly-owned, co-pending U.S. patent application Ser. No. 11/475,412, entitled MANUALLY DRIVEN SURGICAL CUTTING AND FASTENING INSTRUMENT and filed on Jun. 27, 2006, the entire disclosure of which is hereby incorporated by reference herein.

Figure 1:
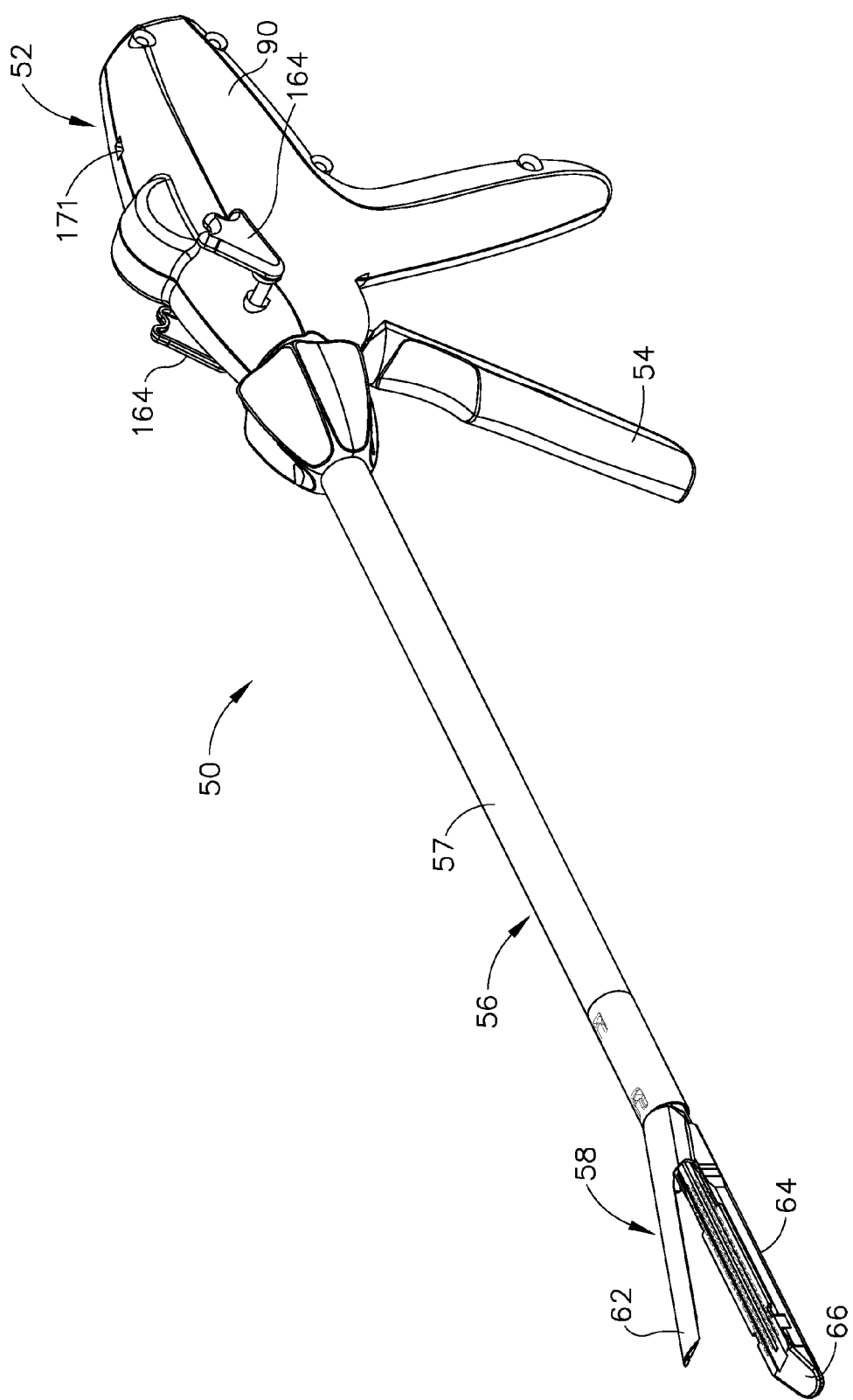
FIG. 1 is a perspective view of a surgical instrument in accordance with an embodiment of the present invention.
Figure 8:
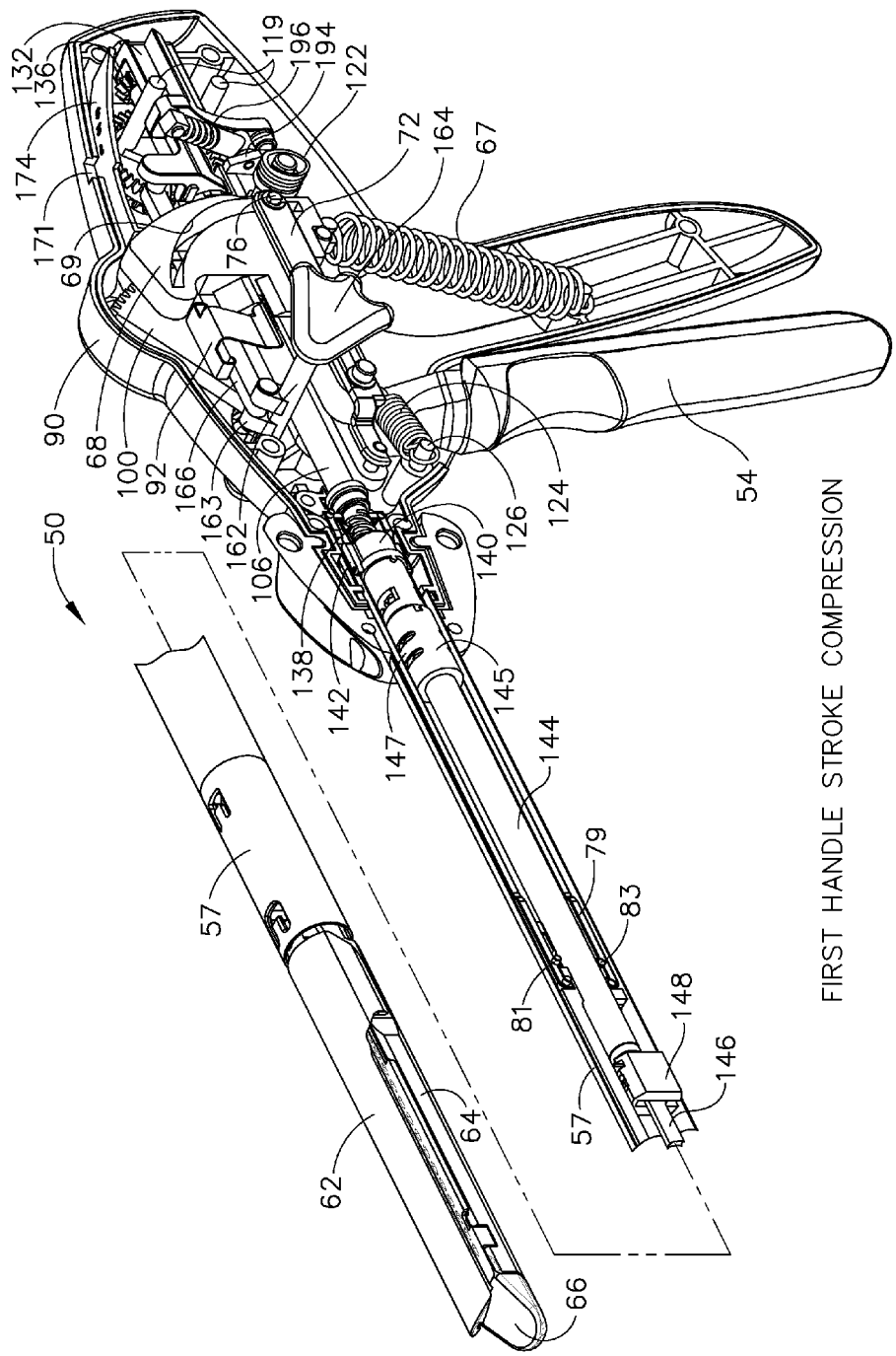
FIG. 8 is a perspective view of the surgical instrument of FIG. 1 illustrating the configuration of the surgical instrument upon the first actuation of the trigger.

Referring to FIG. 1, surgical instrument 50 can include handle portion 52, trigger 54, elongate shaft assembly 56, and end-effector 58. In various embodiments, end-effector 58 can include anvil 62 and staple cartridge channel 64, where channel 64 can be configured to receive staple cartridge 66 and anvil 62 can be pivotably connected to channel 64. In at least one embodiment, at least one of anvil 62 and channel 64 can be operably connected to trigger 54 such that, upon an actuation of trigger 54, anvil 62 can be rotated into a closed position as illustrated in FIG. 8. In various embodiments, referring to FIGS. 2-4, trigger 54 can be operably engaged with a closure drive system configured to translate both anvil 62 and channel 64 relative to outer sheath 57 of elongate shaft assembly 56. Referring primarily to FIG. 4, the closure drive can include cam 68 operably engaged with trigger 54 such that a first actuation of trigger 54 can rotate cam 68 about pin 70 and drive closure links 72 in a substantially linear direction. More particularly, trigger 54 can include lift pin 55 (FIG. 3) extending therefrom which can be configured to contact surface 71 of cam 68 and lift cam 68 into the position illustrated in FIG. 8. Cam 68 can further include cam slot 69 where, when cam 68 is rotated from its position illustrated in FIG. 4 to its position illustrated in FIG. 8, the side walls of cam slot 69 can engage closure link pin 76 and, in the present embodiment, slide closure links 72 in a direction illustrated by arrow A (FIG. 4).

Figure 2:
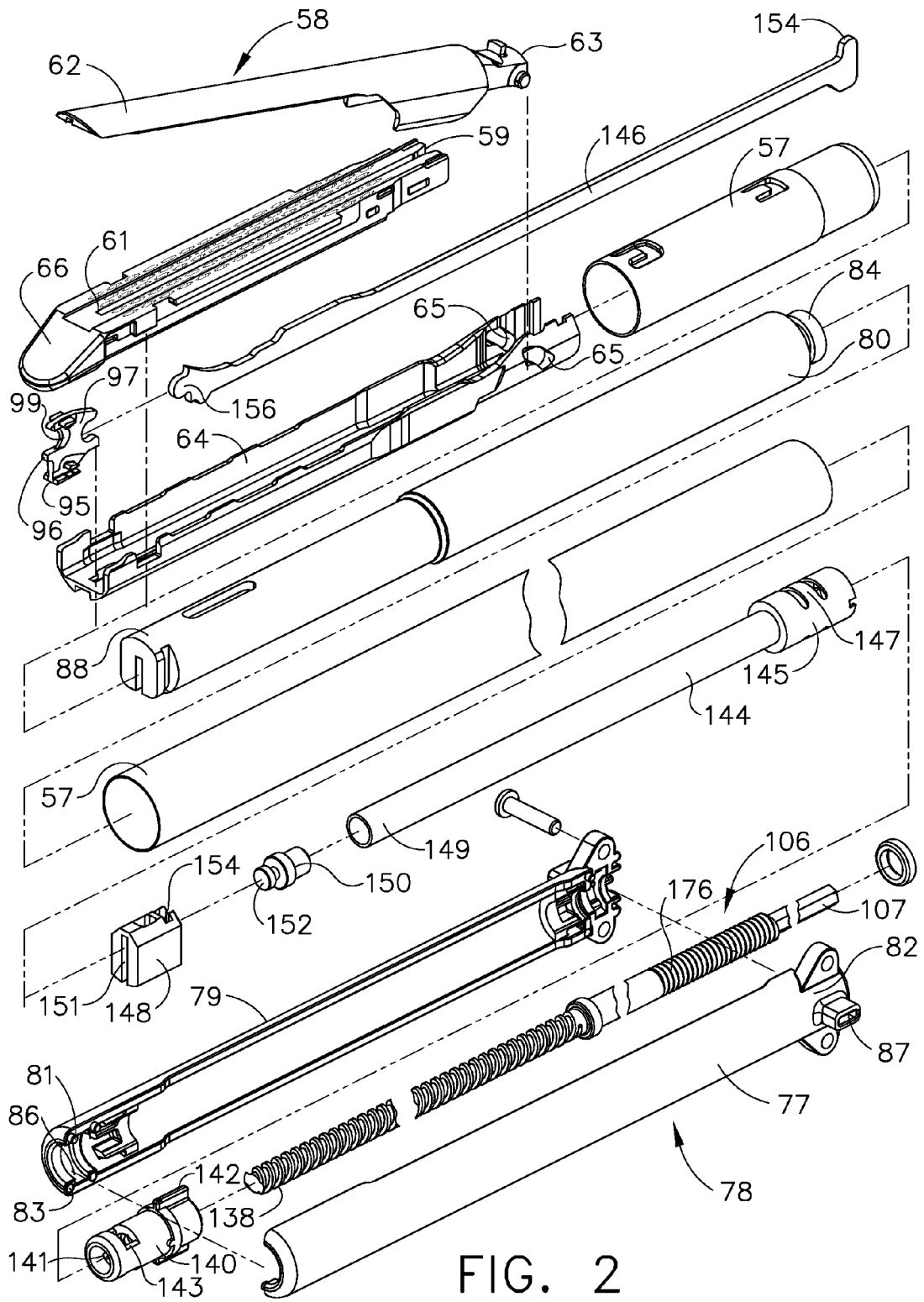
FIG. 2 is an exploded view of a shaft portion and end effector of the surgical instrument of FIG. 1.

Referring to FIGS. 2 and 4, surgical instrument 50 can further include a spine assembly within elongate shaft assembly 56 (FIG. 1), where the spine assembly can include proximal channel portion 78 and distal channel portion 80. In various embodiments, channel portions 78 and 80 can be interconnected by the cooperative engagement of projection, or tongue, 84 and groove 86. More particularly, referring to FIG. 2, proximal channel portion 78 can include, in various embodiments, first half 77 and second half 79 which can be assembled to distal channel portion 80 such that projection 84 is secured within groove 86. In at least one embodiment, proximal channel portion halves 77 and 79 can include projections 81 and/or apertures 83 configured to provide a snap-fit or press-fit engagement between proximal channel portion halves 77 and 79. In various other embodiments, channel portions 78 and 80 can be interconnected by any suitable means and, in at least one embodiment, although not illustrated, portions 78 and 80 can be integrally formed. Similar to the above, referring to FIG. 2, distal channel portion 80 can include distal end 88 which can be connected to staple cartridge channel 64. More particularly, distal channel portion 80 and staple cartridge channel 64 can include cooperating tongue and groove features, for example, which can provide a press-fit or snap-fit interconnection therebetween, although any other suitable interconnection therebetween can be used.

Referring to FIG. 4, proximal end 82 of channel portion 78 can be coupled to closure links 72 by pin 53 such that, when closures links 72 are translated by cam 68, channel portion 78 is translated within elongate shaft assembly 56. In at least one embodiment, channel portion 78 can further include projections 87 extending therefrom which can be configured to slide within recesses 85 (FIG. 3) in housing portions 90 and substantially limit the translation of channel portion 78 along an axis. As staple cartridge channel 64 is connected to proximal channel portion 78 via distal channel portion 80, channel 64, and anvil 62 pivotably connected thereto, can be moved in direction A when cam 68 is rotated by trigger 54 as described above. In at least one embodiment, referring to FIG. 2, proximal end 63 of anvil 62 can be configured to abut outer sheath 57 of elongate shaft assembly 56 when channel 64 and anvil 62 are translated relative to sheath 57. After proximal end 63 of anvil 62 contacts outer sheath 57, anvil 62 can be configured to rotate toward channel 64 and staple cartridge 66 in order to close anvil 62 as illustrated in FIG. 8. In various embodiments, referring to FIG. 2, channel 64 can include slots 65 therein which can be configured to guide anvil 62 as it is pivoted relative to channel 64. Once anvil 62 is closed, the surgical instrument can further include a lock which holds anvil 62 in its closed position. In various embodiments, referring to FIGS. 9-11, surgical instrument 50 can include spring lock 92 mounted to housing 90, where spring lock 92 can be configured to releasably hold cam 68 in position which, as a result, locks closure links 72, channel portions 78 and 80, channel 64, and anvil 62 in position until a surgeon desires to open anvil 62 as described in detail further below.

In various embodiments, after anvil 62 has been placed into its closed position, trigger 54 can be actuated a second time to operate a firing drive which advances cutting member 96 within end effector 58. In at least one embodiment, the firing drive can be disengaged from trigger 54 prior to the first actuation of trigger 54. In such embodiments, the first actuation of trigger 54 can operably engage trigger 54 with the firing drive and/or release a component of the firing drive such that the firing drive becomes operably engaged with trigger 54. In the illustrated embodiment, referring to FIGS. 3 and 4, the firing drive can include trigger gear portion 100 extending from trigger 54, gear train 102, gear carriage 130, and rotatable drive shaft 106 which can be configured to advance cutting member 96 within end effector 58 as described in greater detail below. As illustrated in FIGS. 3-7, gear train 102 can include ratchet gear 108, main drive gear 110, bevel drive gear 112, and bevel gear 114 where, prior to the first actuation of trigger 54, cam 68 can be configured to bias ratchet gear 108 out of engagement with main drive gear 110. More particularly, referring to FIG. 3, ratchet gear 108 can include shaft 116 and collar 118 where cam 68 can be configured to contact collar 118 and bias ratchet gear 108 away from main drive gear 112 such that ratchet face 109 on ratchet gear 108 is not engaged with ratchet face 111 on main drive gear 110.

Upon the first actuation of trigger 54, as described above, cam 68 can be rotated into the position illustrated in FIG. 8 and, as a result of such rotation, groove 120 (FIGS. 4 and 5) in cam 68 can be configured to release ratchet gear 108. More particularly, referring to FIGS. 5-7, groove 120 can be dimensioned such that, when the rotation of cam 68 aligns groove 120 with collar 118, collar 118 can slide past cam 68 and allow ratchet spring 122 to bias ratchet gear 108 into operative engagement with main drive gear 110. Thereafter, trigger 54 can be released and then returned to its starting position by trigger spring 124 where trigger spring 124 can be connected to pin 126 extending from housing 90 and pin 128 extending from trigger 54. Notably, eventhough trigger 54 can be returned to its starting position, cam 68 can remain locked in its second position by lock 92, as described above, thereby maintaining the alignment between groove 120 and collar 118. With ratchet gear 108 now operably engaged with drive gear 110, a second actuation of trigger 54 can advance cutting member 96 and the staple driver within end effector 58.

Figure 3:
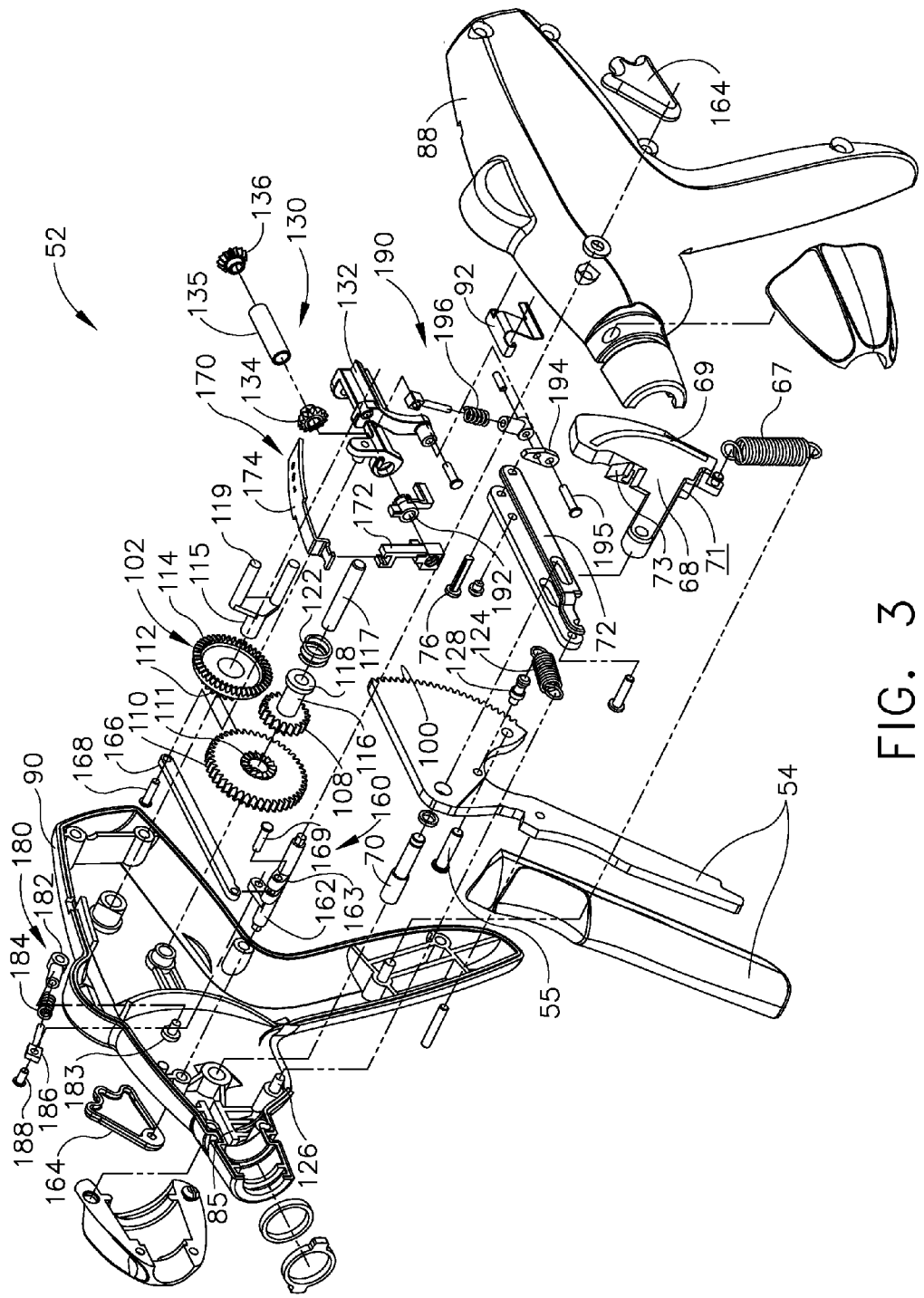
FIG. 3 is an exploded view of a handle portion of the surgical instrument of FIG. 1.
Figure 4:
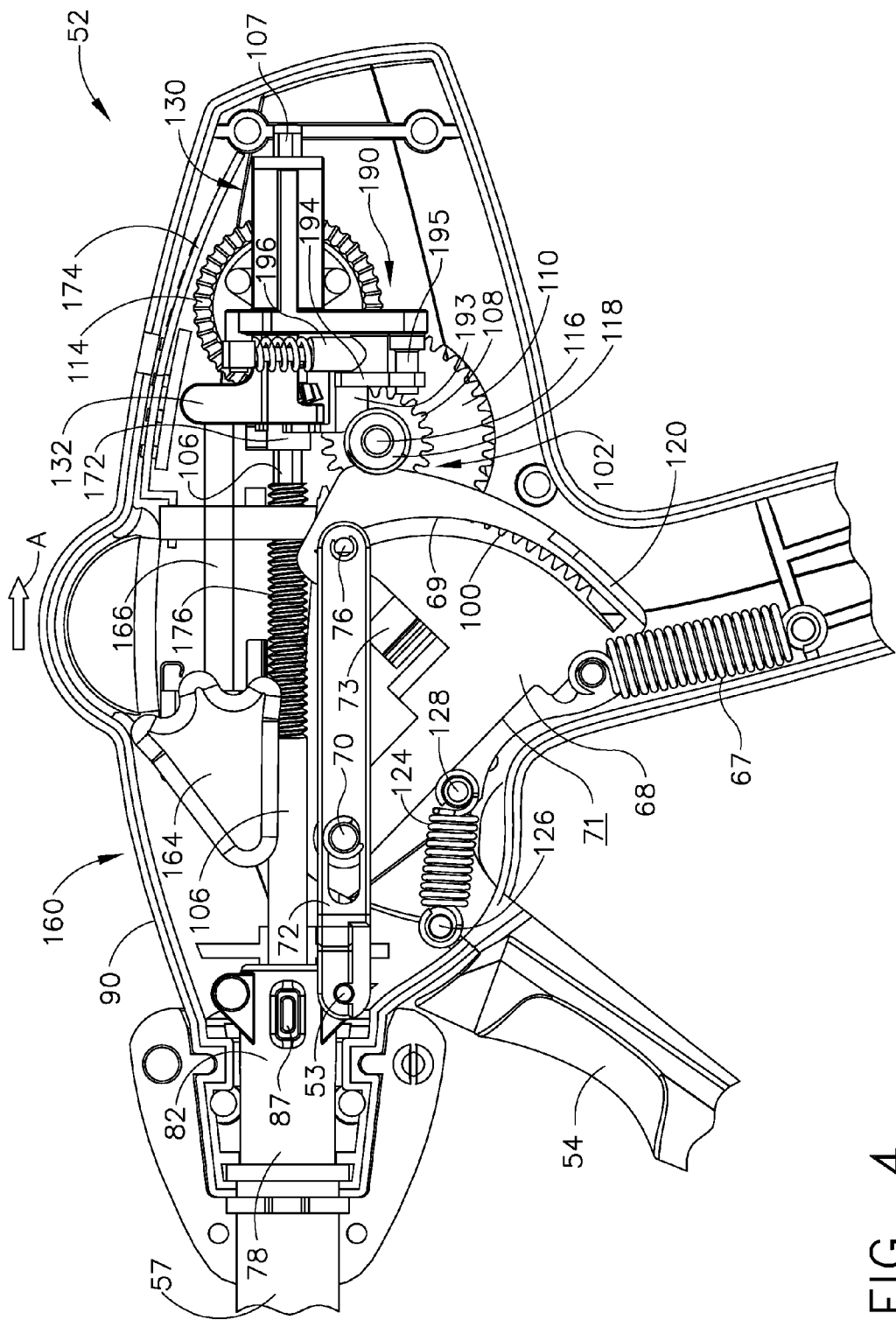
FIG. 4 is partial side view of the handle portion of FIG. 3 with some components of the surgical instrument removed.

Referring primarily to FIGS. 3 and 4, an actuation of trigger 54 can rotate trigger gear portion 100 about an axis defined by pin 70. Trigger gear portion 100 can include gear teeth extending along the perimeter thereof which can, referring to FIGS. 5 and 6, be engaged with gear teeth extending around the circumference, for example, of ratchet gear 108. In use, as a result, the actuation, or rotation, of trigger 54 can rotate ratchet gear 108 about an axis defined by shaft 116 and pin 117 (FIG. 3). As described above, ratchet gear 108 can, referring to FIGS. 5 and 6, include ratchet face 109 which can be configured to engage ratchet face 111 of main drive gear 110. In at least one embodiment, ratchet faces 109 and 111 can be configured to transmit the rotational motion of trigger 54 to main drive gear 110 upon the second actuation, or other subsequent actuation, of trigger 54 but also permit relative sliding movement therebetween when trigger 54 is released and returned to its unactuated position. In effect, ratchet faces 109 and 111 can be configured to transmit rotational motion to main drive gear 110 when ratchet gear 108 is rotated in one direction but not transmit rotational motion to main drive gear 110 when ratchet gear 108 is rotated in the opposite direction. Although a ratchet mechanism has been described and illustrated herein, any other suitable mechanism for transmitting motion between trigger 54 and main drive gear 110 can be used. Furthermore, although trigger 54 has been described and illustrated as a lever, any other suitable device can be used to motivate the firing and closing drives described herein.

Figure 5:
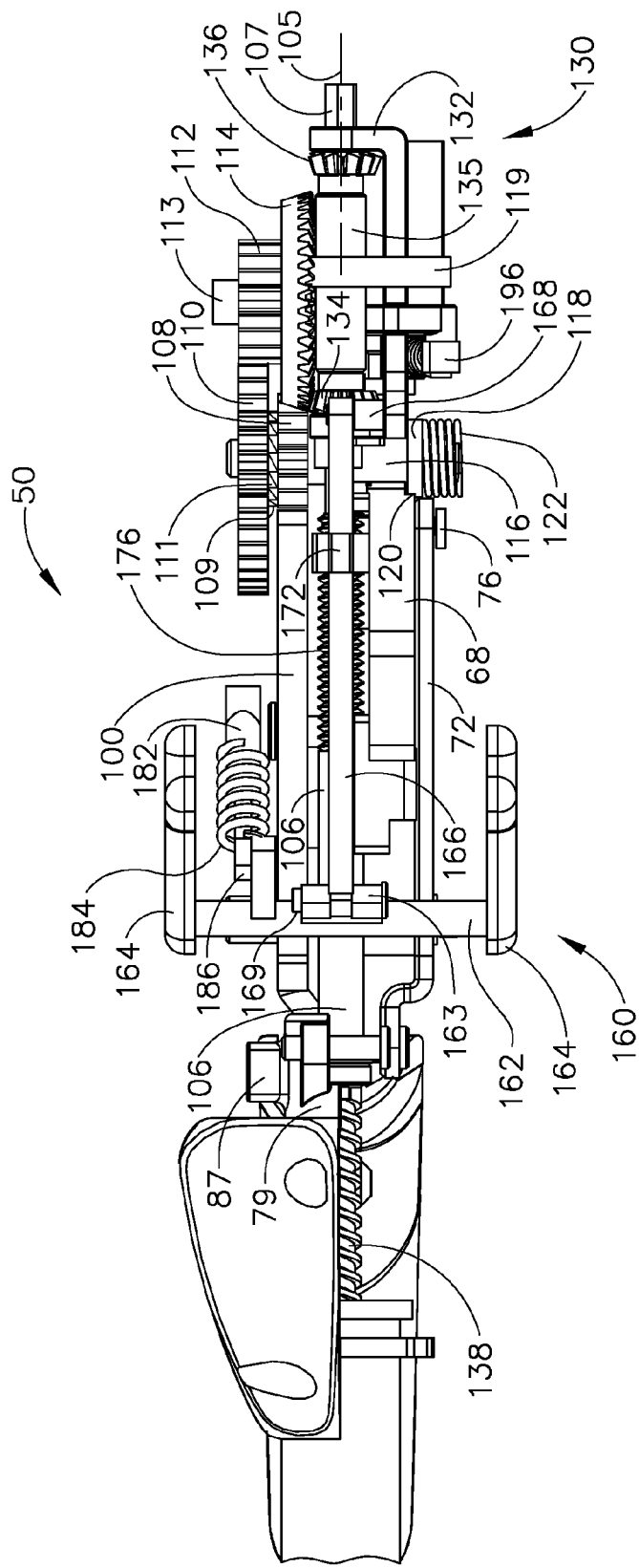
FIG. 5 is a top view of the handle portion of FIG. 3 with some components of the surgical instrument removed illustrating the surgical instrument in a configuration for advancing a cutting member in the end effector.
Figure 6:
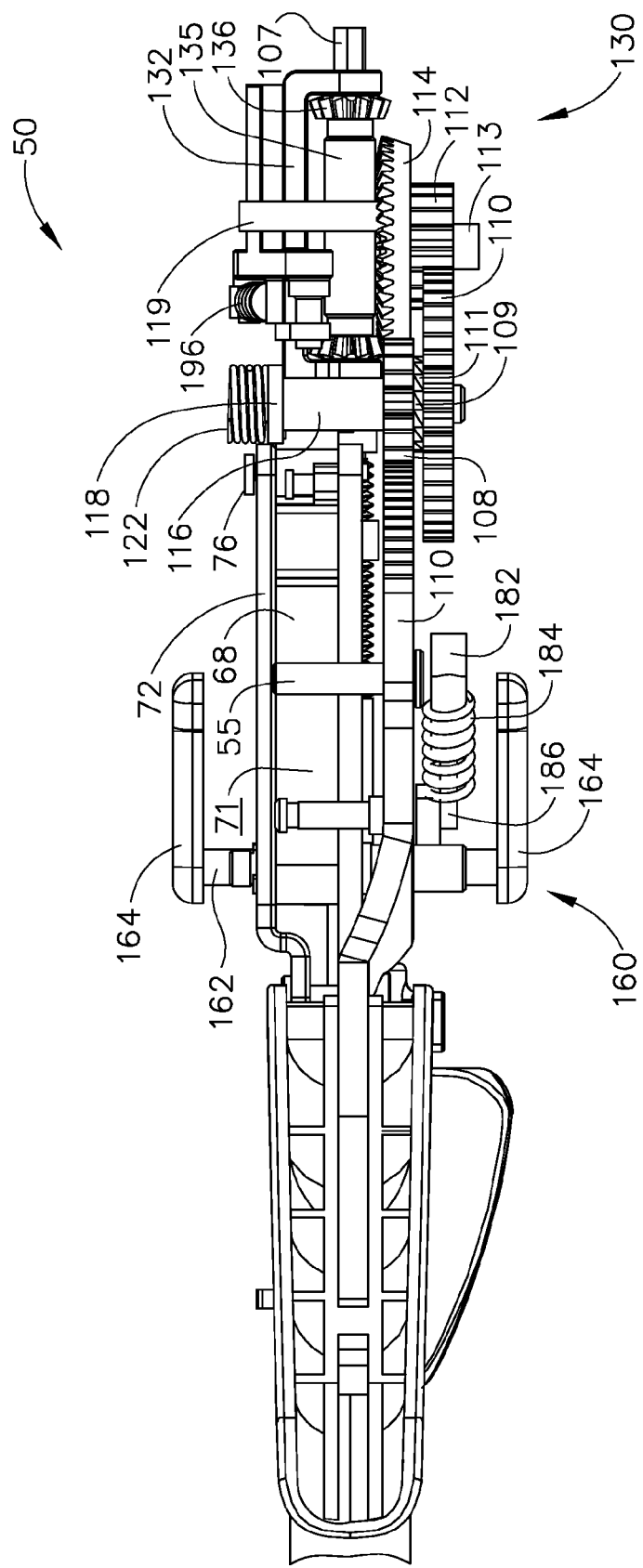
FIG. 6 is a bottom view of the handle portion of FIG. 3 with some components of the surgical instrument removed illustrating the surgical instrument in a configuration for advancing a cutting member in the end effector.
Figure 7:
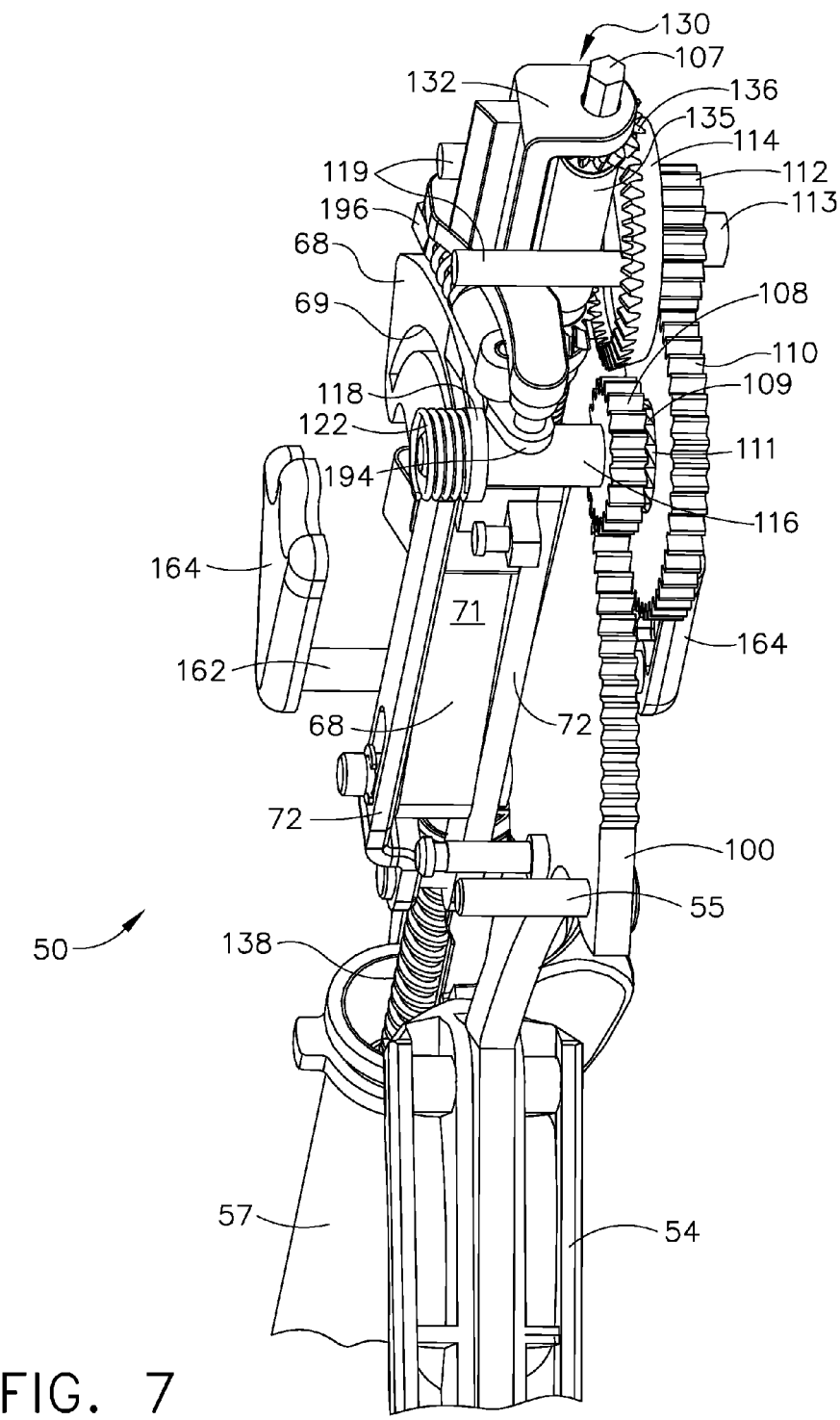
FIG. 7 is a partial perspective view of the handle portion of FIG. 3 with some components of the surgical instrument removed.

Referring primarily to FIGS. 5-7, main drive gear 110 can include gear teeth extending around the circumference thereof, for example, which can be engaged with gear teeth extending around the perimeter, for example, of bevel drive gear 112. In use, as a result, the rotational motion transmitted to main drive gear 110 from ratchet gear 108, for example, can be transmitted to bevel drive gear 112. In various embodiments, bevel drive gear 112 can be mounted to or integrally formed with shaft 113, where shaft 113 can define an axis about which bevel drive gear 112 can be rotated. In at least one embodiment, referring to FIG. 3, surgical instrument 50 can further include bracket 115 about which bevel drive gear 112 and shaft 113 can be rotated. As described in greater detail below, bracket 115 can also include supports 119 which can be configured to slidably support at least a portion of gear carriage 130. In various embodiments, referring to FIGS. 5-7, bevel gear 114 can be attached to bevel drive gear 112 or, alternatively, bevel gear 114 can be mounted to or integrally formed with shaft 113. In either event, the rotational motion transmitted to bevel drive gear 112 can be transmitted to bevel gear 114.

In various embodiments, although not illustrated, bevel gear 114 could be directly engaged with drive shaft 106 via cooperating bevel gear teeth. In at least one such embodiment, bevel gear 114 could rotate drive shaft 106 in a clockwise direction, for example, and advance cutting member 96 within end effector 58 as described below. In such embodiments, the actuation of trigger 54 could advance cutting member 96 within end effector 58, however, cutting member 96 would have to be retracted either manually or via an additional retraction system. In the illustrated embodiment of the present invention, referring to FIGS. 3 and 5-7, surgical instrument 50 can further include a switching mechanism which can allow drive shaft 106 to be rotated in either a clockwise or counter-clockwise direction and, correspondingly, allow cutting member 96 to be advanced or retracted via the actuation of trigger 54. In various embodiments, referring primarily to FIGS. 5 and 6, the switching mechanism can include gear carriage 130 which can be shifted between a first position in which the rotational motion of bevel gear 114 rotates drive shaft 106 in a clockwise direction, for example, and a second position in which the rotational motion of bevel gear 114 rotates drive shaft 106 in a counter-clockwise direction.

In various embodiments, referring to FIGS. 5-7, gear carriage 130 can include housing 132, forward gear 134, and reversing gear 136 where forward gear 134 and reversing gear 136 can be rotatably mounted to housing 132. In at least one embodiment, drive shaft 106 can include substantially hex-shaped end 107, for example, which can be received within apertures (not illustrated) in forward gear 134 and reversing gear 136 such that gears 134 and 134 are rotatably engaged with drive shaft 106. In other various embodiments, end 107 can include any other suitable shape or configuration such that gears 134 and 136 are rotatably engaged with drive shaft 106. In either event, referring to FIG. 5, gear carriage 130 can be slid along end 107 such that either forward gear 134 or reversing gear 136 can be engaged with bevel gear 114. In use, when forward gear 134 is engaged with bevel gear 114, for example, the rotational motion of bevel gear 114 can be transmitted to forward gear 134 and, owing to cooperating geometries of end 107 and the aperture in forward gear 134, the rotational motion of gear 134 can be transmitted to drive shaft 106. In order to rotate drive shaft in the opposite direction, gear carriage 130 can be slid proximally, or rearward, such that reversing gear 136 engages bevel gear 114. A mechanism for motivating gear carriage 130 in this manner is described further below.

In various embodiments, when forward gear 134 is engaged with bevel gear 114, as illustrated in FIG. 5, reversing gear 136 can be disengaged from bevel gear 114 such that reversing gear 136 is free to rotate with drive shaft 106. In at least one embodiment, gear carriage 130 can further include spacer 135 which can be configured to rotatably support and align gears 134 and 136 yet permit gears 134 and 136 to rotate independent of one another. In some embodiments, gear carriage 130 can be placed in a position intermediate the forward and rearward positions such that both gears 134 and 136 engage bevel gear 114 and hold drive shaft 106 in a 'locked-out' condition such that trigger 54 cannot be actuated. In other various embodiments, gear carriage 130 can be placed in an intermediate position such that neither gears 134 and 136 engage bevel gear 114. In such embodiments, the firing drive is in a 'free' condition and the rotational motion of bevel gear 114 is not transmitted to drive shaft 106.

In various embodiments, referring primarily to FIG. 2, drive shaft 106 can further include threaded drive portion 138 which can be operably engaged with firing nut 140. In at least one embodiment, threaded drive portion 138 can be configured to slidably advance and/or retract firing nut 140 in response to rotational motion of drive shaft 106. More particularly, firing nut 140 can include threaded aperture 141 which can be configured to threadably receive threaded drive portion 138 such that the rotation of drive shaft 106 produces a reactional force which advances firing nut 140 distally. In at least one embodiment, firing nut 140 can include projection 142 extending therefrom which can be configured to extend through a slot defined between proximal channel portion halves 77 and 79 in order to constrain the movement of firing nut 140 along an axis. In effect, the slot can prevent firing nut 140 from rotating with drive shaft 106 and can define a path for projection 142 as firing nut 140 is translated within channel portion 78.

In various embodiments, referring to FIG. 2, cutting member 96 can be operably engaged with firing nut 140 such that the translation of firing nut 140, as described above, can result in the translation of cutting member 96 within end effector 58. In at least one embodiment, surgical instrument 50 can further include firing rod 144 connected to firing nut 140, drive bar 146 connected to cutting member 96, and adapter 148 configured to connect drive bar 146 to firing rod 144. In various embodiments, firing rod 144 can include proximal end 145 which can include an aperture configured to receive at least a portion of firing nut 140 in a press-fit manner. In at least one embodiment, proximal end 145 of firing rod 144 can include deformable member 147 which can be configured to engage recess 143 in firing nut 140 after deformable member 147 has been depressed or deformed inwardly toward recess 143. In either event, firing rod 144 can further include distal end 149 which can be configured to receive plug 150 in a press-fit manner, for example, where plug 150 can include projection 152 extending therefrom which can be received within slot 154 in adapter 148. In various embodiments, adapter 148 can further include slot 151, where slot 151 can be configured to receive connector tab 154 of drive bar 146 such that, when adapter 148 is translated by firing rod 144, drive bar 146 can be translated within distal retainer section 80. In at least one embodiment, drive bar 146 can further include distal end 156 which can be configured to engage recess 97 in cutting member 96 and advance and/or retract cutting member 96 within end effector 58. As described above, cutting member 96 can include knife 99 which can be configured to incise tissue positioned between anvil 62 and staple cartridge 66 as cutting member 96 is advanced within end effector 58. Further, as described above, cutting member 96 can include portion 95, where portion 95 can be configured to push a staple driver (not illustrated) within staple cartridge 66 to deploy staples (not illustrated) removably stored therein.

In various embodiments, the surgical instrument can be configured to advance cutting member 96 a desired distance upon a single actuation of trigger 54, i.e., the second overall actuation of trigger 54 in embodiments where the first actuation of trigger 54 closes anvil 62 as described above. In other embodiments, however, more than one actuation of trigger 54 can be used to advance cutting member 96 a desired distance. In at least one such embodiment, referring to FIGS. 12-16, trigger 54 can be actuated three times to advance cutting member 96 from proximal end 59 to distal end 61 of end effector 58. The quantity of such actuations in other embodiments, however, will depend largely upon the overall distance that cutting member 96 is to be displaced and the displacement of cutting member 96 as a result of each actuation. Notably, prior to the second actuation of trigger 54, cutting member 96 can be positioned in proximal end 59 of end effector 58 and firing nut 140 can be positioned in its most proximal position. Upon the second actuation of trigger 54, referring to FIGS. 13 and 14, cutting member 96 can be advanced approximately one-third of the distance between proximal end 59 and distal end 61 and, similarly, firing nut 140 can be advanced distally along drive shaft 106. Thereafter, referring to FIG. 15, cutting member can be advanced an additional one-third of the distance between proximal end 59 and distal end 61 upon the third actuation of trigger 54 and, similarly, referring to FIG. 16, cutting member 96 can be advanced into distal end 61 of end effector 58 upon the fourth actuation of trigger 54.

In various embodiments, in order to assist a surgeon in monitoring the amount of times that trigger 54 has been actuated, surgical instrument 50 can include a counting mechanism which can be configured to display the amount of times that trigger 54 has been actuated and/or the amount of actuations remaining to deploy all of the staples in the staple cartridge. In either event, referring primarily to FIGS. 3 and 9, one embodiment of counting mechanism 170 can include indicator nut 172, indicator plate 174, and indictor window 171 (FIG. 1) in housing 90. In at least one embodiment, indicator plate 174 can include indicia thereon which can communicate to the surgeon the amount of times that trigger 54 has been actuated to advance cutting member 96. In such embodiments, indicator plate 174 can include blank portion 173 which is visible through window 171 before and after the first actuation of trigger 54, i.e., the actuation of trigger 54 which closes anvil 62 as described above. Upon the second actuation of trigger 54, the rotation of drive shaft 106 can advance indicator nut 172 and indicator plate 174, which is mounted to indicator nut 172, distally such that the numeral "1" or other appropriate indicia on indicator plate 174 can be seen through indicator window 171. Accordingly, such an indicium can indicate to the surgeon that cutting member 96 has been advanced by one actuation of trigger 54. Similar to firing nut 140, indicator nut 172 can include a threaded aperture which can be threadably engaged with threaded portion 176 of drive shaft 106 such that the rotation of drive shaft 106 applies a reactional force to indicator nut 172 and advances it distally. Subsequent actuations of trigger 54 can move the numerals '2' and '3' beneath indicator window 171.

Figure 17:
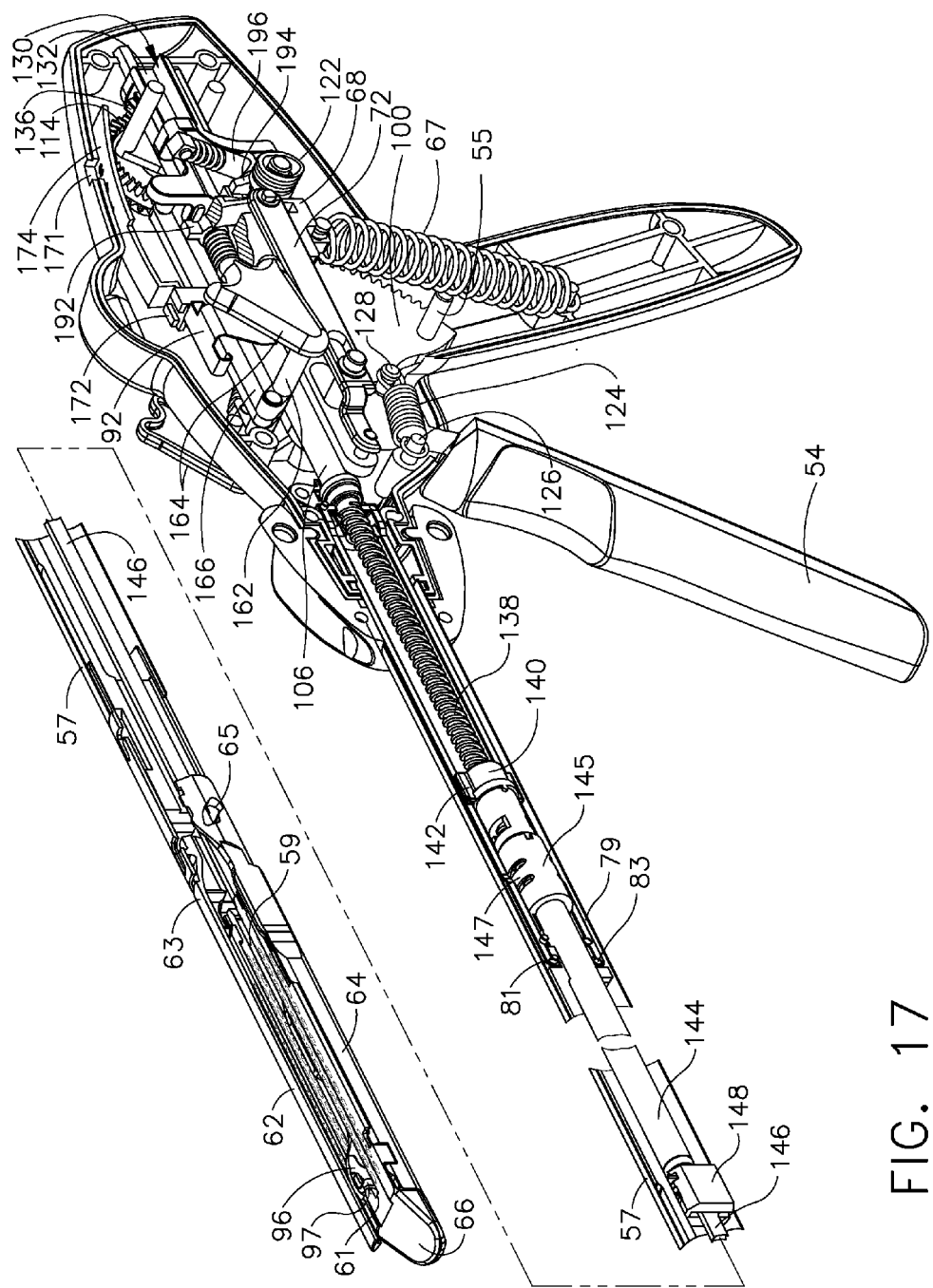
FIG. 17 is a perspective view of the surgical instrument of FIG. 1 illustrating the configuration of the surgical instrument after the trigger has been released after the fourth actuation of the trigger and the switching mechanism of the surgical instrument has been operated.
Figure 18:
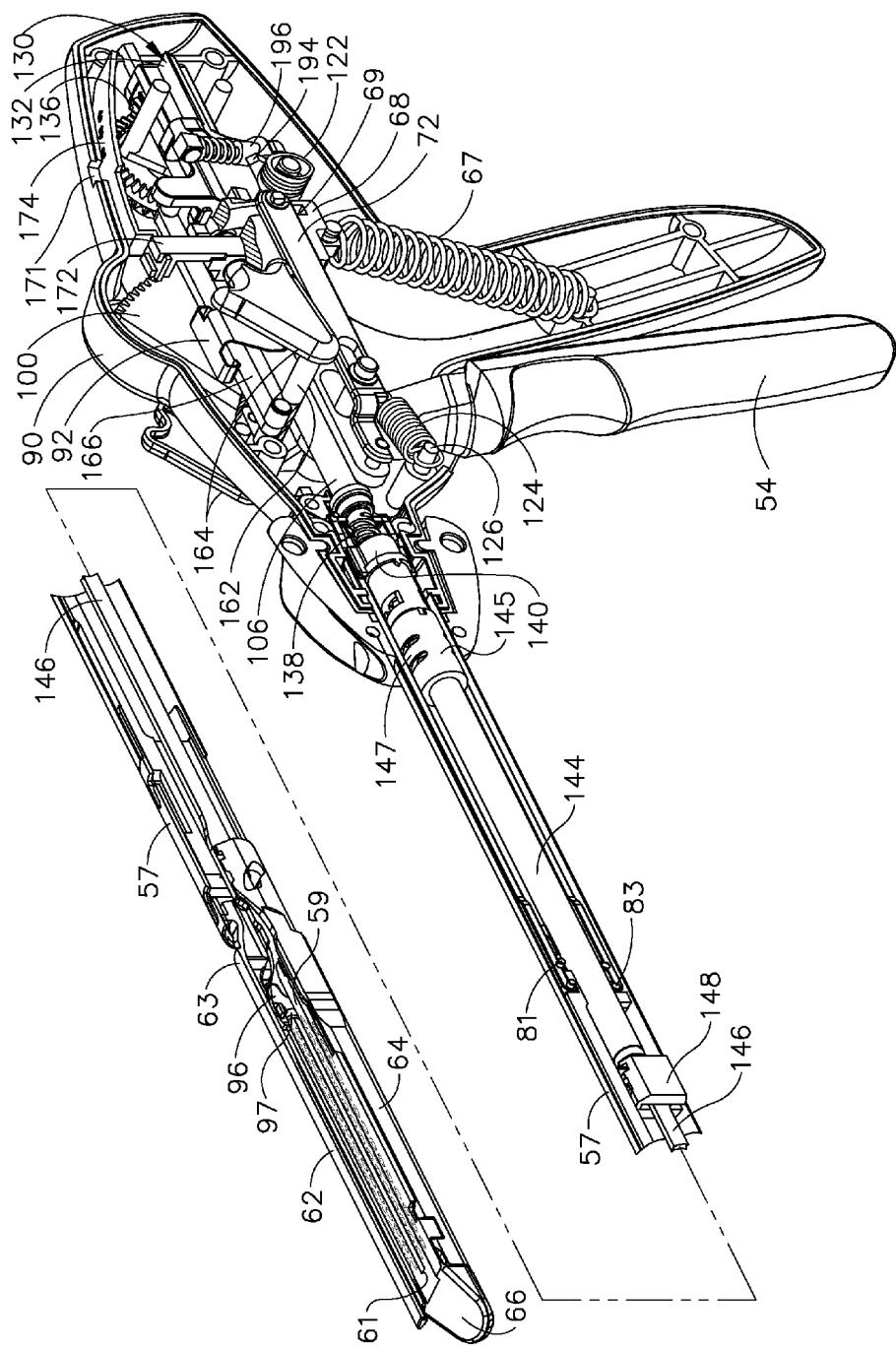
FIG. 18 is a perspective view of the surgical instrument of FIG. 1 illustrating the configuration of the surgical instrument upon the seventh actuation of the trigger with the cutting member fully retracted.
Figure 19:
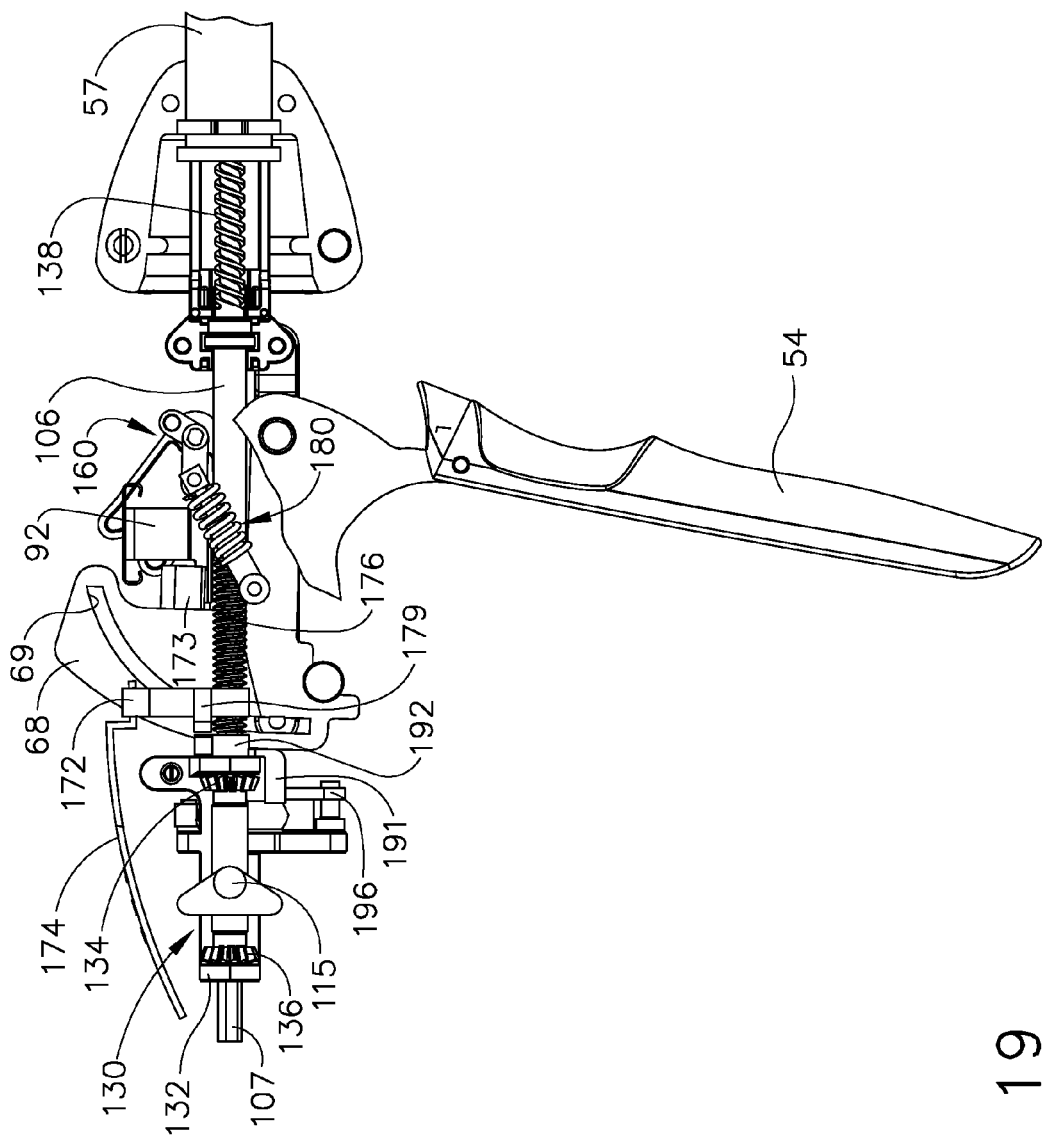
FIG. 19 is a partial elevational view of the surgical instrument of FIG. 1 illustrated in the configuration of FIG. 18 with components of the surgical instrument removed.

In order to retract cutting member 96, as outlined above, gear carriage 130 can be shifted such that forward gear 134 is disengaged from bevel gear 114 and, referring to FIGS. 17 and 18, reversing gear 136 is engaged with bevel gear 114. Thereafter, subsequent actuations of trigger 54 can rotate drive shaft 106 in the opposite direction and translate firing nut 140 proximally. More particularly, owing to the threaded engagement between firing nut 140 and threaded portion 138 of drive shaft 106, the rotation of shaft 106 in the opposite direction applies a reactional force to firing nut 140 which displaces firing nut 140 in the proximal direction. Accordingly, firing rod 144, drive bar 146 and cutting member 96, which can be connected to firing nut 140 as described above, are also displaced in the proximal direction thereby retracting cutting member 96 within end effector 58. Similarly, the rotation of shaft 106 in the opposite direction can displace indictor nut 172 of indicator assembly 170 proximally as well. More particularly, the first actuation of trigger 54 after gear carriage 130 has been shifted, i.e., the fifth overall actuation of trigger 54, can cause drive shaft 106 to apply a reactional force to indicator nut 172 and move nut 172 proximally. In such circumstances, indicator nut 172 can move indicator plate 174 relative to window 171 such that the numeral '2' is visible through indicator window 171 which can remind the surgeon that two more actuations of trigger 54 are required to fully retract cutting member 96.

Although trigger 54 is actuated three times to advance and/or retract cutting member 96 in the present embodiment, the actuations required to advance cutting member 96 can be different than the actuations required to retract cutting member 96 in other embodiments. Exemplary embodiments including features for advancing and retracting cutting member 96 at different rates are described in detail further below. Furthermore, in at least one embodiment, portion 95 of cutting member 96 can be engaged with the staple driver such the retraction of cutting member 96 also retracts the staple driver. In other embodiments, however, the staple driver can be left behind in the staple cartridge and only the cutting member 96 is retracted. Such embodiments may be utilized where a spent staple cartridge assembly is replaced with a new staple cartridge assembly which includes its own staple driver therein and, as a result, it may be desirable to leave the used staple driver in the spent cartridge.

In order to motivate gear carriage 130 as described above, surgical instrument 50 can include, referring to FIGS. 3-5, switching mechanism 160. In at least one embodiment, switching mechanism 160 can include shaft switch 162, shifter handles 164 extending therefrom, and shifter link 166, where shifter link 166 can be connected to shaft 162 via shifter pin 169 and gear carriage housing 132 via pin 168. In order to slide gear carriage 130 relative to drive shaft 106 as described above, shifter handles 164 can be configured to rotate shaft 162 such that crank arm 163 extending from shaft 162 displaces shifter link 166 and drives gear carriage 130 along axis 105 of drive shaft 106. In the illustrated embodiment, when shifter handles 164 are oriented in a substantially downward direction, as illustrated in FIG. 8, crank arm 163 is oriented in a substantially upward direction. In this configuration, referring to FIG. 5, gear carriage 130 is positioned in its most rearward, or proximal, position such that forward gear 134 is operably engaged with bevel gear 114. In order to shift surgical instrument 50 into a configuration in which cutting member 96 is retracted, shifter handles 164 can be rotated upwardly, as illustrated in FIG. 17, to rotate crank arm 163 forward, or distally. Correspondingly, crank arm 163 can be configured to displace link arm 166 distally and pull gear carriage 130 into its most distal position, thereby engaging reversing gear 136 with bevel gear 114. In the event that the surgeon desires to advance cutting member 96 after at least partially retracting cutting member 96, the surgeon can rotate shifter handles 164 downwardly and re-engage forward gear 134 with bevel gear 114.

In various embodiments, referring to FIGS. 3 and 5, surgical instrument 50 can further include a bistable compliant mechanism for biasing switching mechanism 160 into a configuration where one of gears 134 or 136 is engaged with bevel gear 114. Stated another way, the bistable compliant mechanism can cause switching mechanism 160 to become dynamically unstable when a surgeon only partially rotates shifter handles 164. In such circumstances, the bistable compliant mechanism can bias switching mechanism 160 into one of two configurations where it is stable, i.e., the forward and reversing configurations. In various embodiments, bistable compliant mechanism 180, referring primarily to FIG. 3, can include receiver 182, spring 184, plunger 186 and toggle pin 188. In at least one embodiment, toggle pin 188 can connect plunger 186 to switch shaft 162 and receiver 182 can be connected to projection 183 extending from housing 90. In use, spring 184 can be configured to apply a biasing force to shaft 162 via plunger 186 and can be configured to rotate shaft 162 in the event that shaft 162 is only partially rotated between its forward and reversing orientations.

In various embodiments, once cutting member 96 has been fully retracted, the end effector closing system and the staple firing system can be reset so that the spent staple cartridge can be removed from surgical instrument 50, a new staple cartridge 66 can be positioned within staple cartridge channel 64, and surgical instrument 50 can be used to further staple and cut tissue as described above. In the illustrated embodiment, cam 68 can be released from lock 92 to open anvil 62 and reset the end effector closure system. Similarly, ratchet gear 108 can be disengaged from main drive gear 110 to disengage trigger 54 from gear train 102 and reset the staple firing system. In at least one embodiment, cam 68 and ratchet gear 108 can be manually reset, however, referring primarily to FIGS. 3-5, 9, 10, 19 and 20, surgical instrument 50 can include a reset system which can automatically reset the end effector closure system and staple firing system described above. In various embodiments, the final return actuation of trigger 54 can reset these systems as described in detail below.

As outlined above, the first actuation of trigger 54 can rotate cam 68 into the position illustrated in FIG. 8 and spring lock 92 can be configured to hold cam 68 in place as the firing drive is operated by subsequent actuations of trigger 54. As also illustrated in FIG. 8, surgical instrument 50 can further include cam spring 67 which can be configured to bias cam 68 downwardly and, referring to FIGS. 9 and 10, hold cam lock arm 73 extending from cam 68 against spring lock 92. In such embodiments, cam lock arm 73 can include recess 74 which can be configured to receive at least a portion of spring lock 92. In order to assist cam spring 67 in keeping cam 68 from lifting upwardly during subsequent actuations of trigger 54 and becoming disengaged from cam spring 92, indicator nut 174 can be configured to contact cam rail 75 and hold cam lock arm 73 against spring lock 92. More particularly, as indicator nut 174 is advanced distally, as described above, indicator nut 174 can be slid along contact rail 75 providing a positive stop against which cam 68 cannot rotate. Once indicator nut 174 is returned to its most proximal position, however, indicator nut 174 can become aligned with ramp 89 and, as a result, the third return actuation of trigger 54 can cause cam 68 to rotate upward slightly, thereby disengaging lock arm 73 from spring lock 92 as illustrated in FIG. 10.

After cam 68 has been released from lock 92, cam return spring 67 can be configured to rotate cam 68 downwardly and return it to its original position. As cam 68 is rotated downwardly, the walls of cam slot 69 can be configured to drive closure links 72 distally and, correspondingly, drive channel portions 78 and 80 and staple cartridge channel 64 distally as well. In at least one embodiment, end effector 58 can further include a spring (not illustrated) configured to bias anvil 62 upwardly as staple cartridge channel 64 is slid distally, i.e., away from outer sheath 57 of elongate shaft assembly 56. In other various embodiments, although not illustrated, surgical instrument 50 can further include an actuator in which a surgeon can operate to pull or push anvil 62 into an open position. In either event, in at least one embodiment, cam return spring 67 can assert a force sufficient for cam 68 to displace ratchet gear 108 out of engagement with main drive gear 110 and, as a result, reset the firing drive. In other various embodiments, cam return spring 67 may not be strong enough to pull cam 68 downwardly with sufficient force to disengage ratchet gear 108 from main drive gear 110. In at least one such embodiment, surgical instrument 50 can further include, referring to FIGS. 3-5 and 19, a toggle switch assembly which can selectively bias ratchet gear 108 away from main drive gear 110.

Figure 9:
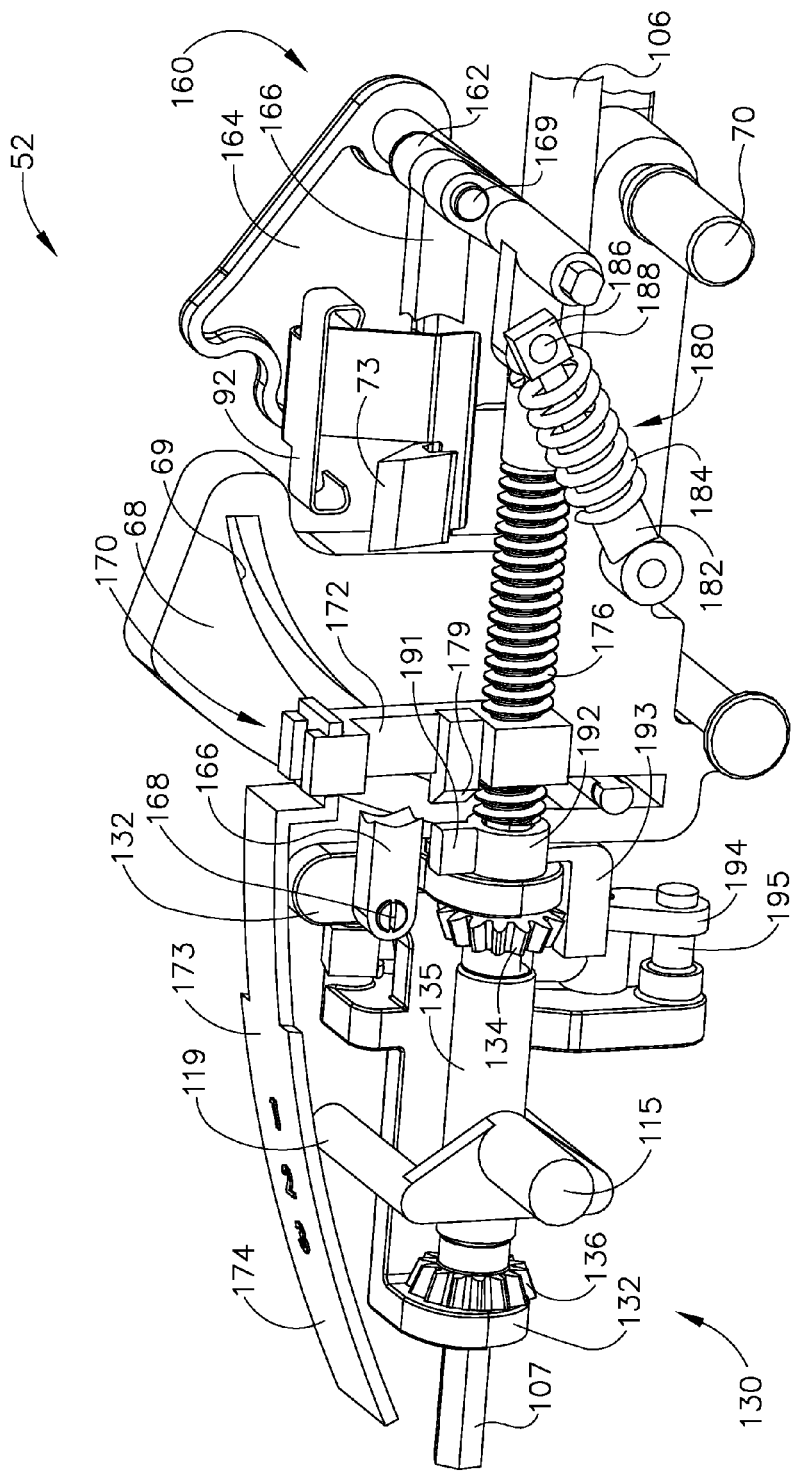
FIG. 9 is a partial perspective view of the surgical instrument of FIG. 1 in the configuration illustrated in FIG. 8 with some components of the surgical instrument removed.
Figure 11:
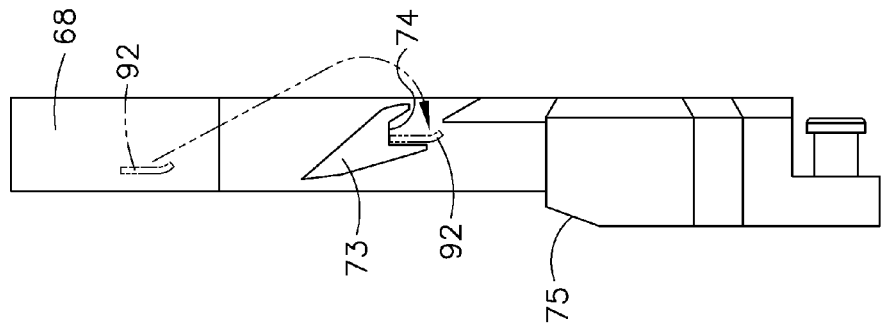
FIG. 11 is an elevational view of the cam of FIG. 10 illustrating various relative positions of a lock of the anvil closure system.
Figure 10:
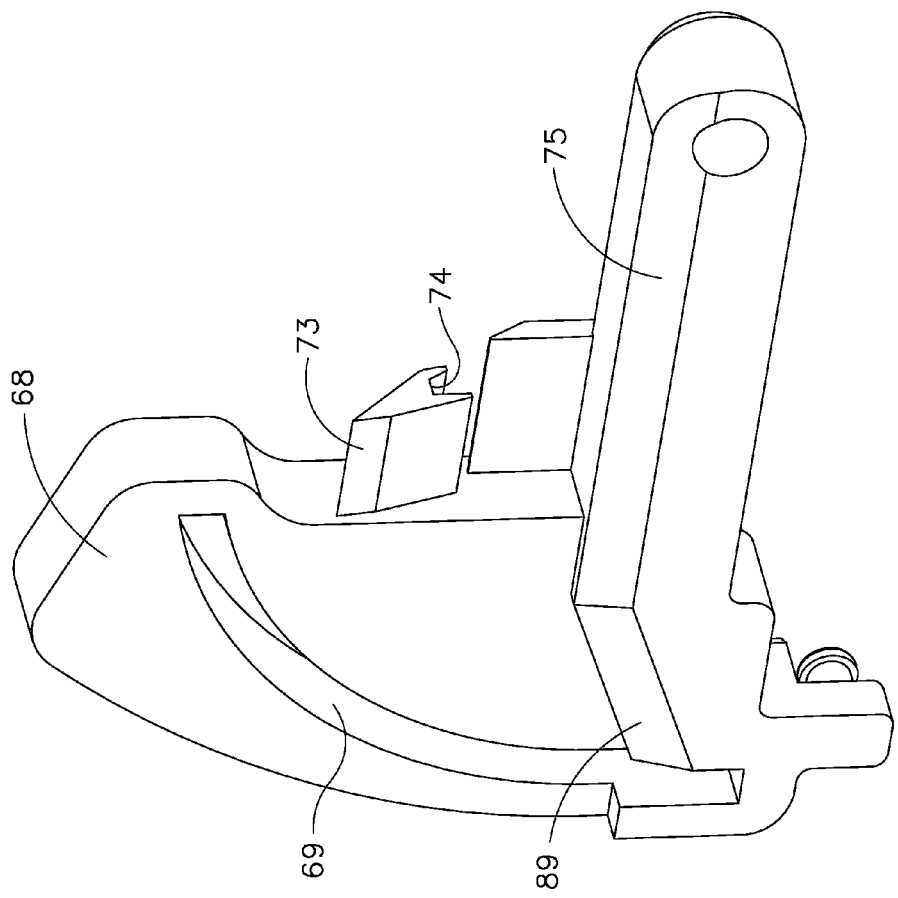
FIG. 10 is a perspective view of a cam of the end effector closure system of the surgical instrument of FIG. 1.
Figure 12:
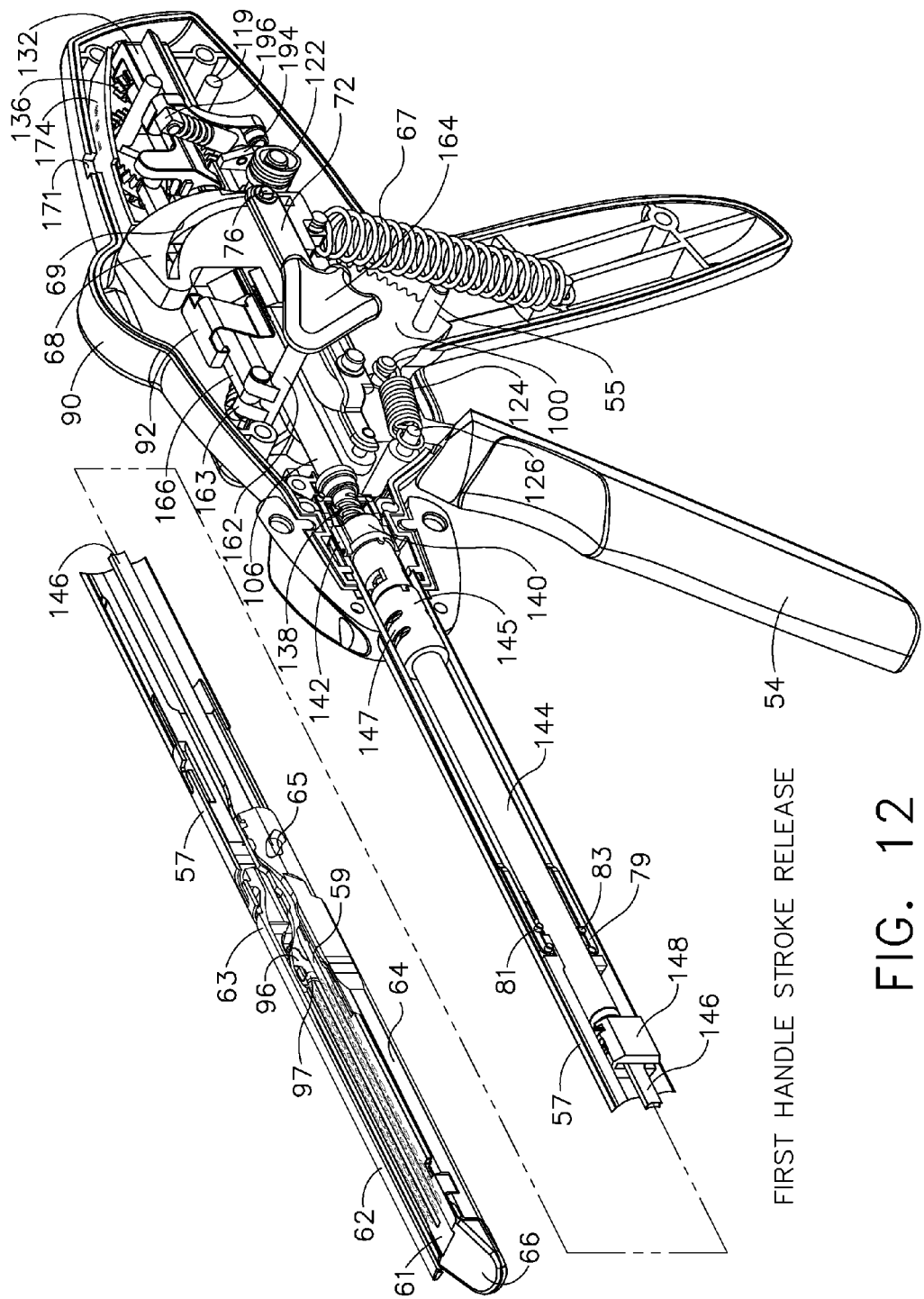
FIG. 12 is a perspective view of the surgical instrument of FIG. 1 illustrating the configuration of the surgical instrument after the trigger has been released after the first actuation of the trigger.
Figure 13:
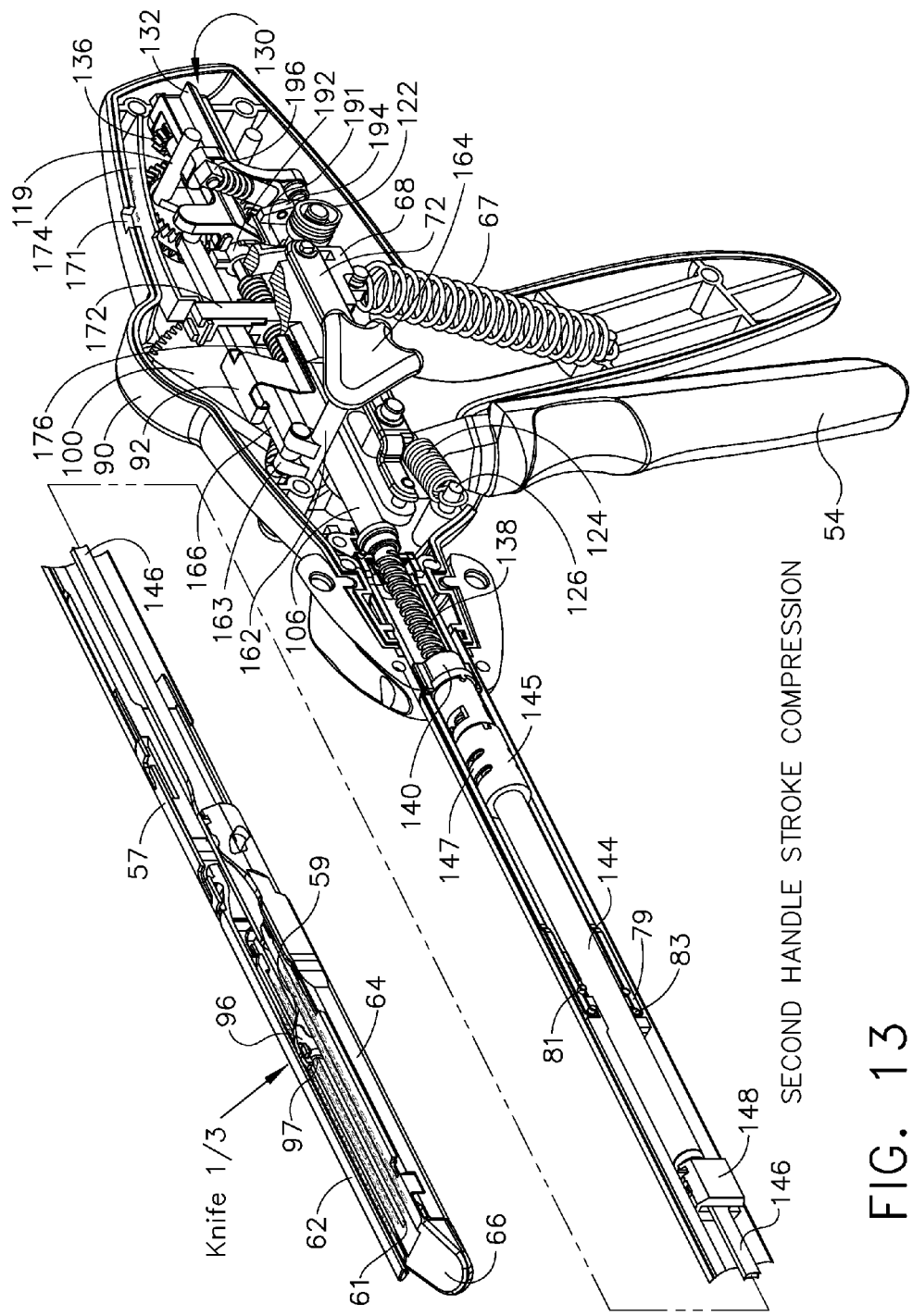
FIG. 13 is a perspective view of the surgical instrument of FIG. 1 illustrating the configuration of the surgical instrument upon the second actuation of the trigger.
Figure 14:
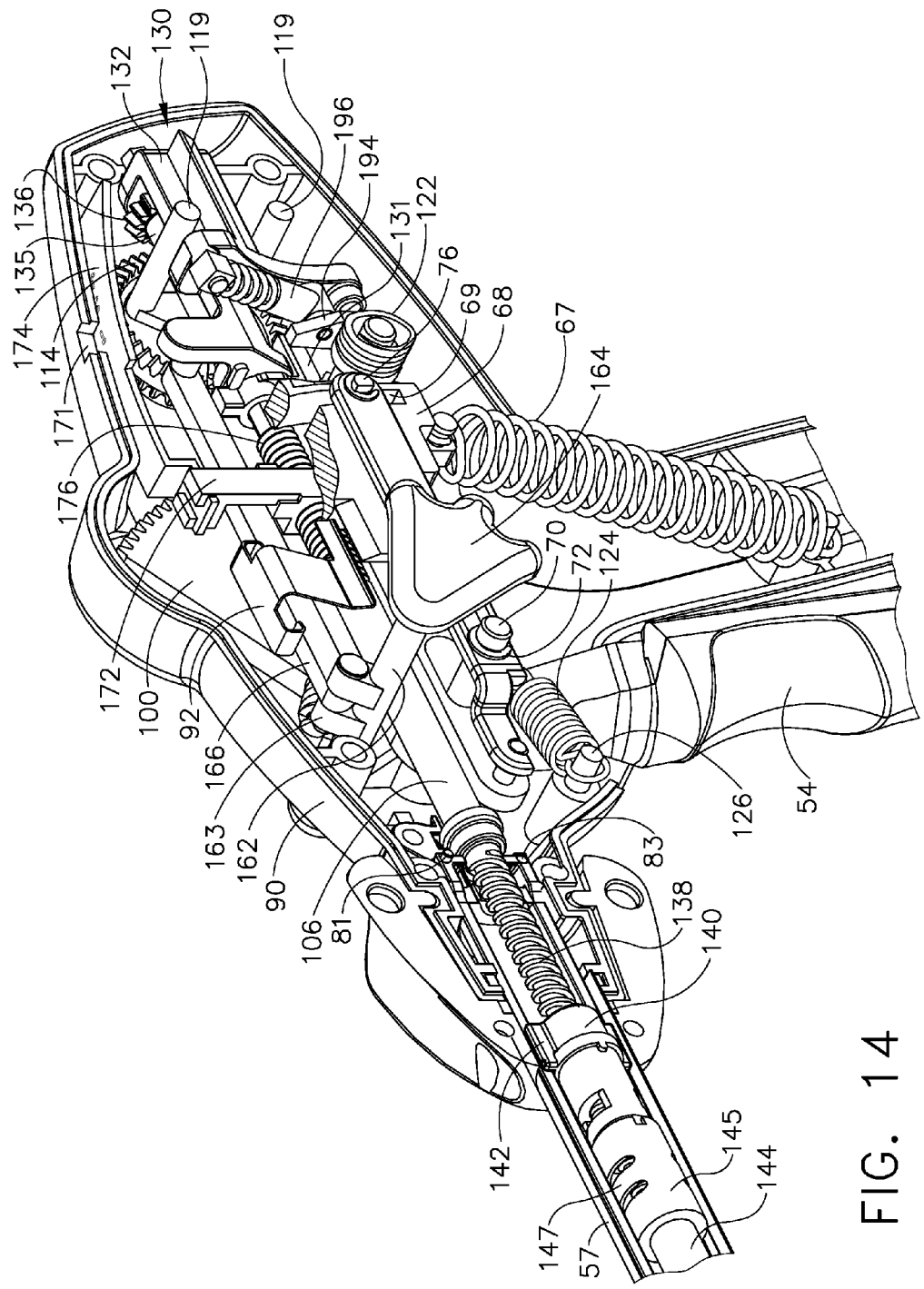
FIG. 14 is a partial perspective view of the surgical instrument of FIG. 1 in the configuration illustrated in FIG. 13.
Figure 15:
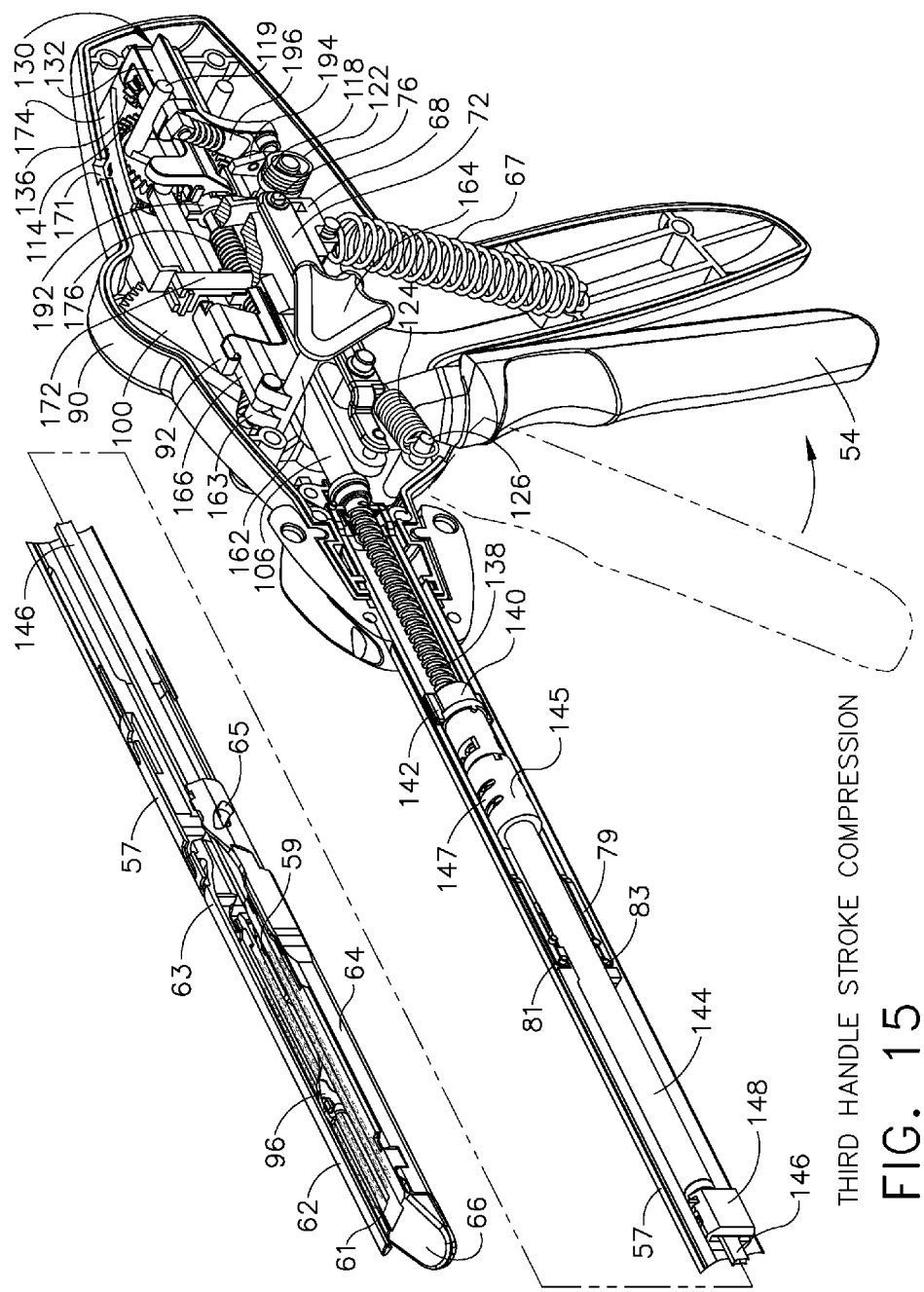
FIG. 15 is a perspective view of the surgical instrument of FIG. 1 illustrating the configuration of the surgical instrument upon the third actuation of the trigger.
Figure 16:
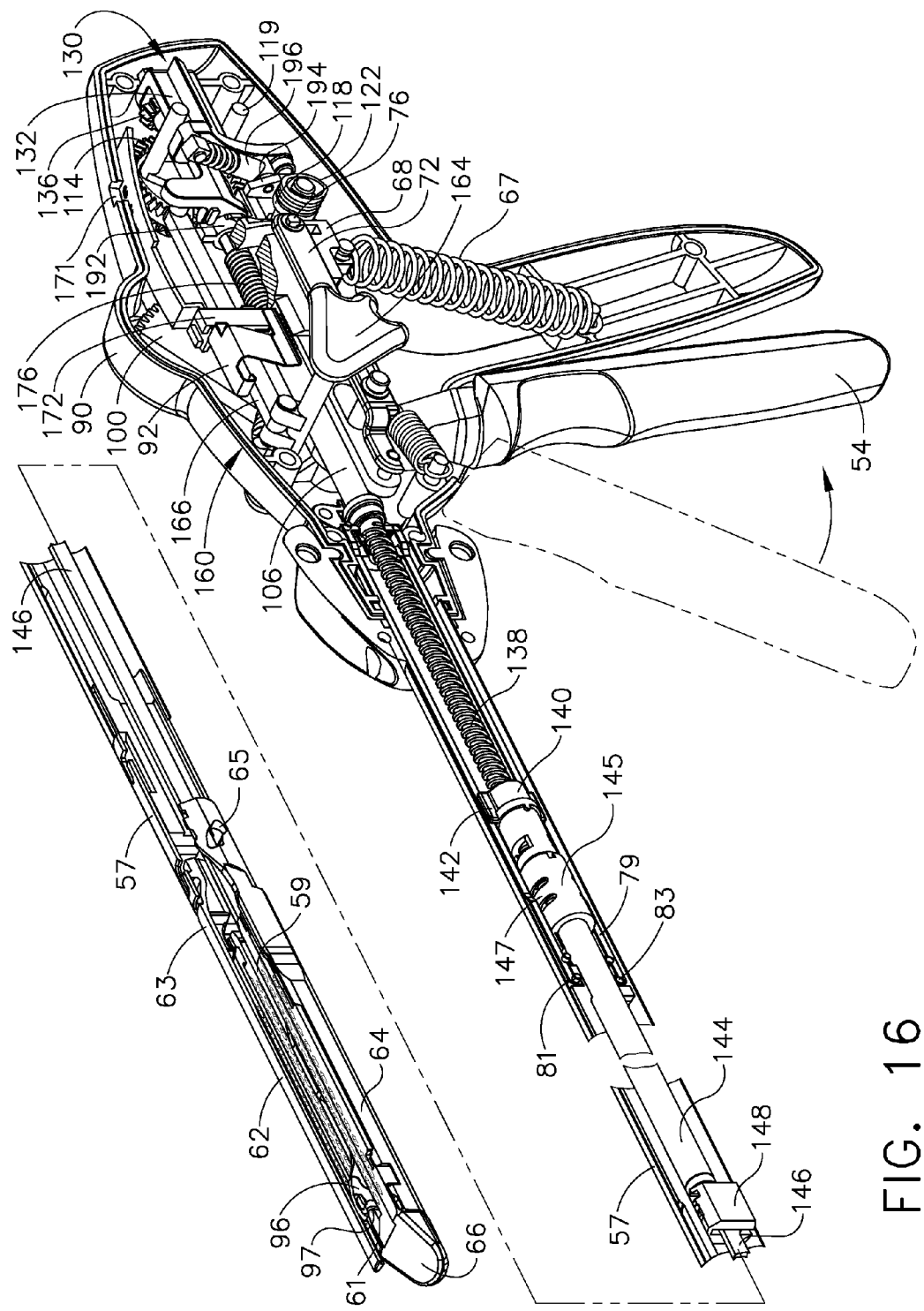
FIG. 16 is a perspective view of the surgical instrument of FIG. 1 illustrating the configuration of the surgical instrument upon the fourth actuation of the trigger.

In various embodiments, referring primarily to FIGS. 3, 4, and 9, toggle switch assembly 190 can include toggle actuator 192 mounted to drive shaft 106, where toggle actuator 192 can include toggle arm 193 extending therefrom. Upon the final return actuation of trigger 54, in at least one embodiment, indicator nut 172 can contact toggle actuator 192 and rotate it about drive shaft 106 such that toggle arm 193 is rotated toward ratchet gear 108. In at least one such embodiment, referring to FIG. 9, indicator nut 172 can further include ramp 179 which can be configured to engage projection 191 extending from toggle actuator 192 and rotate toggle actuator 192 clockwise about drive shaft 106. In various embodiments, toggle arm 193 can be configured to contact ratchet gear 108 as it is rotated about drive shaft 106 and displace ratchet gear 108 away from main drive gear 110. In at least one embodiment, ratchet gear 108 can be sufficiently displaced away from drive gear 110 to allow cam return spring 67 to position cam 68 adjacent collar 118. Thereafter, cam 68 can hold ratchet gear 108 in this position until cam 68 is rotated upwardly as described above.

Figure 20:
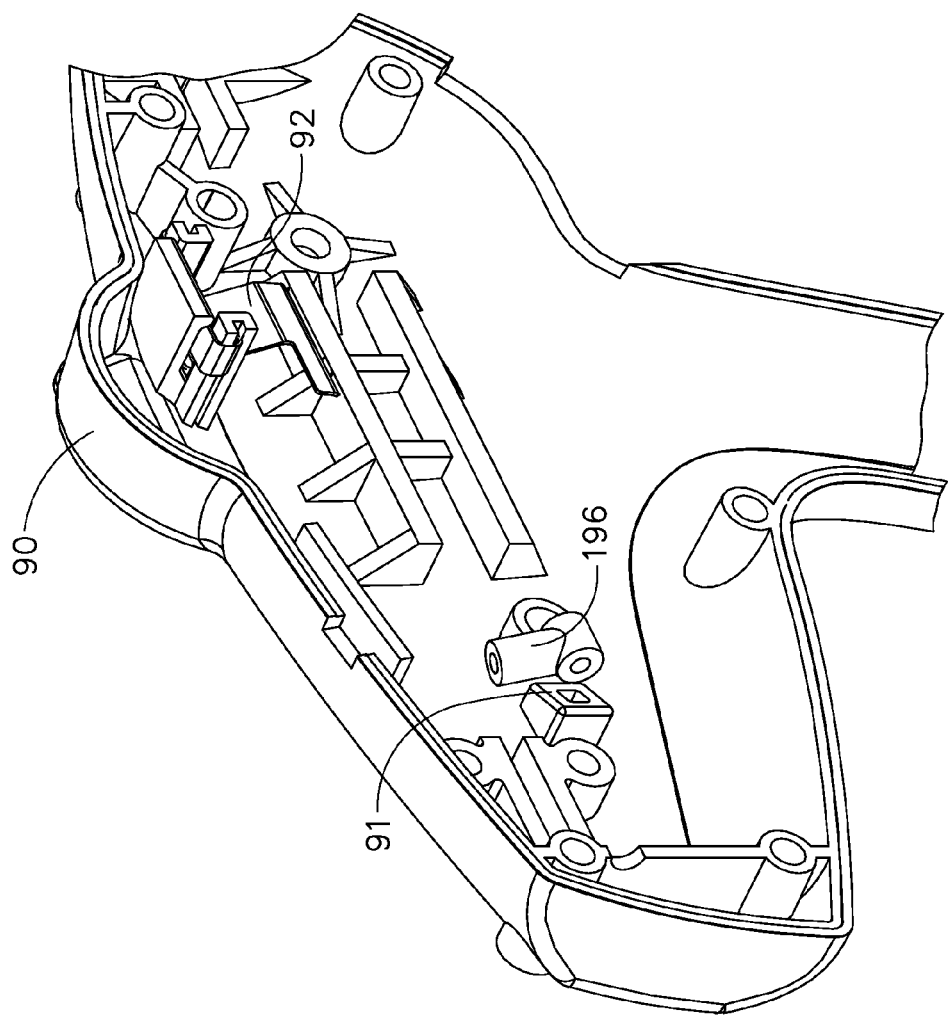
FIG. 20 is a partial perspective view of the housing of the surgical instrument of FIG. 1 illustrating the interaction of the firing drive and the housing after the seventh actuation of the trigger.

Although the above-described mechanisms can reset cam 68 and ratchet gear 108 into their initial positions, toggle arm 193 of toggle actuator 192, at least in the illustrated embodiment, can remain positioned against collar 118 of ratchet gear 108. Accordingly, even if cam 68 is rotated upwardly such that groove 120 is aligned with collar 118 upon the first actuation of trigger 54, ratchet gear 108 may not be released to engage main drive gear 110 as described above. In view of this, in at least one embodiment, surgical instrument 50 can include a reset mechanism for rotating toggle arm 193 out of engagement with ratchet gear 108. Such a mechanism can, in various embodiments, be manually operated and/or automatically operated in response to an actuation of trigger 54, for example. In at least one embodiment, as illustrated in FIG. 20, housing 90 can include projection 91 extending therefrom which can be configured to rotate toggle actuator 192 about drive shaft 106 and return it to its original, unactuated position as illustrated in FIG. 9. More particularly, in various embodiments, projection 91 can be configured to engage toggle link 194 (FIG. 3) as gear carriage 130 is moved from its distal position in which reversing gear 136 is engaged with bevel gear 114 to its proximal position in which forward gear 134 is engaged with bevel gear 114. Such movement can be effected by switching mechanism 160 when shifter handles 164 are rotated downwardly to move gear carriage 130 proximally and place surgical instrument 50 in its 'advancing' configuration described above. As a result of the contact between toggle link 194 and projection 91, toggle link 194 can be rotated about pin 195 such that toggle link 194 contacts actuator arm 193 and rotates toggle actuator 192 counterclockwise about drive shaft 106. In various embodiments, toggle switch assembly 190 can further include bistable compliant mechanism 196, which can assist in assuring that toggle switch assembly 190 does not become stuck in an intermediate configuration.

As described above, surgical instruments in accordance with the present invention can include a single trigger for actuating both an end effector closure system and a staple firing system. While the above-described features were described in connection with such single trigger surgical instruments, several of the features described above can be used in surgical instruments having a first trigger for actuating an end effector closure system and a second trigger for actuating a staple firing system. Referring to FIGS. 23-30, for example, surgical instrument 200 can include trigger 201 for actuating an end effector closure system and trigger 204 for actuating a staple firing system. In various embodiments, referring to FIG. 25, the end effector closure system can include closure link 203 operably engaged with closure trigger 201 via pin 209. The end effector closure system can further include slider 205 and closure tube 207 (FIG. 23), where closure tube 207 can be operably connected to closure link 203 via slider 205 and pin 211. More particularly, referring to FIG. 29, closure tube 207 can include flange 213 at its most proximal end which can be configured to be received within slot 215 in slider 205 such that the sliding motion of slider 205 is transmitted to closure tube 207.

Figure 29:
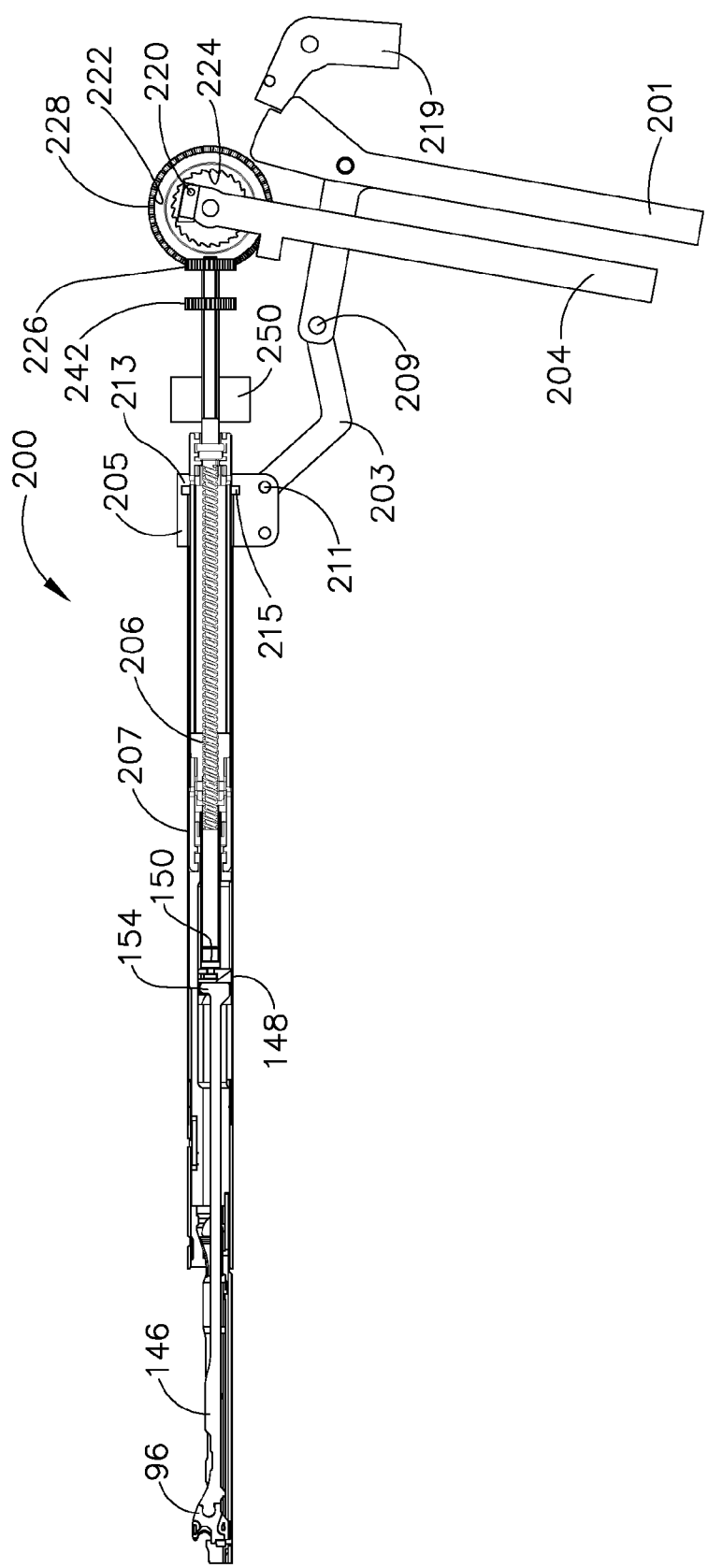
FIG. 29 is a side view of the surgical instrument of FIG. 23 configured to advance a cutting member within the end effector.
Figure 30:
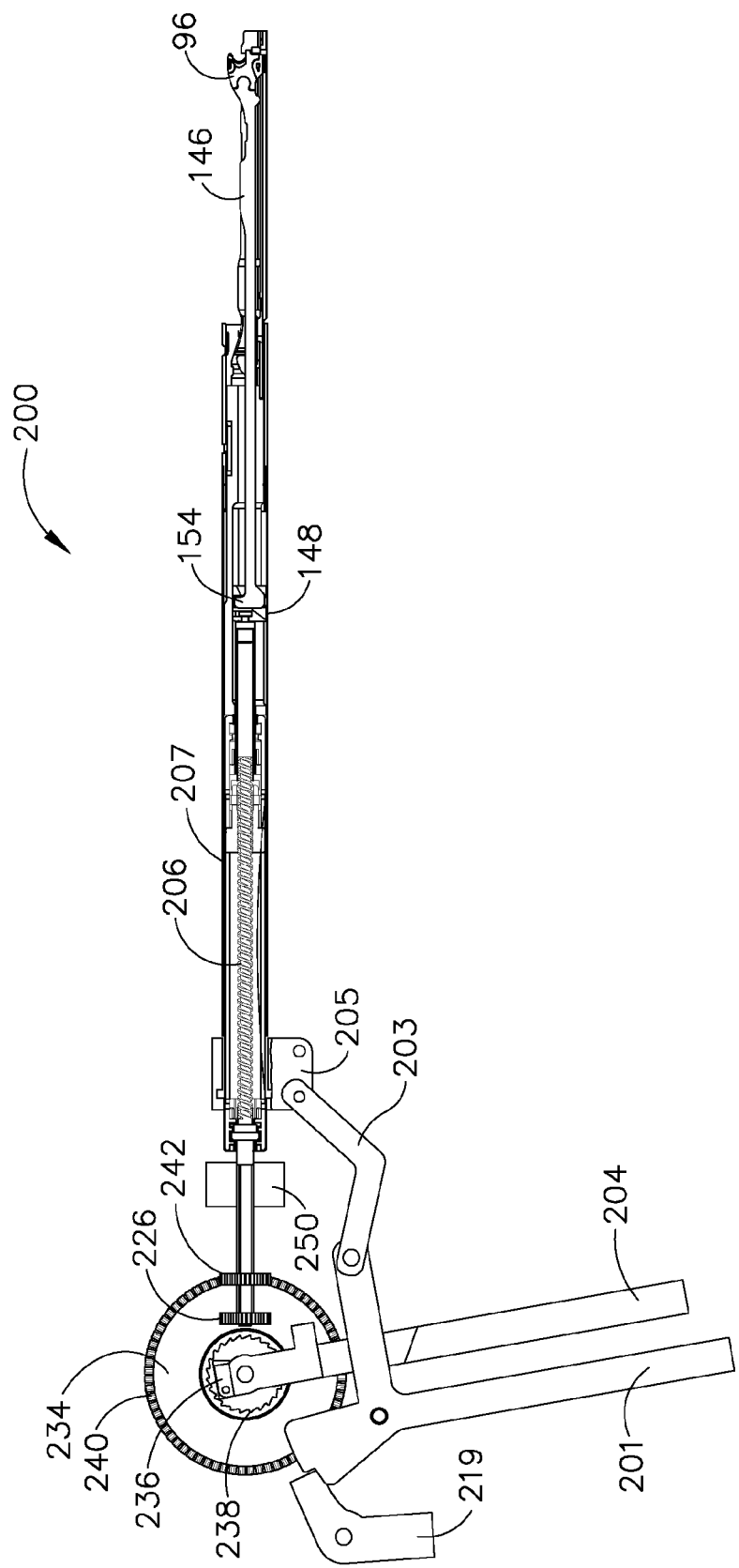
FIG. 30 is a side view of the surgical instrument of FIG. 23 configured to retract the cutting member within the end effector.

In use, referring primarily to FIGS. 29 and 30, the actuation of trigger 201 can translate closure link 203 distally and, correspondingly, translate slider 205 and closure tube 207 distally as well. In various embodiments, closure tube 207 can include features which are cooperatively engaged with anvil 62 such that translation of closure tube 207 causes anvil 62 to rotate toward staple cartridge channel 64. More particularly, referring to FIG. 24, anvil 62 can include projection 51 extending therefrom which can be received within aperture 217 of closure tube 207 such that sidewalls of aperture 217 can abut projection 51 and rotate anvil 62 downwardly. To guide anvil 62, as outlined above, staple cartridge channel 64 can include slots 65 which can define a path for anvil 62 as it is rotated. Surgical instrument 200 can further include lock 219 which can be configured to hold trigger 201 in an actuated position thereby holding anvil 62 in a closed position. To open anvil 62, lock 219 (FIG. 28) can be disengaged from trigger 201 such that trigger 201 can be returned to its unactuated position. As trigger 201 is returned to its unactuated position, trigger 201 can drive slider 205 and closure tube 207 proximally and, owing to the operative engagement between projection 51 and aperture 217, rotate anvil 62 upwardly.

As indicated above, surgical instruments in accordance with the present invention can include a firing drive which can be configured to advance a cutting member, for example, at a first rate and retract the cutting member at a different rate. In various embodiments, referring to FIGS. 23-30, surgical instrument 200 can include firing drive 202 which can comprise trigger 204, drive shaft 206, first ratchet assembly 210, and second ratchet assembly 212. In at least one embodiment, ratchet assemblies 210 and 212 can be configured to rotate drive shaft 206 in clockwise and counter-clockwise directions, respectively, in order to advance or retract cutting member 96 within end effector 58. In various embodiments, referring to FIG. 25, trigger 204 can be selectively engageable with ratchet assemblies 210 and 212 such that, when trigger 204 is actuated, only one of ratchet assemblies 210 and 212 is driven by trigger 204. In at least one such embodiment, trigger 204 can be slidable along pin 214 in order to engage trigger 204 with one of ratchet assemblies 210 and 212. In the illustrated embodiment, pin 214 can be rotatably received in apertures 216 in housing portions 218 and provide an axis of rotation for trigger 204.

Figure 25:
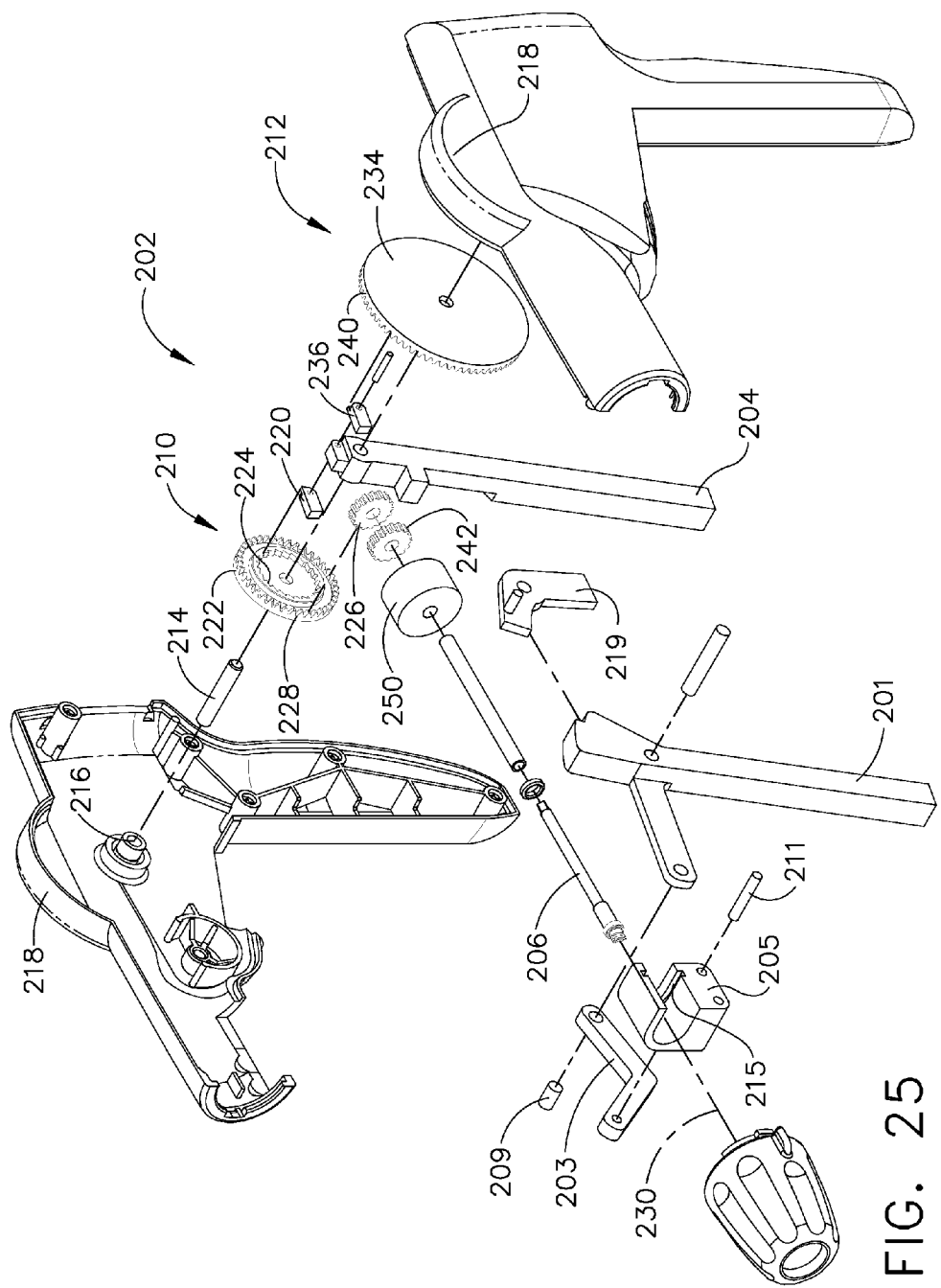
FIG. 25 is an exploded view of the handle portion of the surgical instrument of FIG. 23.
Figure 26:
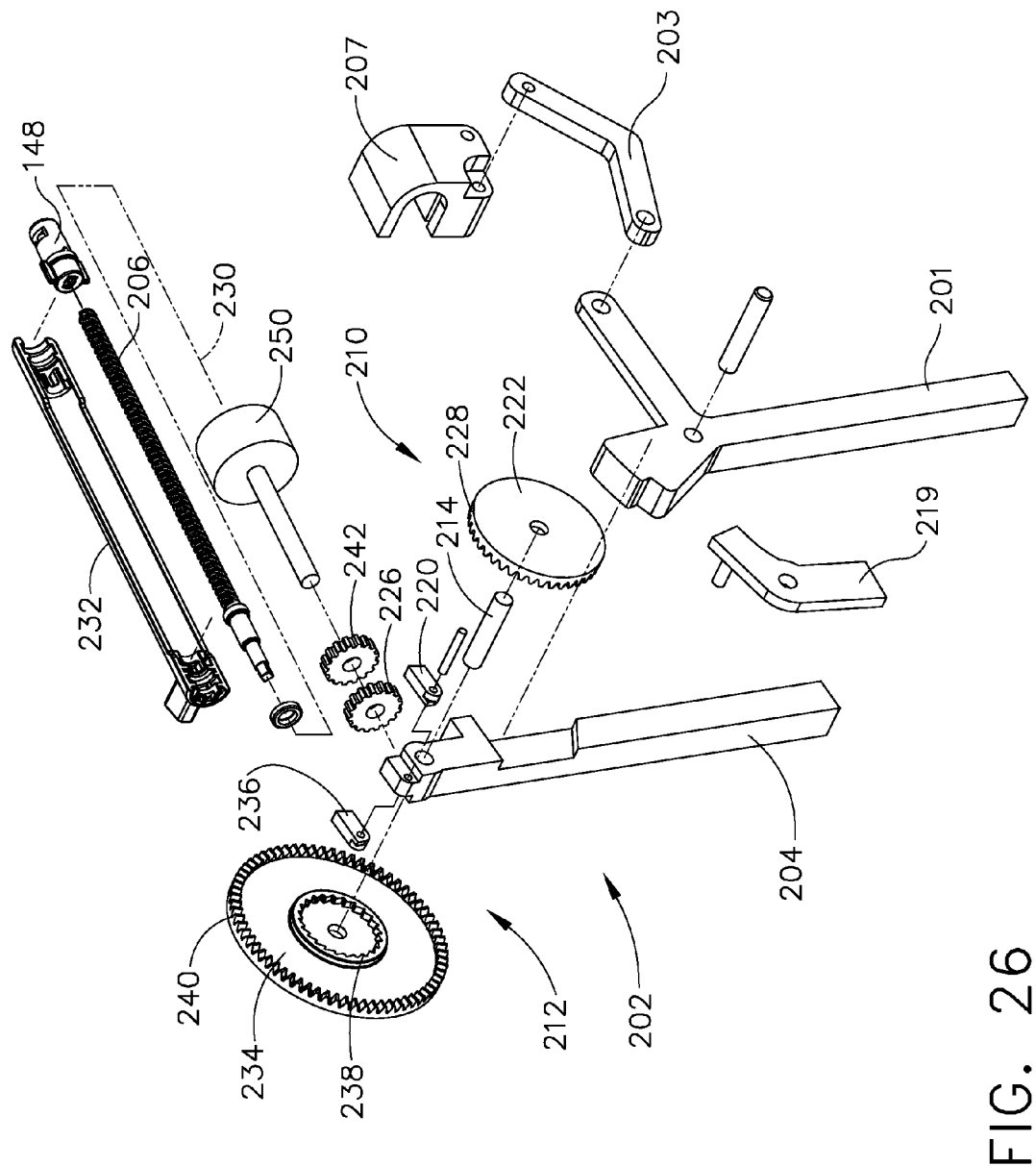
FIG. 26 is an exploded view of the surgical instrument of FIG. 23 with components of the surgical instrument removed.
Figure 27:
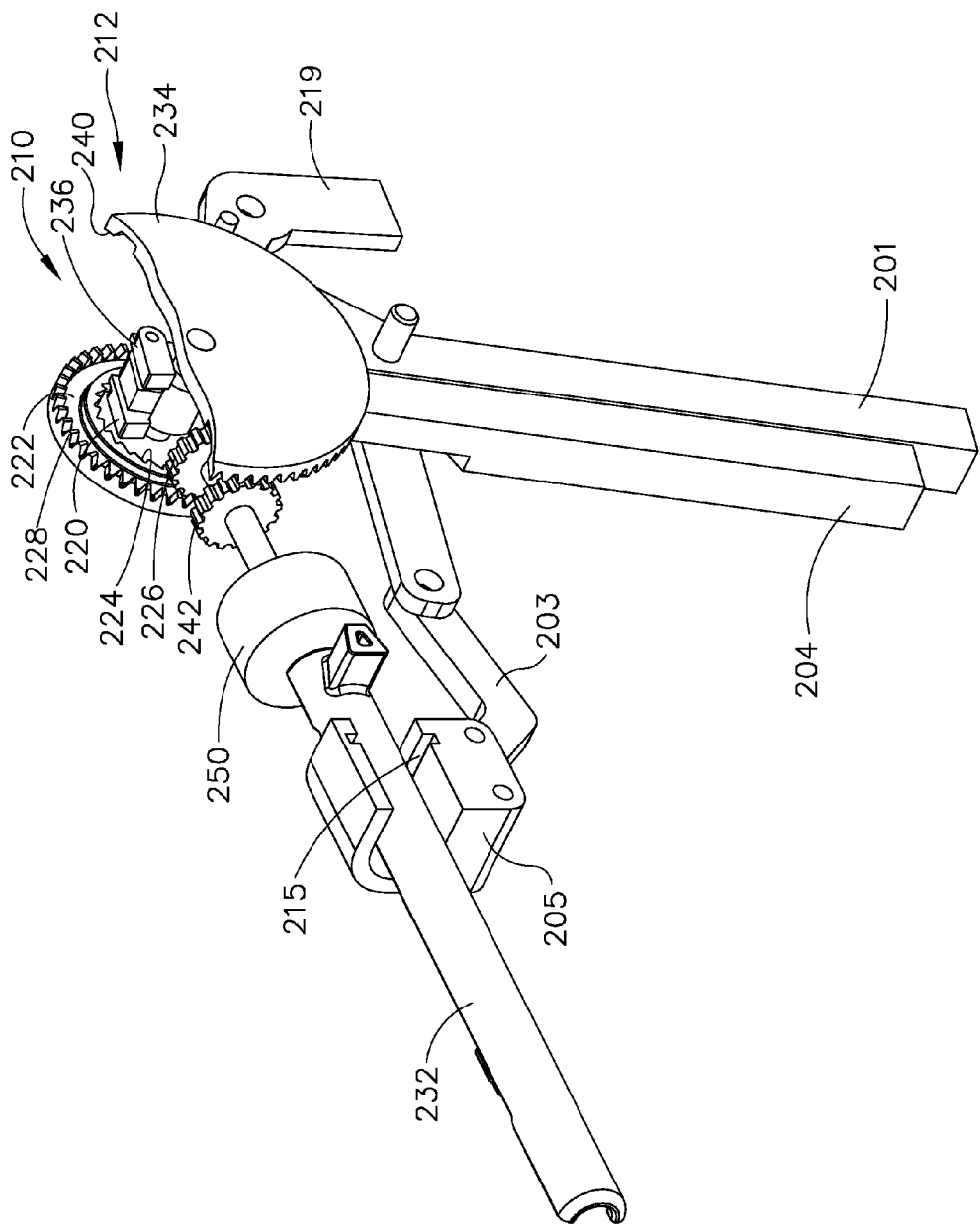
FIG. 27 is a perspective view of the surgical instrument of FIG. 23 with components of the surgical instrument removed.
Figure 28:
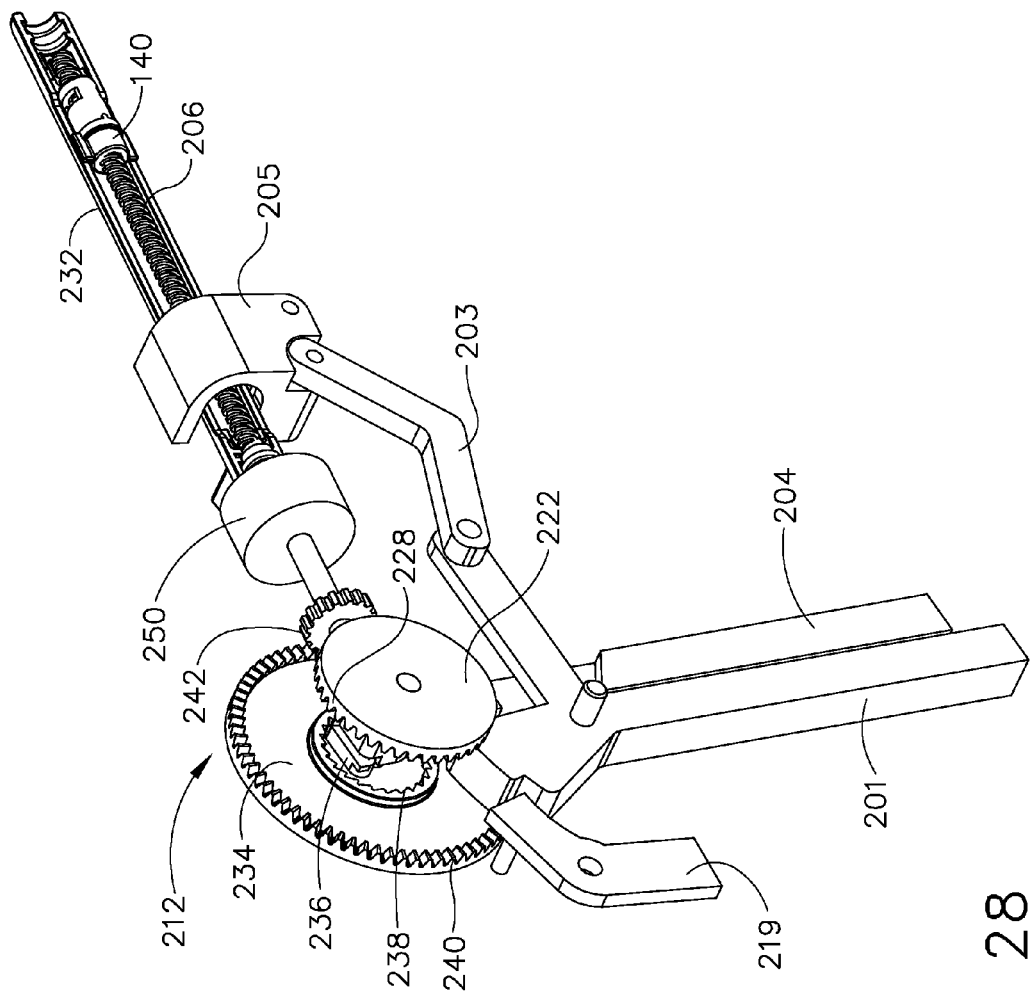
FIG. 28 is a second perspective view of the surgical instrument of FIG. 23 with components of the surgical instrument removed.

In various embodiments, referring to FIG. 27, trigger 204 can be positioned such that pawl 220, which can be pivotably mounted to trigger 204, is engaged with ratchet wheel 222 and, upon the actuation of trigger 204, ratchet wheel 222 is rotated about pin 214 by pawl 220. Upon the release of trigger 204, pawl 220 can slide over ratchet teeth 224 of ratchet wheel 222 permitting relative movement therebetween. In at least one embodiment, ratchet assembly 210 can further include a pawl spring (not illustrated) configured to bias pawl 220 into engagement with ratchet teeth 224 and re-engage pawl 220 with ratchet teeth 224 when trigger 204 is reactuated. In order to transmit the rotation of ratchet wheel 222 to drive shaft 206, drive shaft 206 can include forward gear 226 connected thereto. More particularly, in at least one embodiment, ratchet wheel 222 can further include gear teeth 228 which can be operably engaged with forward gear 226 such that the rotation of ratchet wheel 222 rotates forward gear 226 and drive shaft 206 about axis 230 (FIG. 25). In various embodiments, forward gear 226 can be press-fit, for example, onto drive shaft 206 or, in other various embodiments, forward gear 226 can be integrally formed with drive shaft 206.

In various embodiments, similar to the surgical instruments described above, drive shaft 206 can, referring to FIG. 24, be operably engaged with firing nut 140 in order to translate firing nut 140 within proximal retainer portion 232. As also described above, the translation of firing nut 140 can be transmitted to cutting member 96 via drive bar 146 in order to advance cutting member 96 within end effector 58. In order to retract cutting member 96 within end effector 58, in at least one embodiment, trigger 204 can be slid into engagement with second ratchet assembly 212 such that drive shaft 206 is rotated in the opposite direction when trigger 204 is actuated. Similar to ratchet assembly 210, referring to FIG. 28, ratchet assembly 212 can include ratchet wheel 234 and pawl 236 where pawl 236 can be pivotably mounted to trigger 204 and can be operatively engaged with ratchet wheel 234 via ratchet teeth 238. Similar to ratchet wheel 222, ratchet wheel 234 can include gear teeth 240 which can be operably engaged with reversing gear 242 mounted to drive shaft 206. As ratchet wheels 222 and 234 engage drive shaft 206 on substantially opposite sides, ratchet wheels 222 and 234 can rotate drive shaft 206 in opposite directions, i.e. clockwise and counterclockwise directions, respectively. Thus, in order to select whether cutting member 96 is advanced or retracted within end effector 58, trigger 204 can be slid into operative engagement with either first ratchet assembly 210 or second ratchet assembly 212.

In various embodiments, although not illustrated, first ratchet wheel 222 and second ratchet wheel 234 can have substantially the same diameter, or pitch radius. Stated another way, the distance between the center, or axis of rotation, of the ratchet wheels and the gear teeth of the ratchet wheels can be the same. In such embodiments, the distance that cutting member 96 is advanced per actuation of trigger 204 will be substantially the same distance that cutting member 96 is retracted per actuation of trigger 204. While suitable in some circumstances, such embodiments may require a surgeon to actuate trigger 204 several times before cutting member 96 is completely retracted. In view of the above, in various embodiments, first ratchet wheel 222 can have a pitch radius which is different than the pitch radius of second ratchet wheel 234. In at least one embodiment, second ratchet wheel 234 can have a larger pitch radius than first ratchet wheel 222 such that cutting member 96 is retracted a distance per actuation of trigger 204 which is greater than the distance that cutting member 96 is advanced per actuation of trigger 204. Stated another way, second ratchet assembly 212 can, at least in these embodiments, retract cutting member 96 at a rate which is greater than which it is advanced. In such embodiments, first ratchet assembly 210 can, owing to the slower advancing rate, provide a greater torque or advancing force to cutting member 96 while second ratchet assembly 212 can, owing to the faster retracting rate, reduce the time required for the surgeon to retract the cutting member.

While the term 'rate', as used above, is used to describe the distance that cutting member 96 can be advanced or retracted per actuation of trigger 204, the term 'rate' is not so limited. In at least one embodiment, the term 'rate' can be used to describe the velocity and/or acceleration in which the cutting member is moved. In such embodiments, it may be desirable to have a cutting member which is advanced at a lower velocity and/or acceleration to better control the cutting member and retracted at a greater velocity and/or acceleration to reduce the time required to retract the cutting member. Furthermore, while the illustrated embodiments include ratchet assemblies for providing the different advancing and retracting rates, the invention is not so limited. On the contrary, other embodiments are envisioned which include spur gear trains, bevel gears, and/or other motion transmission devices.

Figure 21:
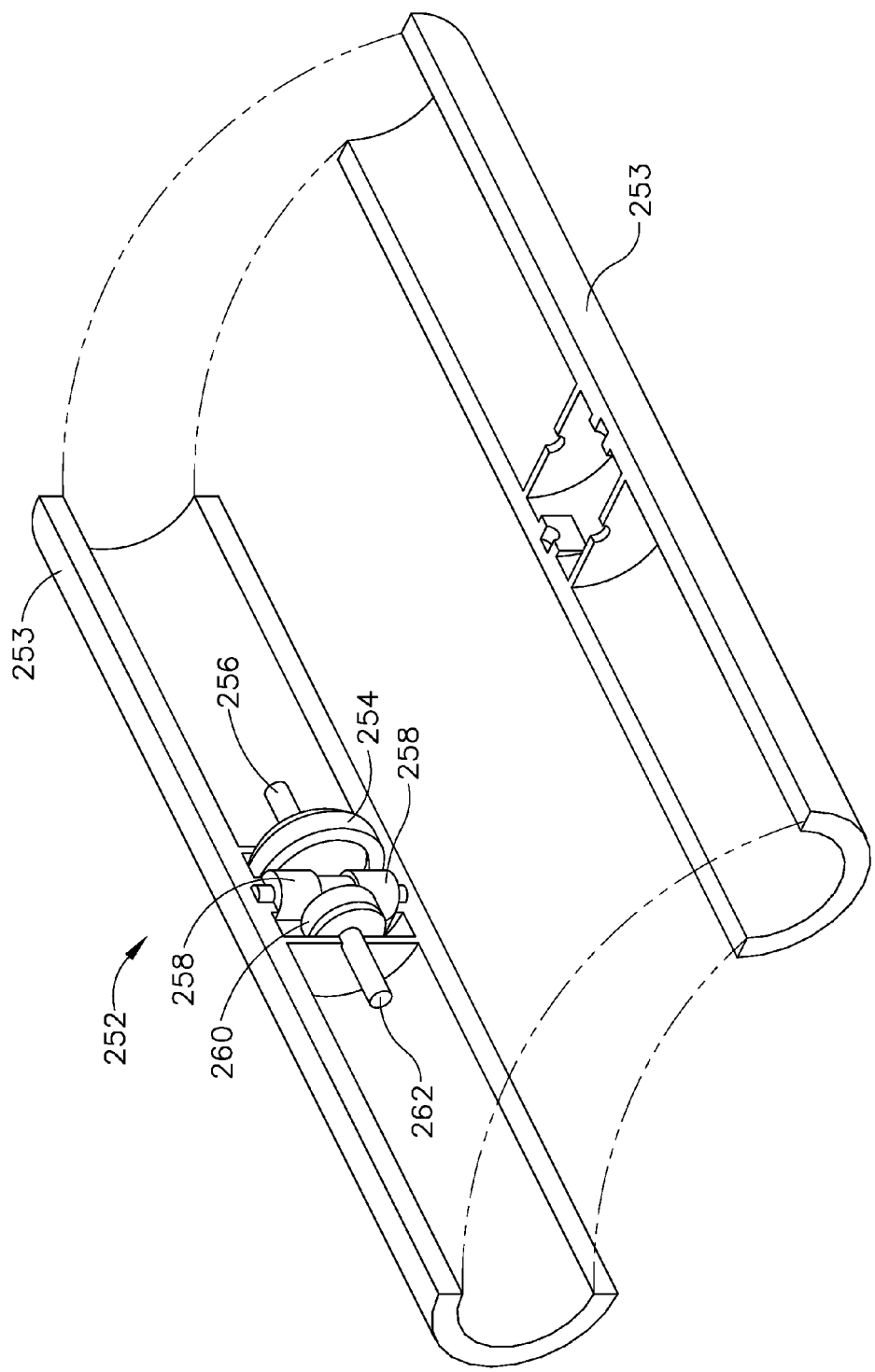
FIG. 21 is a perspective view of a gear reduction mechanism for a surgical instrument in accordance with an alternative embodiment of the present invention with a portion of the gear reduction housing disassembled.
Figure 22:
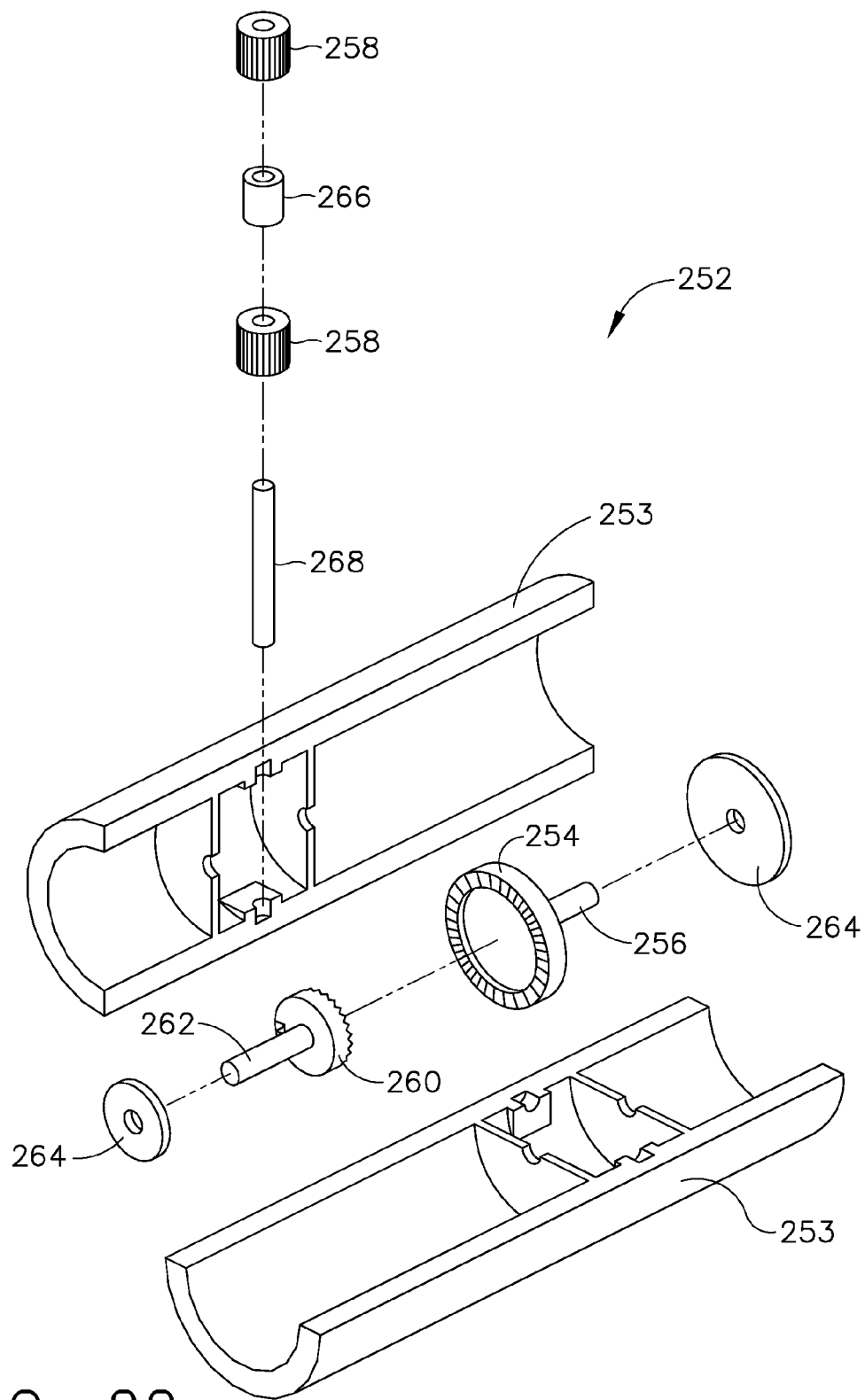
FIG. 22 is an exploded view of the gear reduction mechanism of FIG. 21.
Figure 23:
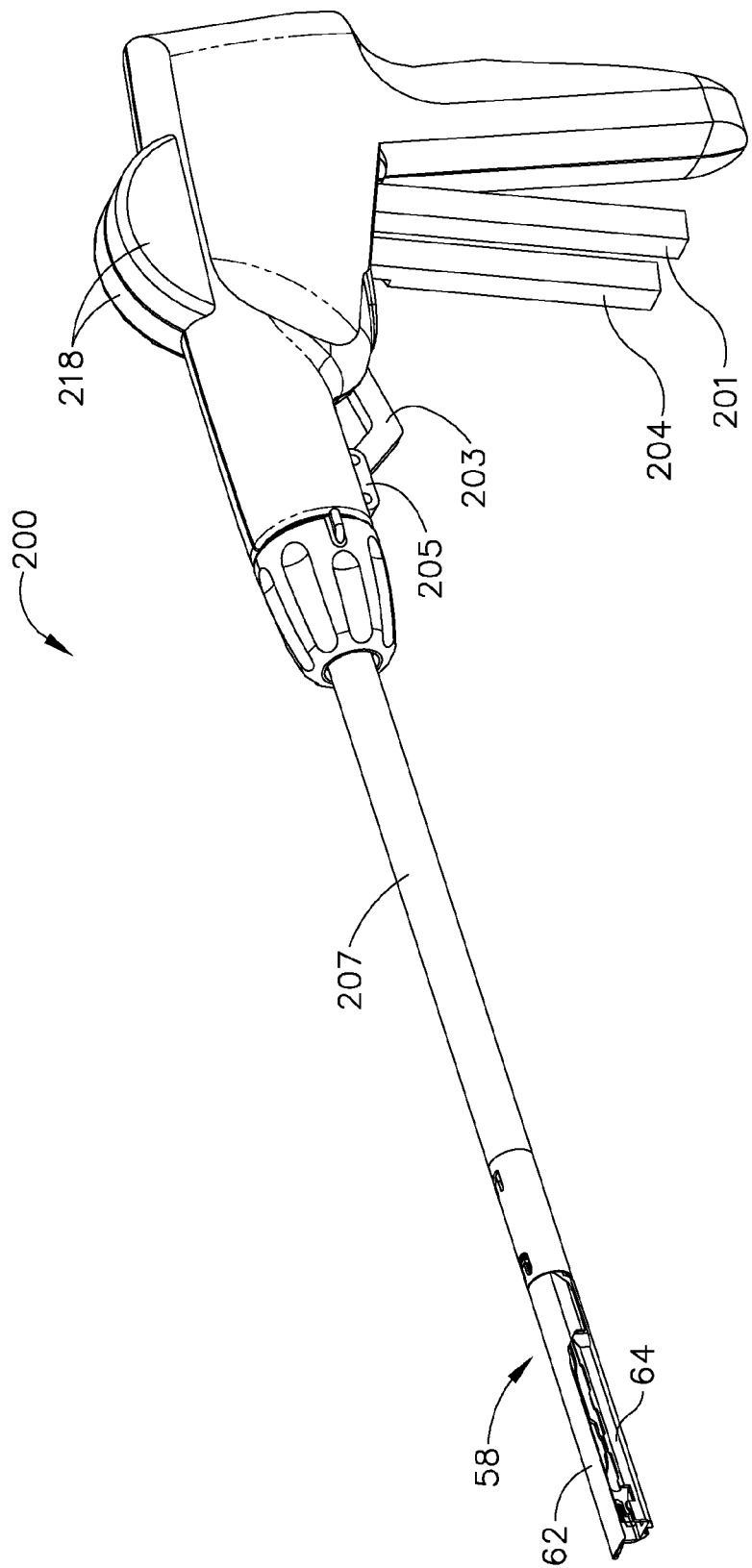
FIG. 23 is a perspective view of a surgical instrument in accordance with an alternative embodiment of the present invention.
Figure 24:
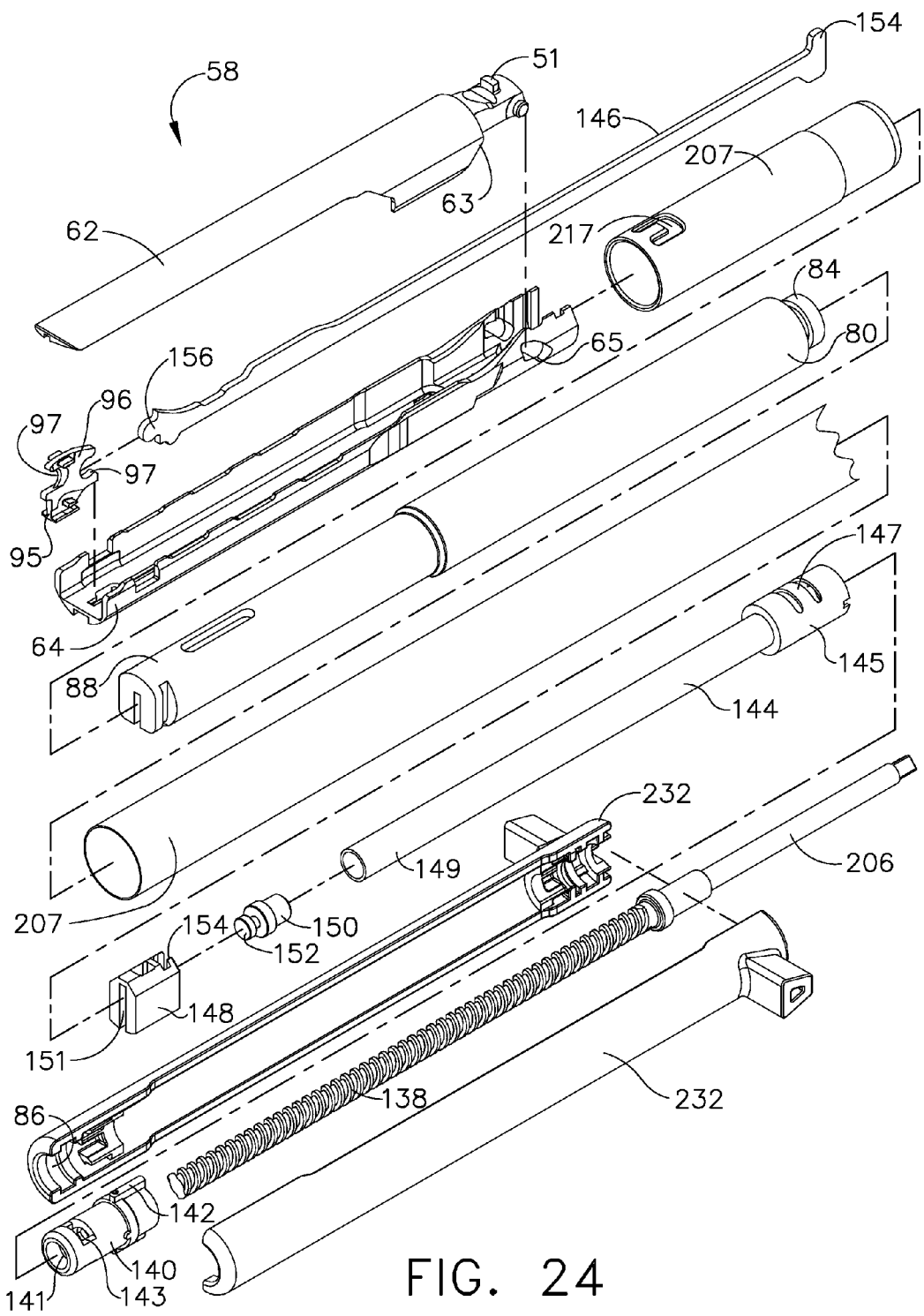
FIG. 24 is an exploded view of the end effector and shaft assembly of the surgical instrument of FIG. 23.

In various embodiments, surgical instruments in accordance with the present invention may include a gearbox for increasing or decreasing the rotational speed of the drive shaft. In at least one embodiment, referring to FIG. 25, surgical instrument 200 can further include gearbox 250 which can be operably positioned intermediate drive shaft 206 and ratchet assemblies 210 and 212. In various embodiments, gearbox 250 can be used to 'gear down' the speed of drive shaft 206 such that shaft 206 turns at a slower speed than if gearbox 250 were not utilized. In alternative embodiments, a gearbox can be used to 'gear up' the speed of drive shaft 206 such that drive shaft 206 turns at a faster speed. In at least one embodiment, gearbox 250 can include at least one set of planetary gears for changing the speed of drive shaft 206. In other various embodiments, a gearbox, such as gearbox 252 illustrated in FIGS. 21 and 22, can include housing 253, input gear 254 mounted to input shaft 256, pinion gears 258, and output gear 260 mounted to output shaft 262. In such embodiments, owing to the different pitch radii of input gear 254 and output gear 260, input shaft 256 and output shaft 262 will rotate at different speeds. To facilitate the rotational movement of gears 254, 258, and 260 within housing 253, gearbox 252 can further include various support plates 264, spacers 266, and pins 268 as illustrated in FIG. 22. In addition to the above, gearbox 252 can also be used to convert the clockwise motion of input shaft 256, for example, into counter-clockwise motion of output shaft 262.

In various embodiments described above, trigger 204 of surgical instrument 200 can be slid between a first position in which it is operatively engaged with first ratchet assembly 210 and a second position in which it is operatively engaged with second ratchet assembly 212. In at least one embodiment, firing drive 202 can be configured such that first pawl 220, for example, is disengaged from first ratchet wheel 222 before second pawl 236 is engaged with second ratchet wheel 234. In such embodiments, trigger 204 may be positioned in an intermediate position where it is not operably engaged with either first ratchet assembly 210 or second ratchet assembly 212. In various embodiments, as a result, firing drive 202 can be in a 'free' state where the actuation of trigger 204 does not result in the rotation of drive shaft 206. In alternative embodiments, firing drive 202 can be configured such that second pawl 236, for example, is engaged with second ratchet wheel 234 before first pawl 220 is operatively disengaged from first ratchet wheel 222. In such embodiments, trigger 204 may be positioned in an intermediate 'locked' state where trigger 204 cannot be actuated, thereby indicating to the surgeon that trigger 204 is not completely engaged with either one of the ratchet assemblies and trigger 204 requires further adjustment.

Figure 33:
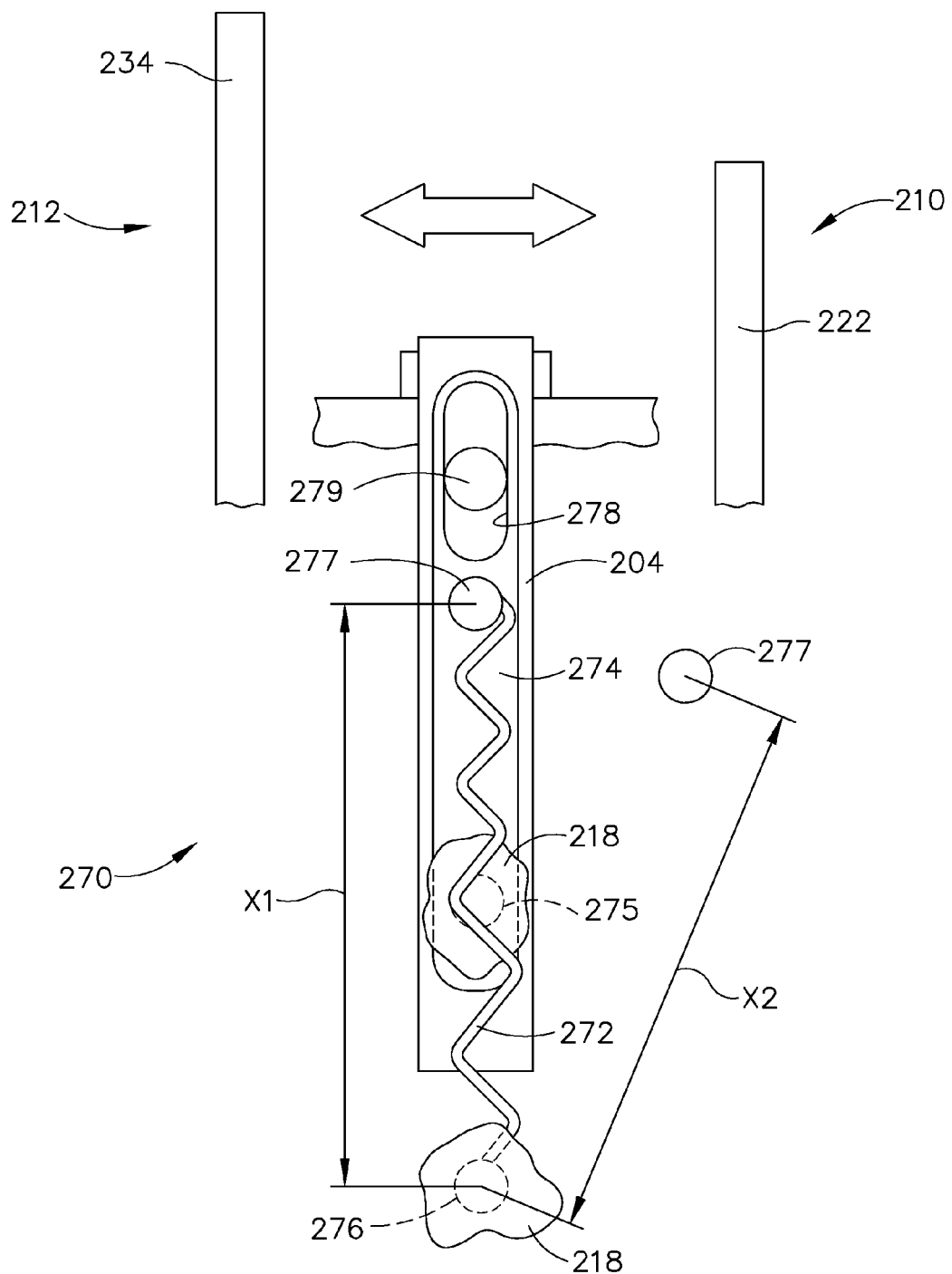
FIG. 33 is a diagram of a bistable compliant mechanism in accordance with an alternative embodiment of the present invention.

In various embodiments, surgical instrument 200 can include a device which biases trigger 204 into engagement with one of first ratchet assembly 210 and second ratchet assembly 212. In at least one embodiment, referring to FIG. 33, surgical instrument 200 can further include bistable compliant mechanism 270 which can bias trigger 204 out of an intermediate position described above and into engagement with either first ratchet assembly 210 and second ratchet assembly 212. In various embodiments, bistable compliant mechanism 270 can include spring 272 and link 274, where spring 272 can apply a biasing force to trigger 204 via link 274 such that the biasing force acts to move trigger 204 out of its intermediate position illustrated in FIG. 33 and into engagement with either first ratchet wheel 222 or second ratchet wheel 234. More particularly, when trigger 204 is positioned in its intermediate position, spring 272 can be stretched to a length X1 and, owing to the resiliency of spring 272, spring 272 can seek to shorten itself to its unstretched length, or at least a length shorter than X1, such as length X2 for example. In order for spring 272 to shorten itself to length X2, spring 272 can rotate link 274 about pin 275 where pin 275 can extend from and pivotably mount link 274 to surgical instrument housing 218. More particularly, as the first end of spring 272 is mounted to pin 276 extending from housing 218 and the second end of spring 272 is mounted to pin 277 extending from link 274, spring 272 can shorten itself by moving pin 277 closer to pin 276 which is most easily accomplished by rotating link 274 about pin 275. As link 274 is rotated about pin 275, the side walls of slot 278 in link 274 can be configured to engage pin 279 extending from trigger 204 and slide trigger 204 into engagement with first ratchet wheel 222 or second ratchet wheel 234. In effect, the intermediate position of trigger 204 illustrated in FIG. 33 represents a dynamically unstable position and the positions of trigger 204 where trigger 204 is engaged with ratchet wheels 222 and 234 represent the dynamically stable positions of the firing drive system.

Figure 31:
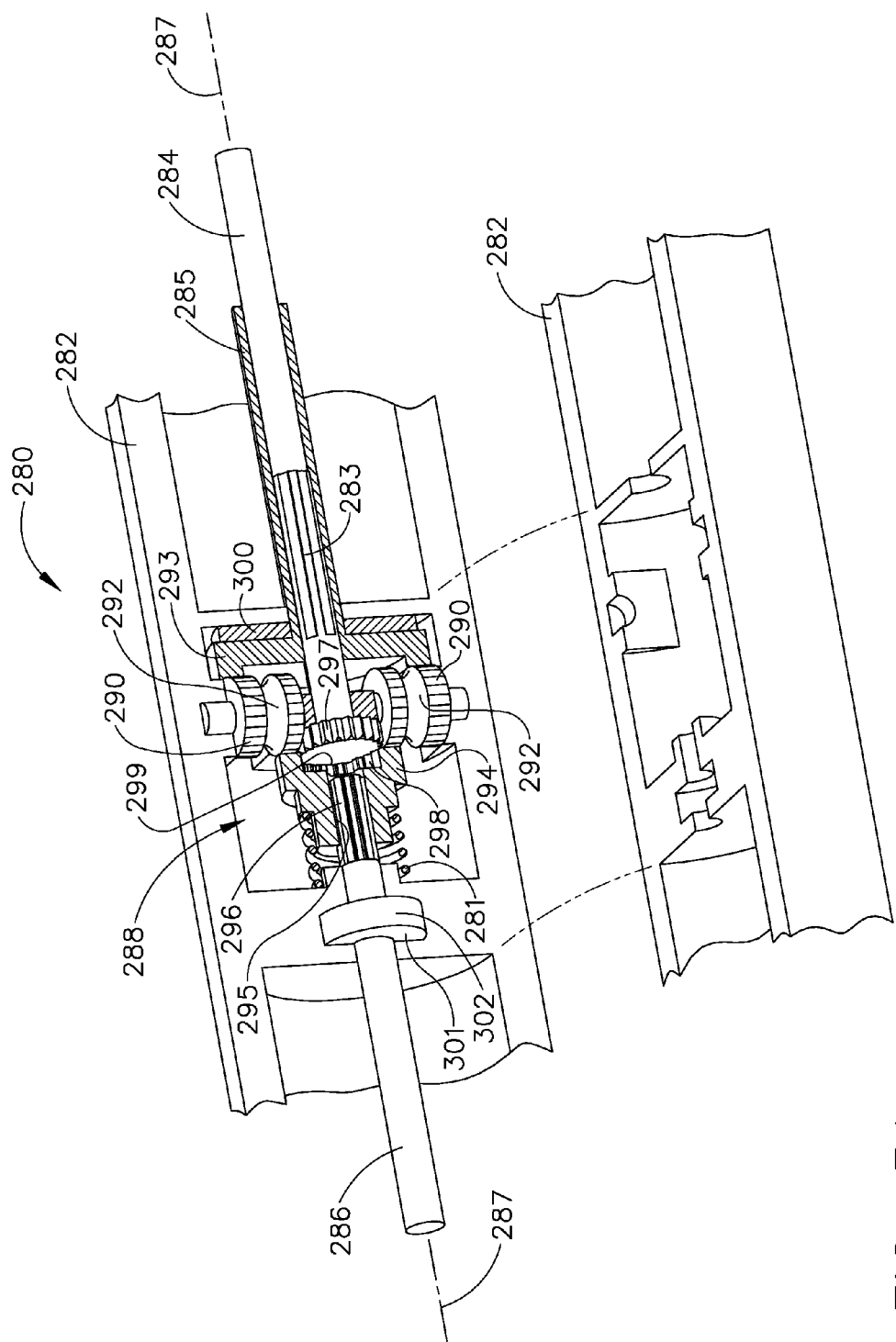
FIG. 31 is a perspective view of a directional switching mechanism in accordance with an alternative embodiment of the present invention with some components disassembled and other components illustrated in cross-section.
Figure 32:
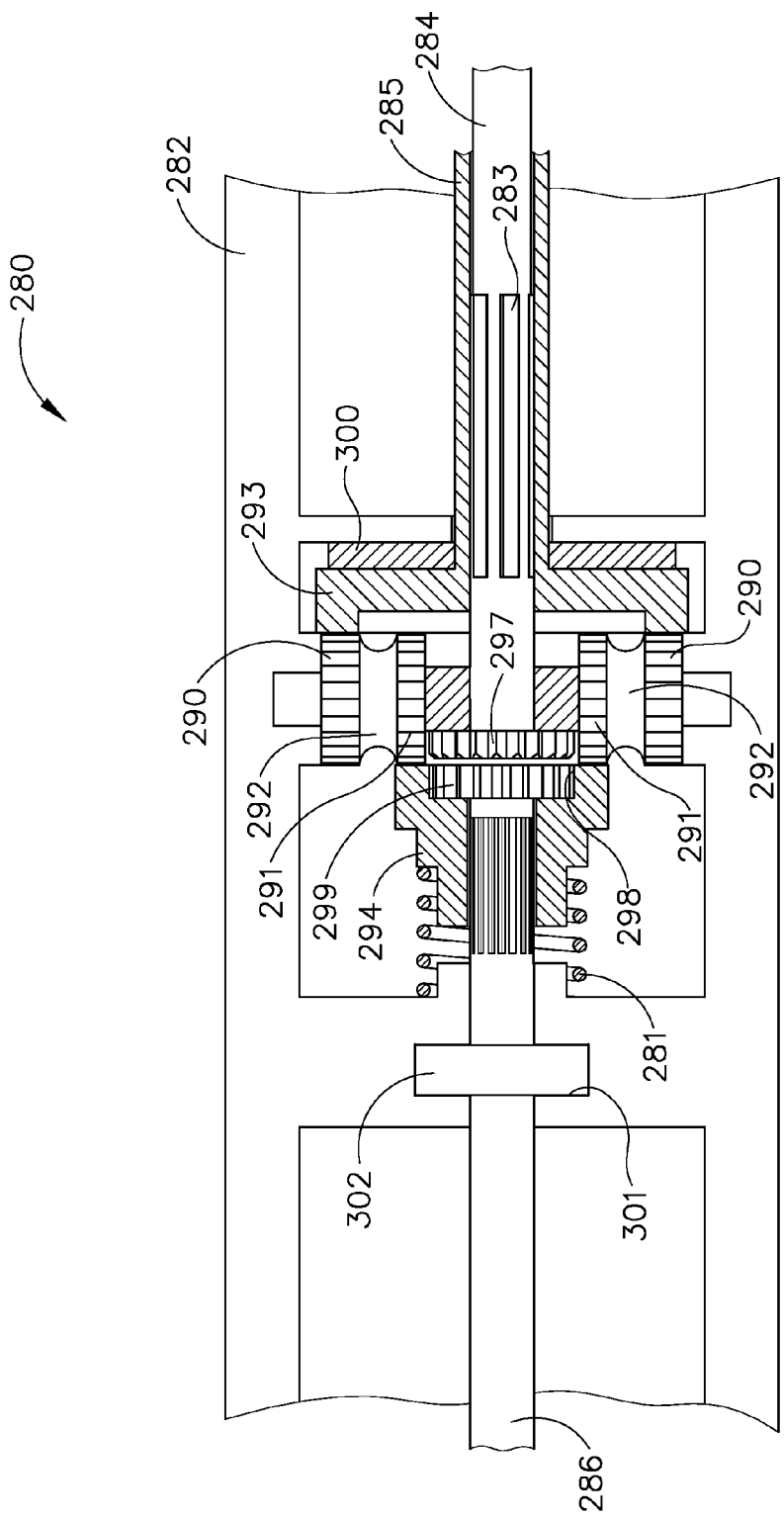
FIG. 32 is a plan view of the directional switching mechanism of FIG. 31 with some components removed and other components illustrated in cross-section.

In various embodiments, as described above, surgical instruments in accordance with the present invention can include devices for rotating a drive shaft in a first direction in which the drive shaft advances a cutting member within an end effector, for example, and a second direction in which the drive shaft retracts the cutting member. In at least one embodiment, referring to FIGS. 31 and 32, a surgical instrument can include transmission 280, for example, which can allow a surgeon to select whether the drive shaft advances or retracts the cutting member. In various embodiments, transmission 280 can include housing 282, internal input shaft 284, external input shaft 285, output drive shaft 286, and switching mechanism 288, where switching mechanism 288 can be configured to selectively engage internal input shaft 284 and external input shaft 285 with output shaft 286. Although not illustrated, the surgical instrument can further include a trigger, for example, which is operatively engaged with external drive shaft 285 in order to rotate drive shaft 285 about axis 287 in a clockwise direction, for example. In at least one embodiment, transmission 280 can include pinion gears 292 rotatably mounted within housing 282, input gear 293 fixedly mounted to external input shaft 285, and output gear 294 mounted to output drive shaft 286, where input gear 293 can be operably engaged with outer gear teeth 290 of pinion gears 292 such that the rotation of external shaft 285 is transmitted to pinion gears 292.

In a first configuration of transmission 280, output gear 294 can be operatively engaged with inner gear teeth 291 of pinion gears 292 such that the rotation of pinion gears 292 is transmitted to output drive shaft 286. More particularly, output gear 294 can be operably engaged with output drive shaft 286 via splined end 296 such that output gear 294 drives output drive shaft 286 about axis 287. In this first configuration, a clockwise rotation of external input shaft 285, for example, can be converted into a counter-clockwise motion of output drive shaft 286. In a second configuration of transmission 280, output gear 294 can be disengaged from pinion gears 292 such that the rotation of external input shaft 285 is not transmitted to output drive shaft 286 via pinion gears 292. In order to disengage output gear 294 from pinion gears 292, internal drive shaft 284 can be slid relative to external drive shaft 285 such that input gear 297 contacts recess 298 in output gear 294 and pushes output gear 294 away from pinion gears 292. In at least one embodiment, recess 298 can include teeth 299 which can be operatively engaged with input gear 297 of internal input shaft 284 such that the rotation of internal input shaft 284 is transmitted to output drive shaft 286. In this second configuration of transmission 280, a clockwise rotation of internal input shaft 284 can be directly transmitted to output drive shaft 286 such that output shaft 286 rotates in a clockwise direction as well. In order to reengage output gear 294 with pinion gears 292, internal input gear 284 can be disengaged from output gear 294 to allow spring 281 to slide output gear 294 along splined end 296.

In the embodiments described above, a surgeon can selectively move internal input shaft 284 relative to external input shaft 285 to place transmission 280 in either a forward or reversing configuration. In order to move input shaft 284, in various embodiments, the surgical instrument can further include an actuator or trigger configured to translate internal input shaft 284. In at least one embodiment, the surgical instrument can include a first actuator or trigger for rotating external input shaft 285 and a second actuator or trigger for translating internal shaft 284 relative to external shaft 285. In such embodiments, internal input shaft 284 can include splines 283 which can be slidably engaged with external input shaft 285 such that the rotation of external shaft 285 is transmitted to internal shaft 284 yet sliding motion is permitted therebetween. In at least one embodiment, transmission 280 can further include bearing 300 which can rotatably support input gear 293 and, when compressed between input gear 293 and housing 282, provide a biasing force to keep input gear 293 operably engaged with pinion gears 292. In various embodiments, output shaft 286 can include member 302 extending therefrom which can be configured to be received within recess 301 of housing 282 in order to reduce, or even eliminate, relative movement between output shaft 286 and housing 282. In at least one embodiment, although not illustrated, transmission 280 may only have one pinion gear 292 and still operate in the manner described above.

In various embodiments, transmission 280 can also be configured to advance cutting member 96, for example, at a different rate than which it is retracted. In at least one embodiment, referring to FIGS. 31 and 32, the operative engagement between internal input shaft 284 and output shaft 286 can be used to advance cutting member 96 and, owing to the direct engagement between input gear 297 and output gear 294, internal input shaft 284 and output shaft 286 can rotate in a 1:1 ratio, i.e., for every rotation of internal input shaft 284, output shaft 286 is rotated once. In various embodiments, the operative engagement between external input shaft 285 and output shaft 286 can be used to retract cutting member 96 and, owing to the different pitch radii of input gear 293 and output gear 294 and their operative engagement with pinions 292, external input shaft 285 and output shaft 286 can rotate in a ratio different than 1:1. In the illustrated embodiment, output shaft 286 can rotate at a faster speed than external input shaft 285 when they are mated via pinions 292. In various embodiments, as a result, cutting member 96 can be translated at a faster rate when external input shaft 285 is operably engaged with output shaft 286 than when internal input shaft 284 is operably engaged with output shaft 286.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical instrument, comprising:
   a firing drive configured to selectively generate a firing motion and a retraction motion, wherein said firing drive comprises:
   a firing trigger;
   a first drive member comprising a plurality of first gear teeth; and
   a second drive member comprising a plurality of second gear teeth; and
   a drive shaft, comprising:
   a first gear operably engageable with said first gear teeth; and
   a second gear operably engageable with said second gear teeth,
   wherein said firing trigger is selectively movable between a first position in which said firing trigger is operably engaged with said first drive member to transmit said firing motion to said drive shaft and a second position in which said firing trigger is operably engaged with said second drive member to transmit said retraction motion to said drive shaft, wherein when said firing trigger is in said first position said firing trigqer is operably disengaged from said second drive member, and wherein when said firing trigger is in said second position said firing trigger is operably disengaged from said first drive member.

2. The surgical instrument of claim 1, wherein said firing trigger is selectively slidable between said first position and said second position.

3. The surgical instrument of claim 1, wherein said firing trigger is rotatable about an axis of rotation, and wherein said firing trigger is selectively slidable along said axis of rotation between said first position and said second position.

4. The surgical instrument of claim 1, further comprising a staple cartridge assembly.

5. The surgical instrument of claim 1, further comprising:
   an end effector closure system;
   a closure trigger moveable between a nonactuated position and an actuated position, wherein said closure trigger is operably engaged with said end effector closure system; and
   a lock configured to secure said closure trigger in said actuated position.

6. The surgical instrument of claim 1, further comprising a bistable compliant mechanism configured to bias said firing trigger into one of said first position and said second position, wherein said firing trigger is biased into engagement with said first drive member in said first position, and wherein said firing trigger is biased into engagement with said second drive member in said second position.

7. A surgical instrument, comprising:
   a firing drive configured to selectively generate a firing motion and a retraction motion, wherein said firing drive comprises:
   a firing trigger;
   a first drive member comprising a plurality of first gear teeth;
   a second drive member comprising a plurality of second gear teeth; and
   a shaft assembly comprising:
   a drive shaft;
   a first gear operably engaged with said drive shaft, wherein said first gear is operably engageable with said first gear teeth; and
   a second gear operably engaged with said drive shaft, wherein said second gear is operably engageable with said second gear teeth,
   wherein said firing trigger is selectively movable between a first position in which said firing trigger is operably engaged with said first drive member to transmit said firing motion to said drive shaft and a second position in which said firing trigger is operably engaged with said second drive member to transmit said retraction motion to said drive shaft, wherein when said firing trigger is in said first position said firing trigger is operably disengaged from said second drive member, and wherein when said firing trigger is in said second position said firing trigger is operably disengaged from said first drive member; and
   a staple cartridge attachment portion configured to attach a staple cartridge assembly to said shaft assembly.

8. The surgical instrument of claim 7, wherein said firing trigger is selectively slidable between said first position and said second position.

9. The surgical instrument of claim 7, wherein said firing trigger is rotatable about an axis of rotation, and wherein said firing trigger is selectively slidable along said axis of rotation between said first position and said second position.

10. The surgical instrument of claim 7, further comprising said staple cartridge assembly.

11. The surgical instrument of claim 7, further comprising:
an end effector closure system;
a closure trigger moveable between a nonactuated position and an actuated position, wherein said closure trigger is operably engaged with said end effector closure system; and
a lock configured to secure said closure trigger in said actuated position.

12. The surgical instrument of claim 7, further comprising a bistable compliant mechanism configured to bias said firing trigger into one of said first position and said second position, wherein said firing trigger is biased into engagement with said first drive member in said first position, and wherein said firing trigger is biased into engagement with said second drive member in said second position.

13. A surgical instrument, comprising:
a handle;
a firing drive, comprising:
    a firing trigger operably coupled to said handle; and
    a drive shaft operably engaged with said firing trigger, wherein an actuation of said firing trigger rotates said drive shaft about an axis;
an elongate shaft assembly;
a transmission, wherein said transmission is selectively configurable in a first configuration for rotating said elongate shaft assembly about an axis in a first direction and a second configuration for rotating said elongate shaft assembly about said axis in a direction opposite said first direction, said transmission comprising a pinion gear, wherein said drive shaft is mated with said elongate shaft assembly in said first configuration such that said drive shaft and said elongate shaft assembly rotate in a first ratio, and wherein said drive shaft and said elongate shaft assembly are mated with said pinion gear in said second configuration such that said drive shaft and said elongate shaft assembly rotate in a second ratio, wherein said first ratio is different than said second ratio; and
a staple cartridge attachment portion configured to attach a staple cartridge assembly to said elongate shaft assembly.

14. A surgical instrument, comprising:
a firing drive configured to selectively generate a firing motion and a retraction motion, wherein said firing drive comprises:
    a firing trigger;
    a first drive member; and
    a second drive member; and
a drive shaft, comprising:
    a first portion operably engaged with said first drive member; and
    a second portion operably engaged with said second drive member;
wherein said firing trigger is selectively movable between a first position in which said firing trigger is operably engaged with said first drive member to transmit said firing motion to said drive shaft and a second position in which said firing trigger is operably engaged with said second drive member to transmit said retraction motion to said drive shaft, wherein when said firing trigger is in said first position said firing trigger is operably disengaged from said second drive member, and wherein when said firing trigger is in said second position said firing trigger is operably disengaged from said first drive member.

15. The surgical instrument of claim 14, wherein said firing trigger is selectively slidable between said first position and said second position.

16. The surgical instrument of claim 14, wherein said firing trigger is rotatable about an axis of rotation, and wherein said firing trigger is selectively slidable along said axis of rotation between said first position and said second position.

17. The surgical instrument of claim 14, further comprising a staple cartridge assembly.

18. The surgical instrument of claim 14, further comprising:
an end effector closure system;
a closure trigger moveable between a nonactuated position and an actuated position, wherein said closure trigger is operably engaged with said end effector closure system; and
a lock configured to secure said closure trigger in said actuated position.

19. The surgical instrument of claim 14, further comprising a bistable compliant mechanism configured to bias said firing trigger into one of said first position and said second position, wherein said firing trigger is biased into engagement with said first drive member in said first position, and wherein said firing trigger is biased into engagement with said second drive member in said second position.

20. The surgical instrument of claim 19, further comprising a frame, wherein said firing trigger further comprises a link coupled to said frame, wherein said bistable compliant mechanism comprises a spring operably engaged with said link and said frame, and wherein said spring is configured to motivate said link.

21. The surgical instrument of claim 20, wherein said link comprises a slot, wherein said firing trigger comprises a pin configured to slide in said slot, and wherein said link slides along said slot to guide said firing trigger into engagement with one of said first drive member and said second driver member.

22. The surgical instrument of claim 20, wherein said link is pivotally coupled to said frame.

23. A surgical instrument, comprising:
a firing drive configured to selectively generate a firing motion and a retraction motion, wherein said firing drive comprises:
    a firing trigger;
    a first drive member; and
    a second drive member;
a shaft assembly comprising:
    a drive shaft;
    a first portion operably engaged with said drive shaft, wherein said first portion is operably engaged with said first drive member; and
    a second portion operably engaged with said drive shaft, wherein said second portion is operably engaged with said second drive member,
wherein said firing trigger is selectively movable between a first position in which said firing trigger is operably engaged with said first drive member to transmit said firing motion to said drive shaft and a second position in which said firing trigger is operably engaged with said second drive member to transmit said retraction motion to said drive shaft, wherein when said firing trigger is in said first position said firing trigger is operably disengaged from said second drive member, and wherein when said firing trigger is in said second position said firing trigger is operably disengaged from said first drive member; and a staple cartridge attachment portion configured to attach a staple cartridge assembly to said shaft assembly.

24. The surgical instrument of claim 23, wherein said firing trigger is selectively slidable between said first position and said second position.

25. The surgical instrument of claim 23, wherein said firing trigger is rotatable about an axis of rotation, and wherein said firing trigger is selectively slidable along said axis of rotation between said first position and said second position.

26. The surgical instrument of claim 23, further comprising said staple cartridge assembly.

27. The surgical instrument of claim 23, further comprising:
   an end effector closure system;
   a closure trigger moveable between a nonactuated position and an actuated position, wherein said closure trigger is operably engaged with said end effector closure system; and
   a lock configured to secure said closure trigger in said actuated position.

28. The surgical instrument of claim 23, further comprising a bistable compliant mechanism configured to bias said firing trigger into one of said first position and said second position, wherein said firing trigger is biased into engagement with said first drive member in said first position, and wherein said firing trigger is biased into engagement with said second drive member in said second position.

* * * * *